US008082136B2

(12) United States Patent
Chen

(10) Patent No.: US 8,082,136 B2
(45) Date of Patent: Dec. 20, 2011

(54) COMPUTER METHOD AND SYSTEM FOR PREDICTING PHYSICAL PROPERTIES USING A CONCEPTUAL SEGMENT MODEL

(75) Inventor: Chau-Chyun Chen, Lexington, MA (US)

(73) Assignee: Aspen Technology, Inc., Burlington, MA (US)

( * ) Notice: Subject to any disclaimer, the term of this patent is extended or adjusted under 35 U.S.C. 154(b) by 1138 days.

(21) Appl. No.: 11/899,996

(22) Filed: Sep. 7, 2007

(65) Prior Publication Data

US 2008/0076187 A1    Mar. 27, 2008

Related U.S. Application Data

(63) Continuation-in-part of application No. 11/528,749, filed on Sep. 27, 2006, now Pat. No. 7,941,277, and a continuation-in-part of application No. 11/241,675, filed on Sep. 30, 2005, now Pat. No. 7,809,540, which is a continuation-in-part of application No. 10/785,925, filed on Feb. 24, 2004, now Pat. No. 7,672,826.

(51) Int. Cl.
  G06G 7/48    (2006.01)
  G01N 33/48   (2006.01)
  G01N 31/00   (2006.01)
  G06F 7/58    (2006.01)
(52) U.S. Cl. ............... 703/13; 702/19; 702/22; 703/12
(58) Field of Classification Search ................. None
See application file for complete search history.

(56) References Cited

U.S. PATENT DOCUMENTS

| 5,687,090 | A  | 11/1997 | Chen et al. |
| 6,311,093 | B1 | 10/2001 | Brown |
| 6,311,095 | B1 | 10/2001 | Brown |
| 6,662,061 | B1 | 12/2003 | Brown |
| 6,766,817 | B2 | 7/2004  | da Silva |
| 6,918,404 | B2 | 7/2005  | da Silva |
| 7,066,586 | B2 | 6/2006  | da Silva |
| 2005/0187748 | A1 | 8/2005 | Chen et al. |

FOREIGN PATENT DOCUMENTS

EP    0463694 A2    1/1992

OTHER PUBLICATIONS van de Waterbeemd, H., and Gifford, E., "Admet In Silico Modelling: Towards Prediction Paradise?", *Nature Publishing Group*, Mar. 2003, vol. 2: 192-204.
Chen, C-C., et al., "Segment-Based Excess Gibbs Energy Model for Aqueous Organic Electrolytes", *AIChE Journal*, Nov. 2001, vol. 47, No. 11, 2593-2602.
Chen, C-C., "Molecular Thermodynamic Model for Gibbs Energy of Mixing of Nonionic Surfactant Solutions", *AIChE Journal*, Nov. 1996, vol. 42, No. 11, 3231-3240.
Chen, C-C., and Mathias, P.M., "Applied Thermodynamics for Process Modeling", *AIChE Journal*, Feb. 2002, vol. 48, No. 2, 194-200.
Chen, C-C., "A Segment-Based Local Composition Model for the Gibbs Energy or Polymer Solutions", *Fluid Phase Equilibria*, vol. 83 (1993), 301-312.
Stahl, P. Heinrich and Wermuth, Camille G., "Handbook of Pharmaceutical Salts Properties, Selection, and Use," *International Union of Pure and Applied Chemistry (IUPAC)*, Wiley-VCH.
Wilczek-Vera, Grazyna, et al., "On The Activity Of Ions And The Junction Potential: Revised Values For All Data," *AIChE Journal*, 50(2):445-462 (2004).
Gracin, S. and Rasmuson, A. C., "Solubility of Phenylacetic Acid, p-Hydroxyphenylacetic Acid, p-Aminophenylacetic Acid, p-Hydroxybenzoic Acid, and Ibuprofen in Pure Solvents," *J. Chem. Eng. Data*, 47:1379-1383 (2002).
Frank, T. C., et al., "Quickly Screen Solvents for Organic Solids," *Chemical Engineering Progress*, pp. 41-66 (1999).
Hansen, C. M., "Hansen Solubility Parameters A User's Handbook," *CRC Press* (2000).
Fredenslund, A., et al., "Group-Contribution Estimation of Activity Coefficients in Nonideal Liquid Mixtures," *AIChE Journal*, 21(6): 1086-1099 (1975).
Chen, C. C., and Song, Y., "Solubility Modeling with a Nonrandom Two-Liquid Segment Activity Coefficient Model," *Ind. Eng. Chem. Res*, 43(26):8354-8362 (2004).
Chen, C. C., and Song, Y.,"Generalized Electrolyte-NRTL Model for Mixed-Solvent Electrolyte Systems," *AIChE Journal*, 50(8):1928-1941 (2004).
Pitzer, K. S., "Electrolytes. From Dilute Solutions to Fused Salts," *Journal Of The American Chemical Society*, 102(9):2902-2906 (1980).
Pitzer, K. S., "Thermodynamics of Electrolytes. I. Theoretical Basis And General Equations," *The Journal of Physical Chemistry*, 77(2):267-277 (1973).
Robinson, R. A., D.Sc., Ph.D., F.R.I.C., et al., "Electrolyte Solutions The Measurement and Interpretation Of Conductance, Chemical Potential and Diffusion in Solutions of Simple Electrolytes," Butterworths Scientific Publications Second Edition (1959).
Rashin, A. A. and Honig, B., "Reevaluation Of The Born Model Of Ion Hydration," *J. Phys. Chem.*, 89 (26):5588-5593 (1985).
Chen, C-C., et al., "Use of Hydration and Dissociation Chemistries With The Electrolyte-NRTL Model," *AIChE Journal*, 45(7):1576-1586 (1999).
Beerbower, A., et al., "Expanded Solubility Parameter Approach I: Naphthalene and Benzoic Acid in Individual Solvents," *Journal of Pharmaceutical Sciences*, 73(2):179-188 (1984).
Bustamante, P., et al., "The Modified Extended Hansen Method To Determine Partial Solubility Parameters Of Drugs Containing A Single Hydrogen Bonding Group And Their Sodium Derivatives: Benzoic Acid/Na And Ibuprofen/Na," *International Journal of Pharmaceutics*, 194:117-124 (2000).
Barra, J., et al., "Proposition Of Group Molar Constants For Sodium To Calculate The Partial Solubility Parameters of Sodium Salts Using The van Krevelen Group Contribution Method," *European Journal of Pharmaceutical Sciences*, 10:153-161 (2000).

(Continued)

*Primary Examiner* — Eric S Dejong

(74) *Attorney, Agent, or Firm* — Hamilton, Brook, Smith & Reynolds, P.C.

(57) ABSTRACT

Method of conducting chromatography comprising controlling a retention time of one or more chemical species in a mixture by determining at least one conceptual segment of: a) the one or more chemical species, b) a mobile phase component, and c) a stationary phase component. The method further includes defining an identity and an equivalent number of each of the at least one conceptual segment.

20 Claims, 40 Drawing Sheets

OTHER PUBLICATIONS

Miller, J.M. *Chromatography, Concepts and Contrasts*. 2$^{nd}$ ed. New Jersey: Wiley-Interscience Publication, John Wiley & Sons, Inc., 2005.

Ahamed, T., et al., "A Generalized Approach to Thermodynamic Properties of Biomolecules for Use in Bioseparation Process Design," *Fluid Phase Equilibria*, 241: 268-282 (2006).

Park, J.H., et al., "UNIFAC Model as a Heuristic Guide for Estimating Retention in Chromatography," *J. of Chromatography*, 586: 1-9 (1991).

Park, J.H., et al., "UNIFAC Model as a Heuristic Guide for Estimating Retention in Reversed-Phased Liquid Chromatography," *J. of Chromatography A*, 656: 69 (1993).

Synder, L.R., et al. *Practical HPLC Method Development*. 2$^{nd}$ ed. New Jersey: Wiley-Interscience Publication, John Wiley & Sons, Inc., 1997.

Chen, C.-C. and Song Y., "Extension of Nonrandom Two-Liquid Segment Activity Coefficient Model for Electrolytes," *Ind. Eng. Chem. Res.*, 44(23): 8909-8921 (2005).

Chen, C.-C and Crafts, P.A., "Correlation and Prediction of Drug Molecule Solubility in Mixed Solvent Systems with the Nonrandom Two-Liquid Segment Activity Coefficient (NRTL-SAC) Model," *Ind. Eng. Chem. Res.*, 45: 4816-4824 (2006).

Tung, H.-H., et al., "Prediction of Pharmaceuticals Solubility via NRTL-SAC and Cosmo," *VDI Berichte*, 1901(1): 271-278 (2005).

Lipinski, et al., "Experimental and computational approaches to estimate solubility and permeability in drug discovery and development settings," *Advanced Drug Delivery Reviews*, 23: 3-25 (1997) (No month available).

Gani, et al., "A Modern Approach to Solvent Selection," *Chemical Engineering*, pp. 30-43 (Mar. 2006).

Anderko A., et al., "Electrolyte Solutions: from thermodynamic and transport property models to the simulation of industrial processes," *Fluid Phase Equilibria*, 194-197:123-142 (2002).

Chen, C-C., et al., "Local Composition Model For Excess Gibbs Energy of Electrolyte Systems," *AIChE Journal*, 28(4):588-596 (1982).

Wang, et al., "A speciation-based model for mixed-solvent electrolyte systems," *Fluid Phase Equilibria*, 203(1-2):141-176 (2002).

US 8,082,136 B2

COMPUTER METHOD AND SYSTEM FOR PREDICTING PHYSICAL PROPERTIES USING A CONCEPTUAL SEGMENT MODEL

RELATED APPLICATIONS

This application is a continuation-in-part of U.S. application Ser. No. 11/528,749, filed Sep. 27, 2006, now U.S. Pat. No. 7,941,227, which is a continuation-in-part of U.S. application Ser. No. 10/785,925, filed Feb. 24, 2004, now U.S. Pat. No. 7,672,826, and of U.S. application Ser. No. 11/241,675, filed Sep. 30, 2005, now U.S. Pat. No. 7,809,540, which is a continuation-in-part of the U.S. application Ser. No. 10/785,925, filed Feb. 24, 2004, now U.S. Pat. No. 7,672,826. The entire teachings of the applications are incorporated herein by reference.

BACKGROUND OF THE INVENTION

Modeling physical properties of chemical mixtures is an important task in many industries and processes. Specifically, for many processes, accurate modeling of physical properties for various mixtures is crucial for such areas as process design and process control applications. For example, modeling physical properties of chemical mixtures is often useful when selecting suitable solvents for use in chemical processes.

Solvent selection is an important task in the chemical synthesis and recipe development phase of the pharmaceutical and agricultural chemical industries. The choice of solvent can have a direct impact on reaction rates, extraction efficiency, crystallization yield and productivity, etc. Improved solvent selection brings benefits, such as faster product separation and purification, reduced solvent emission and lesser waste, lower overall costs, and improved production processes.

In choosing a solvent, various phase behavior characteristics of the solvent-solute mixtures are considered. For example, vapor-liquid equilibrium (VLE) behavior is important when accounting for the emission of solvent from reaction mixtures, and liquid-liquid miscibility (LLE) is important when a second solvent is used to extract target molecules from the reaction media. For solubility calculations, solid-liquid equilibrium (SLE) is a key property when product isolation is done through crystallization at reduced temperature or with the addition of anti-solvent.

For many applications, hundreds of typical solvents, not to mention an almost infinite number of mixtures thereof, are candidates in the solvent selection process. In most cases, there is simply insufficient phase equilibrium data on which to make an informed solvent selection. For example, in pharmaceutical applications, it is often the case that phase equilibrium data involving new drug molecules in the solvents simply do not exist. Although limited solubility experiments may be taken as part of the trial and error process, solvent selection is largely dictated by researchers' preferences or prior experiences.

Many solubility estimation techniques have been used to model the solubility of components in chemical mixtures. Some examples include the Hansen model and the UNIFAC group contribution model. Unfortunately, these models are rather inadequate because they have been developed mainly for petrochemicals with molecular weights in the 10s and the low 100s daltons. These models do not extrapolate well for chemicals with larger molecular weights, such as those encountered in pharmaceutical applications. Pharmaceuticals are mostly large, complex molecules with molecular weight in the range of about 200-600 daltons.

Perhaps, the most commonly used methods in solvent selection process are the solubility parameter models, i.e., the regular solution theory and the Hansen solubility parameter model. There are no binary parameters in these solubility parameter models and they all follow merely an empirical guide of "like dissolves like." The regular solution model is applicable to nonpolar solutions only, but not for solutions where polar or hydrogen-bonding interactions are significant. The Hansen model extends the solubility parameter concept in terms of three partial solubility parameters to better account for polar and hydrogen-bonding effects.

In his book, Hansen published the solubility parameters for over 800 solvents. See Hansen, C. M., HANSEN, SOLUBILITY PARAMETERS: A USER'S HANDBOOK (2000). Since Hansen's book contains the parameters for most common solvents, the issue in using the Hansen model lies in the determination of the Hansen solubility parameters from regression of available solubility data for the solute of interest in the solvent selection process. Once determined, these Hansen parameters provide a basis for calculating activity coefficients and solubilities for the solute in all the other solvents in the database. For pharmaceutical process design, Bakken, et al. reported that the Hansen model can only correlate solubility data with ±200% in accuracy, and it offers little predictive capability. See Bakken, et al., *Solubility Modeling in Pharmaceutical Process Design*, paper presented at AspenTech User Group Meeting, New Orleans, La., Oct. 5-8, 2003, and Paris, France, Oct. 19-22, 2003.

When there are no data available, the UNIFAC functional group contribution method is sometimes used for solvent selection. In comparison to the solubility parameter models, UNIFAC's strength comes with its molecular thermodynamic foundation. It describes liquid phase nonideality of a mixture with the concept of functional groups. All molecules in the mixture are characterized with a set of pre-defined UNIFAC functional groups. The liquid phase nonideality is the result of the physical interactions between these functional groups and activity coefficients of molecules are derived from those of functional groups, i.e., functional group additivity rule. These physical interactions have been pre-determined from available phase equilibrium data of systems containing these functional groups. UNIFAC gives adequate phase equilibrium (VLE, LLE and SLE) predictions for mixtures with small nonelectrolyte molecules as long as these molecules are composed of the pre-defined set of functional groups or similar groups.

UNIFAC fails for systems with large complex molecules for which either the functional group additivity rule becomes invalid or due to undefined UNIFAC functional groups. UNIFAC is also not applicable to ionic species, an important issue for pharmaceutical processes. Another drawback with UNIFAC is that, even when valuable data become available, UNIFAC cannot be used to correlate the data. For pharmaceutical process design, Bakken et al., reported that the UNIFAC model only predicts solubilities with a RMS (root mean square) error on ln x of 2, or about +500% in accuracy, and it offers little practical value. Id.

A need exists for new, simple, and practical methods of accurately modeling one or more physical properties of a mixture of chemicals, including electrolytes.

SUMMARY OF THE INVENTION

The present invention provides an effective tool for the correlation and prediction of physical properties of a mixtures of chemical species, including electrolytes.

The present invention provides an effective tool for conducting chromatography based on the correlation and prediction of physical properties of a mixtures of chemical species.

In a first embodiment of the present invention, the present invention features methods of conducting chromatography. The methods comprise steps of controlling a retention time of one or more chemical species in a mixture by determining at least one conceptual segment of: a) the one or more chemical species, b) a mobile phase component and c) a stationary phase component. The methods further include defining an identity and an equivalent number of each of the at least one conceptual segment.

In another embodiment, the methods further comprise a step of separating the one or more chemical species from the mixture.

In yet another embodiment, the methods include controlling a retention time of one or more chemical species in a mixture, and includes computing at least one physical property for each of the one or more chemical species, the mobile phase component and the stationary phase component. The at least one physical property is computed using the determined at least one conceptual segment and the equivalent number.

In a second embodiment, the present invention features methods of conducting chromatography for separating one or more chemical species from a mixture. The methods comprise a step of assigning molecular descriptors based on molecular interaction characteristics to each of: (i) the one or more chemical species, (ii) a mobile phase component, and (iii) a stationary phase component. The methods include measuring respective molecular interaction indices for the one or more chemical species, for the mobile phase component and for the stationary phase component. The methods also include determining respective activity coefficients of: (i) the one or more chemical species, (ii) the mobile phase component, and (iii) the stationary phase component, such that the determined respective activity coefficients enables conducting chromatography for separating the one or more chemical species from the mixture.

In another embodiment, measuring respective molecular interaction indices for the one or more chemical species, for the mobile phase component and for the stationary phase component includes determining the molecular interaction indices based on measures of effective surface areas expressing surface molecular interaction characteristics for each of the one or more chemical species, of the mobile phase component, and of the stationary phase component.

In another embodiment, assigning one or more predetermined molecular descriptors based on molecular interactive characteristics includes assigning one or more predetermined conceptual segments to each of the one or more chemical species, of the mobile phase component and of the stationary phase component.

In another embodiment, measuring respective molecular interaction indices for the one or more chemical species, and the mobile phase component and the stationary phase component includes determining an equivalent number for the predetermined conceptual segment.

In a third embodiment, the present invention is a computer program product. The computer program includes a computer usable medium, and a set of computer program instructions embodied on the computer usable medium for conducting chromatography for separating a one or more chemical species from a mixture by:

a) assigning molecular descriptors based on molecular interaction characteristics to each of: (i) the one or more chemical species, (ii) a mobile phase component, and (iii) a stationary phase component;

b) measuring respective molecular interaction indices for the one or more chemical species, for the mobile phase component and for the stationary phase component; and c) determining respective activity coefficients of: (i) the one or more chemical species; (ii) the mobile phase component; and (iii) the stationary phase component, such that the determined respective activity coefficients enables conducting chromatography for separating the one or more chemical species from the mixture.

In a fourth embodiment, the present invention features a computer system for conducting chromatography. The computer system includes a user input means for obtaining empirical data from a user, and a digital processor coupled to receive the empirical data from the input means. The digital processor executes a modeling system in working memory, and the modeling system uses the empirical data for assigning molecular descriptors based on molecular interaction characteristics to each of: (i) each of the one or more chemical species, (ii) a mobile phase component, and (iii) a stationary phase component; measuring respective molecular interactive indices for the one or more chemical species, and the mobile phase component and for the stationary phase component, and determining activity coefficients of: (i) the one or more chemical species, (ii) the mobile phase component, and (iii) the stationary phase component such that the determined respective activity coefficients enables conducting chromatography for separating the one or more chemical species from the mixture.

In one embodiment of the computer system, the chromatography includes reverse-phase chromatography, normal phase chromatography, hydrophobic interaction chromatography, hydrophilic interaction chromatography, ion-pair chromatography, or ion-exchange chromatography or other chromatography.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
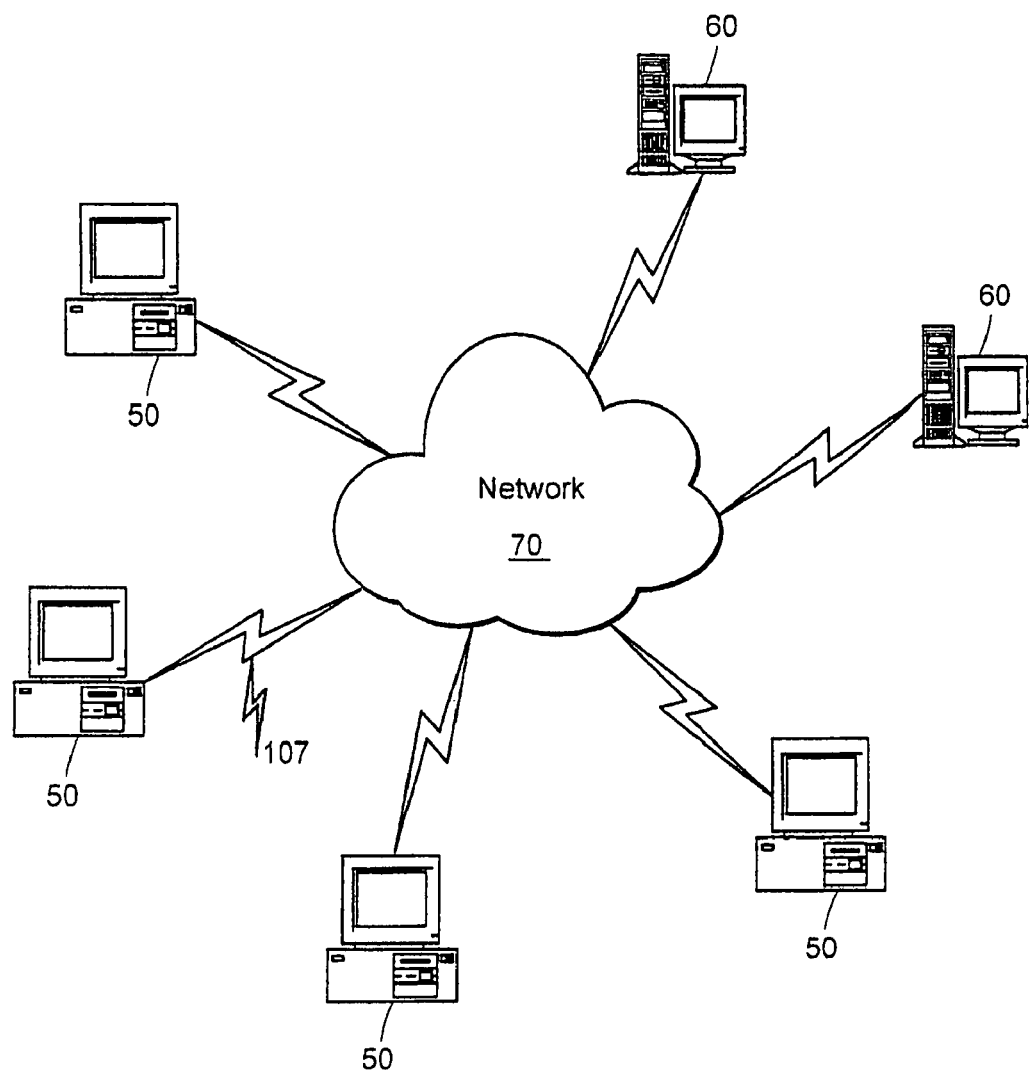
FIG. 1 is a schematic view of a computer network in which the present invention may be implemented.

A description of example embodiments of the invention follows.

The terms "conceptual segments" refer to molecular descriptors, based on expressed characteristics of molecular interactions between two species (e.g., a solute species in a solution interacting with the surface of the stationary phase in a chromatography processes) as one skilled in the art would understand. In certain embodiments, conceptual segments describe for each solute and solvent molecule their effective surface interaction in terms of the following types of the conceptual segments: hydrophobic segment, polar segment, hydrophilic segment, and solvation segment. The conceptual segments are to simulate the interaction characteristics of representative molecular surfaces. For example, the hydrophilic segment simulates polar molecular surfaces that are "hydrogen bond donor or acceptor." As such, it represents molecular surfaces with the tendency to form a hydrogen bond. Conversely, the hydrophobic segment simulates molecular surfaces with the adversity to form a hydrogen bond. As for the polar segment, it simulates polar molecular surfaces that are "electron pair donor or acceptor." With the conceptual segments identified, real molecules are then selected as reference molecules for the conceptual segments and available phase equilibrium data of these reference molecules are used to identify molecular interaction energy parameters for the conceptual segments. The reference molecules with distinct molecular characteristics (i.e., hydrophobic, hydrophilic, or polar) and with abundant, publicly available phase equilibrium data are chosen for practical purposes.

The term "equivalent numbers" of the conceptual segments, which is interchangeably used with "conceptual segment numbers" in this application, refers to measures of the surface areas of a molecule that are associated with a molecular interaction with another molecule. The molecular interaction can be characterized according to the types of the conceptual segments such as hydrophobicity, polarity, hydrophilicity and solvation. These measures of the molecular interaction can be determined from methods known by one skilled in the art including the interaction characteristics of the molecules in solution as expressed in available experimental data such as their experimental phase equilibrium data.

The present invention provides a new system and method for modeling the physical properties or behavior of chemical mixtures (e.g., chemical solutions or suspensions). Briefly, the molecular structure of one or more species in a chemical mixture is assigned one or more different types of "conceptual segments." An equivalent number is determined for each conceptual segment. This conceptual segment approach of the present invention is referred to as the Non-Random Two-Liquid Segment Activity Coefficient ("NRTL-SAC") model for nonelectrolytes and as the electrolyte extension of NRTL-SAC ("eNRTL-SAC") model for electrolytes.

In some embodiments, this invention features methods of conducting industrial manufacture, research or development. In one embodiment, the methods comprise computer implemented steps of modeling at least one physical property of a mixture of at least two chemical species by determining at least one conceptual segment for each of the chemical species. Determining at least one conceptual segment includes defining an identity and an equivalent number of each conceptual segment.

In one embodiment, the methods of conducting industrial manufacture, research or development further include the steps of: using the determined conceptual segments, computing at least one physical property of the mixture; and b) providing an analysis of the computed physical property. The analysis forms a model of the at least one physical property of the mixture.

In further embodiment, the method of the first embodiment that includes the mixture includes more than one phase and at least a portion of at least one chemical species is in a liquid phase. In one embodiment, the mixture includes any number and combination of vapor, solid, and liquid phase. In some embodiment, the mixture includes at least one liquid phase and at least one solid phase. In yet another embodiment, the mixture includes a first liquid phase, a second liquid phase, and a first chemical species. At least a portion of the first chemical species is dissolved in both the first liquid phase and the second liquid phase.

In further embodiments, the methods of the first embodiment can compute solubility of at least one of the chemical species in at least one phase of the mixture.

In further embodiments, the methods of the first embodiment can define the identity that includes identifying each conceptual segment as one of a hydrophobic segment, a hydrophilic segment, or a polar segment.

The methods of this invention can model a wide range of chemical mixtures of nonelectrolytes and electrolytes. For example, the chemical mixtures can include one or more of the following types of chemical species: an electrolyte, an organic nonelectrolyte, an organic salt, a compound possessing a net charge, a zwitterions, a polar compound, a nonpolar compound, a hydrophilic compound, a hydrophobic compound, a petrochemical, a hydrocarbon, a halogenated hydrocarbon, an ether, a ketone, an ester, an amide, an alcohol, a glycol, an amine, an acid, water, an alkane, a surfactant, a polymer, and an oligomer.

In further embodiments, the mixture includes at least one chemical species which is a solvent (e.g., a solvent used in a pharmaceutical production, screening, or testing process), a solute, a pharmaceutical component, a compound used in an agricultural application (e.g., a herbicide, a pesticide, or a fertilizer) or a precursor of a compound used in an agricultural application, a compound used in an adhesive composition or a precursor of a compound used in an adhesive composition, a compound used in an ink composition or a precursor of a compound used in an ink composition. As used herein, a "pharmaceutical component" includes a pharmaceutical compound, drug, therapeutic agent, or a precursor thereof (i.e., a compound used as an ingredient in a pharmaceutical compound production process). The "pharmaceutical component" of this invention can be produced by any publicly known method or by any method equivalent with the former. The pharmaceutical agent or other active compound of the present invention may comprise a single pharmaceutical ingredient or a combination of pharmaceutical ingredients, including active ingredients. These active ingredients may be incorporated in the adhesive layer, backing layer or in both. A pharmaceutical component can also include ingredients for enhancing drug solubility and/or stability of the drug to be added to the layer or layers containing the active ingredient. In some embodiments, the mixture includes at least one pharmaceutical component having a molecular weight greater than about 900 daltons, at least one pharmaceutical component having a molecular weight in the range of between about 100 daltons and about 900 daltons, and/or at least one pharmaceutical component having a molecular weight in the range of between about 200 daltons and about 600 daltons. In further embodiments, the mixture includes at least one nonpolymeric pharmaceutical component.

In further embodiments, the mixture includes at least one ICH solvent, which is a solvent listed in the *ICH Harmonized Tripartite Guideline, Impurities: Guideline for Residual Solvents Q3C*, incorporated herein in its entirety by reference. ICH STEERING COMMITTEE, *ICH Harmonized Tripartite Guideline, Impurities: Guideline for Residual Solvents Q3C*, International Conference of Harmonization of Technical Requirements for Registration of Pharmaceuticals for Human Use (1997).

It will be apparent to those skilled in the art that a component of the mixture can belong to more than one type of chemical species.

In accordance with one aspect of the present invention, at least one conceptual segment (e.g., at least 1, 2, 3, 4, 5, 7, 10, 12, or more than 12 conceptual segments) is determined or defined for each of the chemical species of the mixture. The conceptual segments are molecular descriptors of the various molecular species in the mixture. An identity and an equivalent number are determined for each of the conceptual segments. Examples of identities for conceptual segments include a hydrophobic segment, a polar segment, a hydrophilic segment, a charged segment, and the like. Experimental phase equilibrium data can be used to determine the equivalent number of the conceptual segment(s).

The determined conceptual segments are used to compute at least one physical property of the mixture, and an analysis of the computed physical property is provided to form a model of at least one physical property of the mixture. The methods of this invention are able to model a wide variety of physical properties. Examples of physical properties include vapor pressure, solubility (e.g., the equilibrium concentration of one or more chemical species in one or more phases of the mixture), boiling point, freezing point, octanol/water partition coefficient, lipophilicity, and other physical properties that are measured or determined for use in the chemical processes.

Preferably, the methods provide equilibrium values of the physical properties modeled. For example, a mixture can include at least one liquid solvent and at least one solid pharmaceutical component and the methods can be used to model the solubility of the pharmaceutical component. In this way, the methods can provide the concentration of the amount (e.g., a concentration value) of the pharmaceutical component that will be dissolved in the solvent at equilibrium. In another example, the methods can model a mixture that includes a solid phase (e.g., a solid pharmaceutical component) and at least two liquid phases (e.g., two solvent that are immiscible in one another). The model can predict, or be used to predict, how much of the pharmaceutical component will be dissolved in the two liquid phases and how much will be left in the solid phase at equilibrium. In yet a further embodiment, the methods can be used to predict the behavior of a mixture after a change has occurred. For example, if the mixture includes two liquid phases and one solid phase, and an additional chemical species is introduced into the mixture (e.g., a solvent, pharmaceutical component, or other chemical compound), additional amounts of a chemical species are introduced into the mixture, and/or one or more environmental conditions are changes (e.g., a change in temperature and/or pressure), the method can be used to predict how the introduction of the chemical species and/or change in conditions will alter one or more physical properties of the mixture at equilibrium.

The models of the physical property or properties of the mixture are produced by determining the interaction characteristics of the conceptual segments. In some embodiments, the segment-segment interaction characteristics of the conceptual segments are represented by their corresponding binary NRTL parameters. (See Example 11.) Given the NRTL parameters for the conceptual segments and the numbers and types of conceptual segments for the molecules, the NRTL-SAC model computes activity coefficients for the segments and then for the various molecules in the mixture. In other words, the physical properties or behavior of the mixture will be accounted for based on the segment compositions of the molecules and their mutual interactions. The activity coefficient of each molecule is computed from the number and type of segments for each molecule and the corresponding segment activity coefficients.

In one embodiment, the invention features methods of conducting industrial manufacture, research or development where the at least two chemical species includes at least one electrolyte. Electrolytes dissociate to ionic species in solutions. For "strong" electrolytes, the dissociation is "completely" to ionic species. For "weak" electrolytes, the dissociation is partially to ionic species while undissociated electrolytes, similar to nonelectrolytes, remain as neutral molecular species. Complexation of ionic species with solvent molecules or other ionic species may also occur. An implication of the electrolyte solution chemistry is that the extended model should provide a thermodynamically consistent framework to compute activity coefficients for both molecular species and ionic species.

Preferably, the method comprises computer implemented steps of: (a) using the determined conceptual electrolyte segment, computing at least one physical property of the mixture; and (b) providing an analysis of the computed physical property. The analysis forms a model of the at least one physical property of the mixture. The methods of this invention are able to model a wide variety of physical properties involving electrolytes, including activity coefficient, vapor pressure, solubility, boiling point, freezing point, octanol/water partition coefficient, and lipophilicity of the electrolyte.

The computed physical property of the analysis can include at least one of activity coefficient, vapor pressure, solubility, boiling point, freezing point, octanol/water partition coefficient, and lipophilicity of the electrolyte.

In a more preferred embodiment, the step of computing at least one physical property includes calculating the activity coefficient of the ionic species derived from the electrolyte.

In further embodiments, the methods include the electrolyte that is any one of a pharmaceutical compound, a non-polymeric compound, a polymer, an oligomer, an inorganic compound and an organic compound. In some embodiment, the electrolyte is symmetrical or unsymmetrical. In another embodiment, the electrolyte is univalent or multivalent. In yet another embodiment, the electrolyte includes two or more ionic species.

In some embodiments, the invention features methods of conducting a pharmaceutical activity. In one embodiment, the methods comprise the computer implemented steps of modeling at least one physical property of a mixture of at least two chemical species by determining at least one conceptual segment for each of the chemical species. Determining at least one conceptual segment includes defining an identity and an equivalent number of each conceptual segment.

The term "pharmaceutical activity", as used herein, has the meaning commonly afforded the term in the art. A pharmaceutical activity can include ones for drug discovery, development or manufacture. Particularly, a pharmaceutical activity can include one that is art, practice, or profession of researching, preparing, preserving, compounding, and dispensing medical drugs and that is of, relating to, or engaged in pharmacy or the manufacture and sale of pharmaceuticals. A pharmaceutical activity further includes the branch of health/medical science and the sector of public life concerned with maintaining or restoring human/mammalian health through the study, diagnosis and treatment of disease and injury. It includes both an area of knowledge—i.e. the chemical make-up of a drug—and the applied practice—i.e. drugs in relation to some diseases and methods of treatment. A pharmaceutical activity can also include at least one of drug design, drug synthesis, drug formulation, drug characterization, drug screen and assay, clinical evaluation, and drug purification. In a more preferred embodiment, the drug synthesis can include distillation, screening, crystallization, filtration, washing, or drying.

In particular, the terms "drug design", as used herein, has the meaning commonly afforded the term in the art. Drug design can include the approach of finding drugs by design, based on their biological targets. Typically, a drug target is a key molecule involved in a particular metabolic or signaling pathway that is specific to a disease condition or pathology, or to the infectivity or survival of a microbial pathogen. The term "drug characterization", as used herein, also has the meaning commonly afforded the term in the art. The meaning can include a wide range of analyses to obtain identity, purity, and stability data for new drug substances and formulations, including: structural identity and confirmation, certificates of analyses, purity determinations, stability-indicating methods development and validation identification and quantification of impurities, and residual solvent analyses.

In some embodiments, the pharmaceutical activity can include studies on a molecular interaction within the mixture. The term "study", used herein, can include an endeavor for acquiring knowledge about a given subject through, for example, an experiment, (i.e. clinical trial). In a preferred embodiment, examples of the studies can include one or more of pharmacokinetics, pharmacodynamics, solvent screening, combination drug therapy, drug toxicity, a process design for an active pharmaceutical ingredient, and chromatography. The cited types of study have the meaning commonly afforded the term in the art.

In further embodiments, the methods of conducting a pharmaceutical activity can comprise the mixture that includes at least one liquid phase. In one embodiment, the methods can include any number and combination of vapor, solid and liquid phases. In another embodiment, the methods include at least one liquid phase and at least one solid phase. In a preferred embodiment, the mixture can include at least one liquid solvent and at least one pharmaceutical component. In a more preferred embodiment, the mixture can include more than one phase and at least a portion of the at least one pharmaceutical component. The pharmaceutical component can be an active pharmaceutical ingredient.

The liquid phase can be an amorphous phase. The term "an amorphous phase" used herein, has the meaning commonly afforded the term in the art. An amorphous phase can include a solid in which there is no long-range order of the positions of the atoms. (Solids in which there is long-range atomic order are called crystalline solids.) Most classes of solid materials can be found or prepared in an amorphous form. For instance, common window glass is an amorphous ceramic, many polymers (such as polystyrene) are amorphous, and even foods such as cotton candy are amorphous phase. Amorphous materials are often prepared by rapidly cooling molten material. The cooling reduces the mobility of the material's molecules before they can pack into a more thermodynamically favorable crystalline state. Amorphous materials can also be produced by additives which interfere with the ability of the primary constituent to crystallize. For example addition of soda to silicon dioxide results in window glass and the addition of glycols to water results in a vitrified solid. In a preferred embodiment, at least one of the species in the mixture that is in the amorphous phase is an active pharmaceutical ingredient. In a more preferred embodiment, the method can include a step of estimating an amorphous phase solubility by calculating a phase equilibrium between a solute rich phase and a solvent rich phase.

In some embodiments, the methods of conducting a pharmaceutical activity can include a mixture that has at least one of the at least two chemical species is a pharmaceutical component. In a preferred embodiment, the pharmaceutical component is an active pharmaceutical ingredient.

In some embodiments, the methods of conducting a pharmaceutical activity can further comprise the steps of: (a) using the determined conceptual segments, computing at least one physical property of the mixture; and (b) providing an analysis of the computed physical property. The analysis forms a model of the at least one physical property of the mixture. In a preferred embodiment, the step of defining an identity can include steps of identifying each conceptual segment as one of a hydrophobic segment, a hydrophilic segment, a polar segment, or a solvation segment.

In some embodiments, the methods of conducting a pharmaceutical activity can comprise a mixture of at least two chemical species that includes at least one electrolyte. In further embodiments, the methods further include the steps of: a) using the determined conceptual electrolyte segment, computing at least one physical property of the mixture; and b) providing an analysis of the computed physical property. The analysis forms a model of the at least one physical property of the mixture. In one embodiment, the step of computing at least one physical property can include steps of calculating the activity coefficient of the ionic species derived from the electrolyte. In a preferred embodiment, the computed physical property of the analysis can include at least one of activity coefficient, vapor pressure, solubility, boiling point, freezing point, octanol/water partition coefficient, and lipophilicity of the electrolyte.

In further embodiment, the conceptual electrolyte segment can include a cationic segment and an anionic segment, both segments of unity of charge.

In some embodiment, the electrolyte is any one of: a pharmaceutical compound, a nonpolymeric compound, a polymer, an oligomer, an inorganic compound and an organic compound. In one embodiment, the electrolyte is symmetrical or unsymmetrical. In another embodiment, the electrolyte is univalent or multivalent. In yet another embodiment, the electrolyte includes two or more ionic species.

In some embodiments, the present invention features methods of separating one or more chemical species from a mixture. The methods include steps of modeling molecular interaction between the chemical species in one or more solvents by determining at least one conceptual segment for each of the species, including defining an identity and an equivalent number of each conceptual segment.

In further embodiments, the methods of separating one or more chemical species from a mixture can use chromatography. In a preferred embodiment, the types of chromatography can include one of the following: capillary-action chromatography, paper chromatography, thin layer chromatography, column chromatography, fast protein liquid chromatography, high performance liquid chromatography, ion exchange chromatography, affinity chromatography, gas chromatography, and countercurrent chromatography. In a more preferred embodiment, the chromatography is high performance liquid chromatography.

In one embodiment, the methods of separating one or more chemical species can comprise a mixture that includes at least one liquid phase. In another embodiment, the method of separating one or more chemical species can comprise a mixture that includes at least one liquid phase and that at least a portion of at least one chemical species is in the liquid phase. In yet anther embodiment, at least one of the chemical species of the method of separating one or more chemical species is an active pharmaceutical ingredient.

In some embodiments, the methods of separating one or more chemical species can include the steps of: a) using the determined conceptual segments, computing at least one physical property of the mixture; and b) providing an analysis of the computed physical property. The analysis forms a model of the at least one physical property of the mixture. In further embodiments, the steps of defining an identity can include steps of identifying each conceptual segment as one of a hydrophobic segment, a hydrophilic segment, a polar segment, or a solvation segment.

In some embodiments, this invention features computer program products. The computer program products comprise a computer usable medium and a set of computer program instructions embodied on the computer useable medium for conducting industrial manufacture, research or development by modeling at least one physical property of a mixture of at least two chemical species by determining at least one conceptual segment for each of the chemical species. Included are instructions to define an identity and an equivalent number of each of conceptual segment. In a preferred embodiment, the computer usable medium can include a removable storage medium. In a more preferred embodiment, the removable storage medium can include any of a CD-ROM, a DVD-ROM, a diskette, and a tape.

In further embodiment, the computer program products can include: (a) instructions to use the determined conceptual segments to compute at least one physical property of the chemical mixture; and (b) instructions to provide an analysis of the computed physical property. The analysis forms a model of at least one physical property of the mixture.

In one embodiment of the computer program products, at least some portion of the computer program instructions can include instructions to request data or request instructions over a telecommunications network. In another embodiment, at least some portion of the computer program is transmitted over a global network.

In another embodiment of the computer program products, an industrial manufacture, research or development can include a pharmaceutical activity. In a preferred embodiment, the pharmaceutical activity can include one or more of the following: pharmacokinetics, pharmacodynamics, solvent screening, crystallization productivity, drug formulation, combination drug therapy, drug toxicity, a process design for an active pharmaceutical ingredient, capillary-action chromatography, paper chromatography, thin layer chromatography, column chromatography, fast protein liquid chromatography, high performance liquid chromatography, ion exchange chromatography, affinity chromatography, gas chromatography, and countercurrent chromatography.

In some embodiment, the invention features computer systems for conducting industrial manufacture, research or development by modeling at least one physical property of a mixture of at least two chemical species. The computer systems can include: a) a user input means for obtaining chemical data from a user; b) a digital processor coupled to receive obtained chemical data input from the input means; and c) an output means coupled to the digital processor. The digital processor executes a modeling system in working memory, and the output means provides to the user the formed model of the physical property of the mixture. The modeling system may use the chemical data to determine at least one conceptual segment for each of the chemical species, including defining an identity and equivalent number of each conceptual segment.

In further embodiments, the computer system can: a) use the determined conceptual electrolyte segment to compute at least one physical property of the mixture; and b) provide an analysis of the computed physical property. The analysis forms a model of at least one physical property of the mixture. In a preferred embodiment, the computer system can enable transmission of some portion of at least one of the chemical data and the formed model over a global network. Alternatively, the computer system can also conduct industrial manufacture, research or development that includes a pharmaceutical activity. In a preferred embodiment, conducting industrial manufacture, research or development can include one or more of the following: pharmacokinetics, pharmacodynamics, solvent screening, crystallization productivity, drug formulation, combination drug therapy, drug toxicity, a process design for an active pharmaceutical ingredient. capillary-action chromatography, paper chromatography, thin layer chromatography, column chromatography, fast protein liquid chromatography, high performance liquid chromatography, ion exchange chromatography, affinity chromatography, gas chromatography, and countercurrent chromatography.

Reference is now made to a preferred embodiment of the present invention as illustrated in FIGS. 1-4. FIG. 1 illustrates a computer network or similar digital processing environment in which the present invention may be implemented.

Referring to FIG. 1, client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 2:
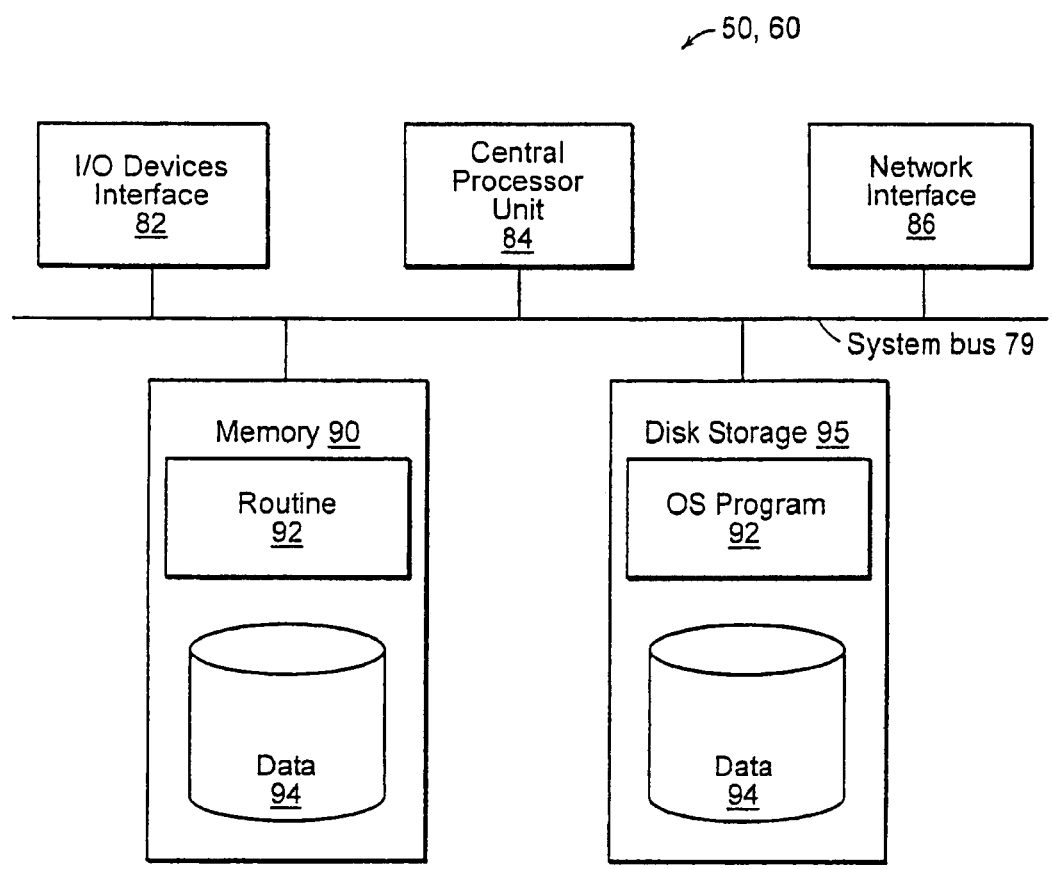
FIG. 2 is a block diagram of a computer of the network of FIG. 1.

FIG. 2 is a diagram of the internal structure of a computer (e.g., client processor/device 50 or server computers 60) in the computer system of FIG. 1. Each computer 50, 60 contains system bus 79, where a bus is a set of hardware lines used for data transfer among the components of a computer or processing system. Bus 79 is a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 1). Memory 90 provides volatile storage for computer software instructions 92 and data 94 used to implement an embodiment of the present invention (e.g., NRTL-SAC and eNRTL-SAC in FIGS. 3-4). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92 or 20), including a computer readable medium (e.g., a removable storage medium such as one or more DVD-ROM's, CD-ROM's, diskettes, tapes, etc.) that provides at least a portion of the software instructions for the invention system 20. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 (e.g., NRTL-SAC or eNRTL-SAC) is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

Figure 3:
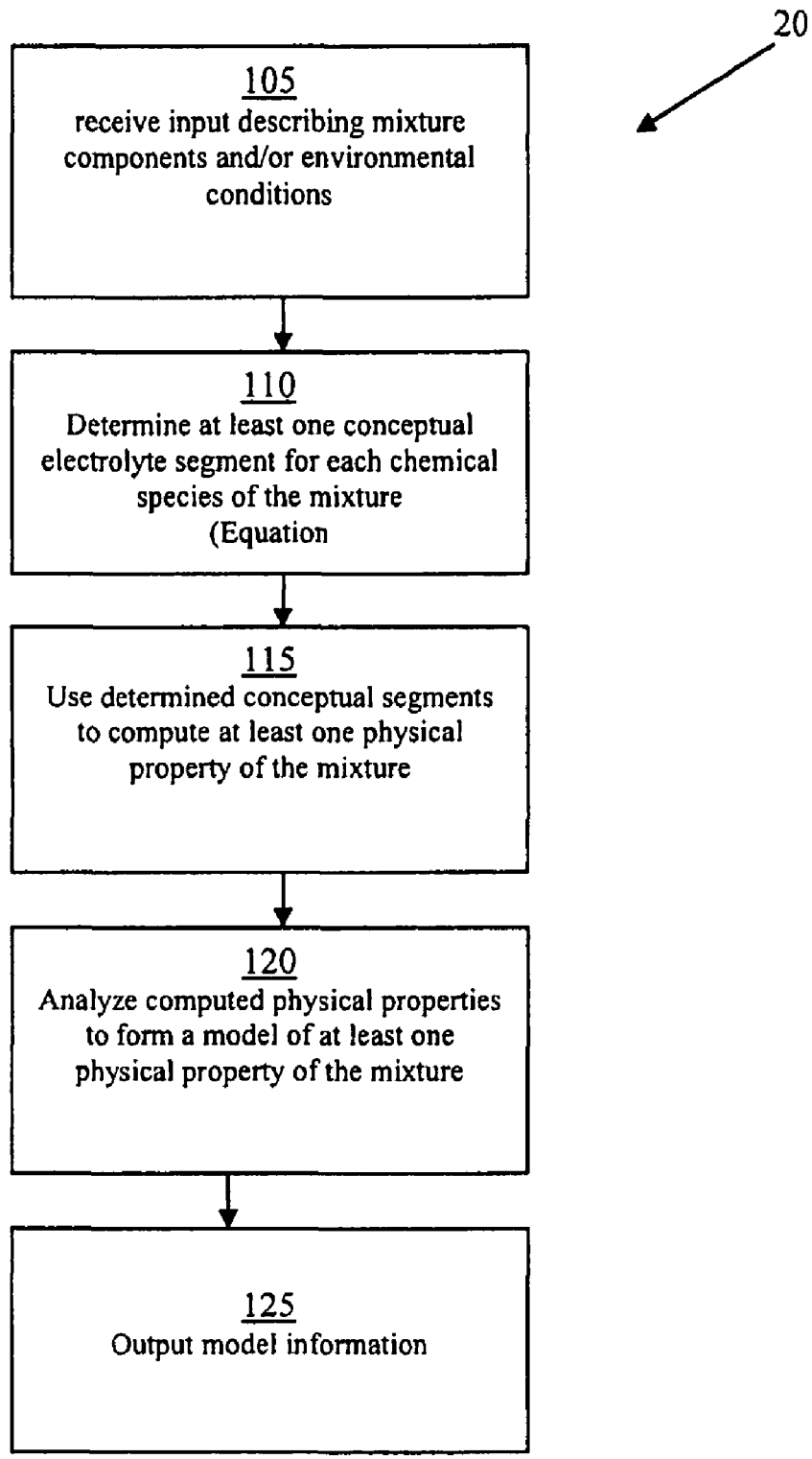
FIGS. 3-4b are flow diagrams of one embodiment of the present invention employed in the computer network environment of FIGS. 1 and 2.

FIGS. 3 and 4 illustrate data flow and process steps for a model 20 (the model 20 refers to the present invention in context of both NRTL-SAC and eNRTL-SAC models.) performing the methods of the present invention. With reference to FIG. 3, chemical data describing one or more chemical species (e.g., an electrolyte and solvent) of the mixture and/or environmental conditions (e.g., pressure and/or temperature) is entered at step 105 of the modeler process. Step 110 uses that data to determine at least one conceptual segment including a conceptual segment (for nonelectrolytes) or a conceptual electrolyte segment (for electrolytes) for each of the chemical species of the mixture. The determined conceptual segment or electrolyte conceptual segment and other determined conceptual segments are used to compute at least one physical property of the mixture during step 115. The computed physical properties are analyzed to form a model of at least one physical property of the mixture (e.g., solubility of one or more chemical species in one or more phases of the mixture) in step 120. The model information is then given as output at step 125. The output can take the form of data or an analysis appearing on a computer monitor, data or instructions sent to a process control system or device, data entered into a data storage device, and/or data or instructions relayed to additional computer systems or programs.

Figure 4A:
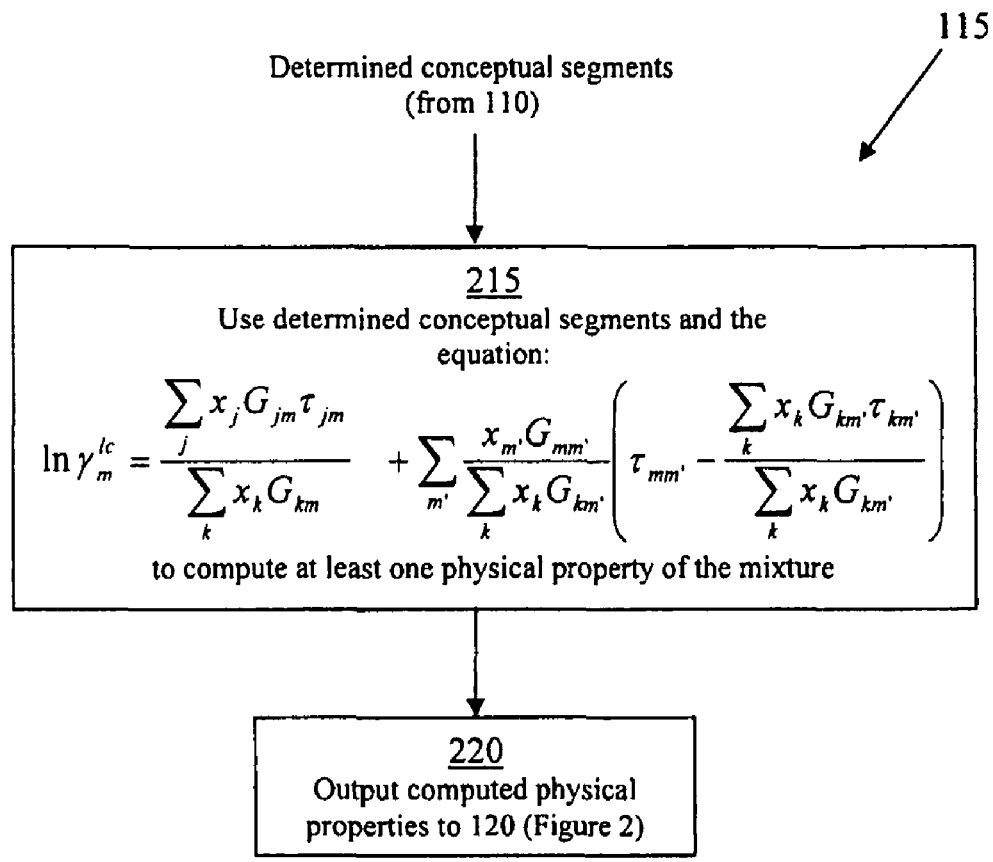
Figure 4B:
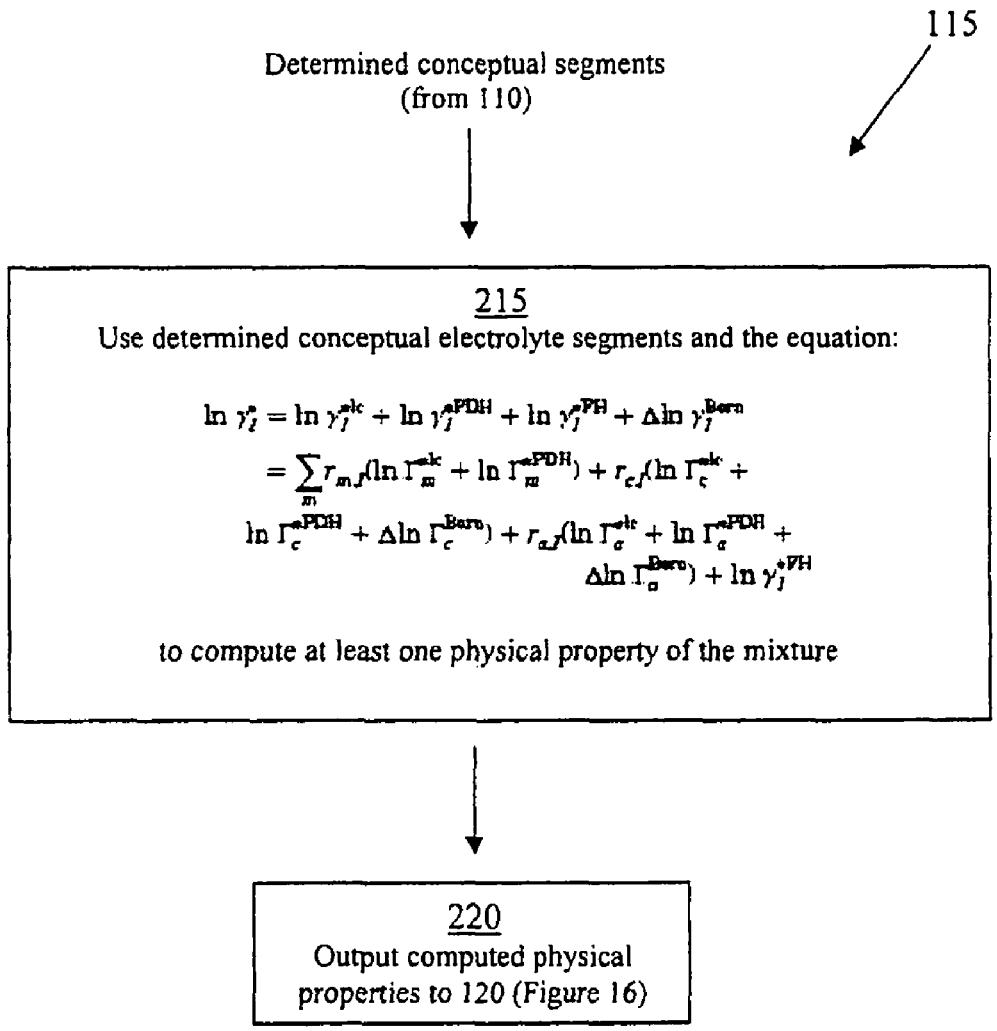

FIGS. 4a and 4b illustrate in more detail the computation at step 115 in FIG. 3. Step 115 begins with the receipt of determined conceptual electrolyte and other segments for each of the chemical species (e.g., nonelectrolytes, electrolyte, solvent, etc.) of the mixture. The determined conceptual segments and the equation:

$$\ln\gamma_m^{lc} = \frac{\sum_j x_j G_{jm}\tau_{jm}}{\sum_k x_k G_{km}} + \sum_{m'} \frac{x_{m'} G_{mm'}}{\sum_k x_k G_{km'}} \left( \tau_{mm'} - \frac{\sum_k x_k G_{km'}\tau_{km'}}{\sum_k x_k G_{km'}} \right) \quad (1)$$

are used to compute at least one physical property of the mixture during step 215 in FIG. 4a. As for the determined conceptual electrolyte and other segments shown in FIG. 4b, the equation:

$$\ln\gamma_I^* = \ln\gamma_I^{*lc} + \ln\gamma_I^{*PDH} + \ln\gamma_I^{*FH} + \Delta\ln\gamma_I^{Born} \quad (2)$$

$$= \sum_m r_{m,I}(\ln\Gamma_m^{*lc} + \ln\Gamma_m^{*PDH}) + r_{c,I}(\ln\Gamma_c^{*lc} + \ln\Gamma_c^{*PDH} + \Delta\ln\Gamma_c^{Born}) +$$

$$r_{a,I}(\ln\Gamma_a^{*lc} + \ln\Gamma_a^{*PDH} + \Delta\ln\Gamma_a^{Born}) + \ln\gamma_I^{*FH}$$

are used to compute at least one physical property of the mixture during step 215. The computed physical properties are provided as output 220 from computation step 215. In step 220, the computed physical properties are passed to step 120 of FIG. 16 for forming a model of the physical property of the mixture as described above.

Chromatography Applications of the Present Invention

The term "chemical species" refers to atoms, molecules, molecular fragments, ions, solutes, solvents, and others, as entities being subjected to a chemical process or to a measurement.

The term "molecular descriptor" used herein is the result of a logic and mathematical model procedure which transforms intrinsic chemical information encoded within a molecule or expressed as results of some standardized experiments into certain symbolic representation for the purpose of correlation, prediction or analysis. One example of "molecular descriptor" is, in addition to the scope and the content thereof described earlier, conceptual segments, which is based on expressed characteristics of molecular interactions between chemical species (e.g., a specie in a solute interacting with the surface of the stationary phase.). In certain embodiments, conceptual segments describe for each solute and solvent molecule their effective surface interaction in terms of the following types of the conceptual segments: hydrophobic segment, polar segment, hydrophilic segment, and solvation segment or a combination thereof. The conceptual segments are to simulate the interaction characteristics of representative molecular surfaces. For example, the hydrophilic segment simulates polar molecular surfaces that are "hydrogen bond donor or acceptor." As such, it represents molecular surfaces with the tendency to form a hydrogen bond. Conversely, the hydrophobic segment simulates molecular surfaces with the adversity to form a hydrogen bond. As for the polar segment, it simulates polar molecular surfaces that are "electron pair donor or acceptor." With the conceptual segments identified, real chemical species are then selected as reference chemical species for the conceptual segments and available phase equilibrium data of these reference chemical species are used to identify molecular interaction energy parameters for the conceptual segments. The reference chemical species with distinct molecular characteristics (i.e., hydrophobic, hydrophilic, polar, or solvation) and with abundant, publicly available phase equilibrium data are chosen for practical purposes.

The methods disclosed herein have chemical and industrial applications such as for manufacture of a drug. One of the applications is in the area of chromatography, which has become the premier technique for separations and analyses. Most separation methods in chromatography employ two phases, the stationary phase and the mobile phase. The mobile phase can include one or more solvents; and in the mobile phase, one or more solutes or chemical species are dissolved in the one or more solvents of the mobile phase to be separated by a chromatographic technique. The one or more chemical species can include a pharmaceutically active ingredient such as a small molecule like pharmaceutical drug molecules (e.g., organic molecules having molecular weight less than about 1000 D, a peptide or a DNA molecule). Conversely, the stationary phase is the part of the chromatographic system through which the mobile phase flows where distribution of the solutes between the phases occurs. The stationary phase may be a solid or a liquid that is immobilized or adsorbed on a solid.

One embodiment of the present invention related to chromatography is methods of conducting chromatography for separating one or more chemical species from a mixture. The methods include:
 assigning molecular descriptors based on molecular interaction characteristics to each of: (i) the one or more species, (ii) a mobile phase component, and (iii) a stationary phase component;
 measuring respective molecular interaction indices for the one or more species, for the mobile phase component and for the stationary phase component, and
 determining respective activity coefficients of: (i) the one or more species; (ii) the mobile phase component; and (iii) the stationary phase component, such that the determined respective activity coefficients enables conducting chromatography for separating the one or more species from the mixture.

In certain embodiments, the method can further include separating the one or more chemical species from the mixture. The word "separation" or "separating" used herein is the hypothetical condition where there is complete isolation, by distinct chromatograpic peaks, of each of the x chemical species, which comprises a mixture. It should be understood that the adjective "hypothetical" in the definition of "separation" or "separating" above is used because: (1) it is theoretically impossible to accomplish the complete separation of the species of a mixture; and/or (2) the separated components in the present invention do not require to be actually isolated into vessels but rather are detected and their presence recorded (e.g., on chart paper or in a computer data file).

The term "component" used in the "stationary phase component" or "mobile phase component" refers the composition that make up each of the mobile phase and the stationary phase associated with a chromatography reaction. The composition can include one or more distinct chemical species. For example, the mobile phase component can include one or more solvents. Conversely, the stationary phase component can include one or more solvents and/or one or more interacting surface areas. The one or more interacting surface areas referred herein can be a portion of the substance(s), which is fixed in place for the chromatography procedure that are exposed to the solvents and/or the chemical species in the mixture.

The terms "molecular interaction energy indices" refer to measurement of the effective surface areas of the chemical species that exhibit surface interaction characteristics. An example of such molecular interaction energy indices is equivalent numbers. These equivalent numbers are to be determined not from the molecular structure of given chemical species but from the interaction characteristics of the chemical species in a mixture as expressed in their experimental phase equilibrium data.

In certain embodiments of the present invention, the one or more predetermined molecular descriptors are based on surface molecular interaction characteristics. The term "molecular interaction characteristics" referred herein are to be determined not from the molecular structure but from the interaction characteristics of the chemical specie in solution as expressed in their experimental phase equilibrium. Each of these molecular interaction characteristics can be represented by a conceptual segment as defined above.

The identities of conceptual segments for chemical species can include at least one conceptual segment (e.g., at least 1, 2, 3, 4, 5, 6, 7, 8, 9, 10, 11, 12 or more than 12 conceptual segments) such as hydrophobic segment, polar segment, hydrophilic segment, solvation segment or a combination thereof. Additional conceptual segments may be introduced depending on the scope of the different type of chemical species involved such as organic electrolytes, charged molecules, zwitterions, etc. In certain embodiments, the choice of conceptual segments can be a minimal set rather than a comprehensive set. These conceptual segments are chosen to simulate the interaction characteristics of representative molecular surfaces that significantly contribute to the liquid-phase nonideality of real molecules. For example, the hydrophilic segment simulates polar molecular surfaces that are "hydrogen bond donor or acceptor." As such, it represents molecular surfaces with the tendency to form a hydrogen bond. The hydrophobic segment simulates molecular surfaces with the adversity to form a hydrogen bond. The polar segment simulates polar molecular surfaces that are "electron pair donor or acceptor." In certain embodiments, the polar conceptual segment can include other non-hydrophobic and non-hydrophilic surface interactions.

Table 1 shows 62 chemical species and their molecular characteristics. As indicated by Table 1, hydrocarbon solvents (aliphatic or aromatic), halogenated hydrocarbons, and ethers are mainly hydrophobic. Ketones, esters, and amides are both hydrophobic and polar. Alcohols, glycols, and amines may have both substantial hydrophilicity and hydrophobicity. Acids are "complex" molecules, exhibiting hydrophilicity, polarity, and hydrophobicity.

In certain embodiments, the step of measuring respective molecular interaction indices for the one or more chemical species, for the mobile phase component and for the stationary phase component includes determining the molecular interaction indices based on measures of effective surface areas expressing surface molecular interaction characteristics for each of the one or more species, of the mobile phase component, and of the stationary phase component.

In certain embodiments, the step of assigning molecular descriptors based on molecular interaction characteristics to each of: (i) the one or more species, (ii) a mobile phase component, and (iii) a stationary phase component includes assigning one or more predetermined conceptual segments to each of the one or more species, of the mobile phase component and of the stationary phase component.

In certain embodiments, the method further includes determining molecular interaction energy indices associated with each of the predetermined conceptual segments.

In certain embodiments, the step of assigning one or more predetermined conceptual segments to each of the one or more species, of the mobile phase component and of the stationary phase component includes identifying respective pairwise segment-segment interaction parameters for each of the predetermined conceptual segments. In certain embodiment, the respective pairwise segment-segment interaction parameters are binary quantities such as binary NRTL parameters. The method further defines conceptual segments that broadly characterize surface interaction characteristics of chemical species, including molecules, solvents or solutes. These conceptual segments, together with their corresponding nonrandomness factor and segment-segment binary interaction energy parameters, are capable of qualitatively describing interactions between different chemical species, including the various solvent-solvent, solvent-solute and solute-solute molecular interactions and the phase behavior of solvents and solutes. In certain embodiments, the method describes the molecular surface interactions of all solvents and solutes in solution with different types of conceptual segments such as: hydrophobic segment, solvation segment, polar segment, hydrophilic segment or a combination thereof. The equivalent numbers for each chemical species are measurement of the effective molecular surface areas that exhibit surface interaction characteristics of hydrophobicity, solvation, polarity, hydrophilicity or a combination thereof. For example, hydrophilic segment simulates molecular surfaces that are "hydrogen bond donor or acceptor". The hydrophobic segment simulates molecular surfaces that show aversion to forming a hydrogen bond. The polar and solvation segments simulate molecular surfaces that are "electron pair donor or acceptor." The solvation segment is attractive to hydrophilic segment while the polar segment is repulsive to hydrophilic segment.

In certain embodiments, the equivalent numbers for each of the predetermined conceptual segments of the chemical species are determined in comparison to reference chemical species from regression of available experimental equilibrium data associated with these reference chemical species. In certain embodiment, available phase equilibrium data of these reference chemical species are used to identify NRTL binary parameters for the respective conceptual segments. Chemical species with distinct molecular characteristics (i.e., hydrophobic, hydrophilic, or polar) and with publicly available phase equilibrium data are chosen as the reference chemical species.

For example, to determine the conceptual segment numbers of a solute molecule, solubility data in at least four solvents of varied surface interaction characteristics are chosen. Alternatively, infinite dilution activity coefficient data of the solute in at least four solvents of varied surface interaction characteristics can be used. The parameterization is improved if a range of hydrophilic solvents, polar solvents, solvation solvents and hydrophobic solvents are used. Once the segment numbers of the solute molecule are determined, the methods disclosed herein can then reliably predict solute activity coefficients and resulting phase behavior in other pure solvents or solvent mixtures. This conceptual segment methodology disclosed herein can also be extended for modeling activity coefficients of other chemical species.

In certain embodiments, the step of assigning one or more predetermined conceptual segments to each of the one or more species, of the mobile phase component and of the stationary phase component includes describing the molecular interactive characteristics in terms of a hydrophobic segment, a polar segment, a solvation segment, a hydrophilic segment or a combination thereof.

In certain embodiments, measuring respective molecular interaction indices for the one or more chemical species, and the mobile phase component and the stationary phase component includes determining an equivalent number for the predetermined conceptual segment.

In certain embodiments, determining respective activity coefficients of: (i) the one or more species; (ii) the mobile phase component; and (iii) the stationary phase component includes using the following formula:

$$\ln \gamma_I = \ln \gamma_I^C + \ln \gamma_I^R, \quad (3)$$

wherein:
$\gamma_I$ is an activity coefficient for the one or more species, for the mobile phase component or for the stationary phase component;
$\gamma_I^C$ is a combinatorial contribution to the activity coefficient for the one or more species, for the mobile phase component or for the stationary phase component; and
$\gamma_I^R$ is a residual contribution to the activity coefficient of the one or more species, for the mobile phase component or for the stationary phase component.

In certain embodiment, determining respective activity coefficients of: (i) the one or more species; (ii) the mobile phase component; and (iii) the stationary phase component further includes the following formulas for computing respective activity coefficients:

$$\ln \gamma_I^R = \ln \gamma_I^{lc} = \sum_m r_{m,I} [\ln \Gamma_m^{lc} - \ln \Gamma_m^{lc}], \quad (4)$$

$$\ln \Gamma_m^{lc} = \frac{\sum_j x_j G_{jm} \tau_{jm}}{\sum_k x_k G_{km}} + \sum_{m'} \frac{x_{m'} G_{mm'}}{\sum_k x_k G_{km'}} \left( \tau_{mm'} - \frac{\sum_j x_j G_{jm'} \tau_{jm'}}{\sum_k x_k G_{km'}} \right), \text{ and}$$

$$\ln \Gamma_{m,I}^{lc} = \frac{\sum_j x_{j,I} G_{jm} \tau_{jm}}{\sum_k x_{k,I} G_{km}} + \sum_{m'} \frac{x_{m',I} G_{mm'}}{\sum_k x_{k,I} G_{km'}} \left( \tau_{mm'} - \frac{\sum_j x_{j,I} G_{jm'} \tau_{jm'}}{\sum_k x_{k,I} G_{km'}} \right),$$

wherein:
I is a component index for the one or more species, the mobile phase component, or the stationary phase component;
each j, k, m, and m' is a segment species index;
$x_j$ is a segment-based mole fraction of segment species j;
$x_{j,I}$ is a segment-based mole fraction of segment species j in I;
$r_{m,I}$ is an equivalent number of segment species m contained only in I;
$\Gamma_m^{lc}$ is an activity coefficient of segment species m;
$\Gamma_m^{lc,I}$ is an activity coefficient of segment species m contained in I; and
G and $\tau$ are binary quantities related to each other by a non-random factor parameter $\alpha$ as in $G=\exp(-\alpha\tau)$.

In certain embodiments, the method of conducting chromatography for separating one or more species from a mixture further includes calculating respective retention times of the one or more chemical species based on the respective activity coefficients of: (i) the one or more species; (ii) the mobile phase component: and (iii) the stationary phase component. In certain embodiments, calculating respective retention times of the one or more chemical species includes computing a capacity ratio for each of the one or more chemical species. The capacity ratio is a function of the molecular interaction: a) between the one or more species and a mobile phase component; and b) between the one or more species and a stationary phase component.

In certain embodiments, computing the capacity ratio includes using the following formulas:

$$k_I = \frac{t_{rI} - t_0}{t_0}, \text{ and} \quad (5)$$

$$k_I = \frac{x_s V_s}{x_m V_m} = K_I \Phi,$$

wherein:
$k_I$ is a capacity ratio of the one or more species;
$t_{rI}$ is a retention time of the one or more species;
$t_0$ is an elution time for an inert tracer;
$K_I$ is a partition coefficient;
$\Phi$ is a phase ratio;
$V_s$ is a volume of the stationary phase component;
$V_m$ is a volume of the mobile phase component;
$x_s$ is a concentration of the one or more species interacting with the stationary phase component; and
$x_m$ is a concentration of the one or more species interacting with the mobile phase component.

In certain embodiment, computing the capacity ratio includes further includes computing the partition coefficient $K_I$ using the following formula:

$$K_I = \frac{\gamma_m^\infty}{\gamma_s^\infty}, \quad (6)$$

wherein:
$\gamma_m^\infty$ and $\gamma_s^\infty$ the mobile phase and the stationary phase activity coefficients of the one or more chemical species at infinite dilution;

In certain embodiments, the method of conducting chromatography for separating a one or more species from a mixture further includes selecting independently a composition of the mobile phase component, a composition of the stationary phase component and a temperature for separating a desired species from the mixture.

One embodiment of the present invention is a method of conducting chromatography. The method includes:
controlling a retention time of one or more species in a mixture by determining at least one conceptual segment of: a) the one or more species, b) a mobile phase component, and c) a stationary phase component; and
defining an identity and an equivalent number of each of the at least one conceptual segment.

In certain embodiments, the method further includes separating the one or more species from the mixture.

In certain embodiments, the one or more chemical species is an active pharmaceutical ingredient.

In certain embodiments, the mobile phase component includes one or more solvents.

In certain embodiments, the stationary component includes one or more solvents and interacting surface areas.

In certain embodiments, the at least one conceptual segment is a molecular descriptor to represent a molecular interaction characteristic of; a) the one or more species, b) the mobile phase component, and c) the stationary phase component. In certain embodiments, the molecular interaction characteristic is a molecular surface interaction characteristic of a) the one or more species, b) the mobile phase component, and c) the stationary phase component.

In certain embodiments, the conceptual segment includes a hydrophobic segment, a polar segment, a hydrophilic segment, or a solvation segment.

In certain embodiments, controlling a retention time of one or more species in a mixture includes computing at least one physical property for each of the one or more species, the mobile phase component and the stationary phase component, the at least one physical property computed using the determined at least one conceptual segment and the equivalent number. In certain embodiments, the at least one physical property is an activity coefficient for each of the one or more species, the mobile phase component and the stationary phase component. In certain embodiments, computing each of the activity coefficient for the one or more species, for the mobile phase component and for the stationary phase component includes selecting a plurality of real molecules as reference molecules, each of the reference molecules having at least one conceptual segment and an equivalent number. In general, the reference molecules are molecules with: (a) publicly available equilibrium data; and/or (2) particular molecular characters. Molecular characters can include hydrophobicity, hydrophilicity, salvation, polarity or a combination thereof. For example, hydrocarbon solvents (aliphatic or aromatic), halogenated hydrocarbons, and ethers are mainly hydrophobic. Conversely, a molecule can exhibit more than one molecular character. Ketones, esters, and amides are both hydrophobic and polar. Alcohols, glycols, and amines may have both substantial hydrophilicity and hydrophobicity. Acids are "complex" molecules, exhibiting hydrophilicity, polarity, and hydrophobicity.

In certain embodiments, computing each of the activity coefficient for interaction of the one or more chemical species, the mobile phase component and the stationary phase component further includes identifying the equivalent numbers for the one or more species, for the mobile phase component, and for the stationary phase component, with respect to the reference molecules.

In certain embodiments, computing each of the activity coefficient for the one or more chemical species, the mobile phase component and the stationary phase component includes providing data regarding partition characteristics of the reference molecules in a chromatography separation. In certain embodiments, computing each of the activity coefficient for the one or more chemical species, the mobile phase component and the stationary phase component further includes determining partition characteristics of the one or more species with respect to the partition characteristics of the reference molecules. The data regarding partition characteristics of the reference molecules in a chromatography separation referred in these embodiments is partition coefficient data or retention factor data.

In certain embodiments, the method of conducting chromatography further includes determining molecular interaction energy indices associated with each of the conceptual segments. As previously addressed, an example of the molecular interaction energy indices is binary NRTL parameters.

In certain embodiments, the method of conducting chromatography further includes further computing activity coefficients of the one or more species, the mobile phase component and the stationary phase component.

In certain embodiments, computing the activity coefficient of the one or more species, the mobile phase component or the stationary phase component uses the following formulae:

$$\ln \gamma_I = \ln \gamma_I^C + \ln \gamma_I^R, \qquad (7)$$

wherein:

$\gamma_I$ is an activity coefficient for the one or more species, the mobile phase component or the stationary phase component;

$\gamma_I^C$ is a combinatorial contribution to the activity coefficient for the one or more species, the mobile phase component or the stationary phase component; and $\gamma_I^R$ is a residual contribution to the activity coefficient of the one or more species, the mobile phase component or the stationary component.

In certain embodiments, computing the activity coefficient of the one or more species, the mobile phase component or the stationary phase component includes computing the following formulas:

$$\ln \gamma_I^R = \ln \gamma_I^{lc} = \sum_m r_{m,I}[\ln \Gamma_m^{lc} - \ln \Gamma_{m,I}^{lc}], \qquad (8)$$

$$\ln \Gamma_m^{lc} = \frac{\sum_j x_j G_{jm} \tau_{jm}}{\sum_k x_k G_{km}} + \sum_{m'} \frac{x_{m'} G_{mm'}}{\sum_k x_k G_{km'}} \left( \tau_{mm'} - \frac{\sum_j x_j G_{jm'} \tau_{jm'}}{\sum_k x_k G_{km'}} \right), \text{ and}$$

$$\ln \Gamma_{m,I}^{lc} = \frac{\sum_j x_{j,I} G_{jm} \tau_{jm}}{\sum_k x_{k,I} G_{km}} + \sum_{m'} \frac{x_{m',I} G_{mm'}}{\sum_k x_{k,I} G_{km'}} \left( \tau_{mm'} - \frac{\sum_j x_{j,I} G_{jm'} \tau_{jm'}}{\sum_k x_{k,I} G_{km'}} \right),$$

wherein:

I is a component index for the one or more species, the mobile phase component, or the stationary phase component;

each j, k, m, and m is a segment species index;

$x_j$ is a segment-based mole fraction of segment species j;

$x_{j,I}$ is a segment-based mole fraction of segment species j in the I;

$r_{m,I}$ is a number of segment species m contained only in the I;

$\Gamma_m^{lc}$ is an activity coefficient of segment species m;

$\Gamma_m^{lc,I}$ is an activity coefficient of segment species m contained in the I; and G and $\tau$ are binary quantities related to each other by a non-random factor parameter $\alpha$ as in $G = \exp(-\alpha \tau)$.

In certain embodiments, controlling a retention time of the one or more species includes calculating the retention time of the one or more species. In certain embodiments, calculating the retention time of the one or more species includes computing a capacity ratio of the one or more species.

A certain embodiment of the present invention is a computer program product. The computer program product includes:

a) a computer usable medium; and b) a set of computer program instructions embodied on the computer usable medium for conducting chromatography for separating a one or more chemical species from a mixture by:
1) assigning molecular descriptors based on molecular interaction characteristics to each of: (i) the one or more species, (ii) a mobile phase component, and (iii) a stationary phase component;
2) measuring respective molecular interaction indices for the one or more species, for the mobile phase component and for the stationary phase component; and
3) determining respective activity coefficients of: (i) the one or more species; (ii) the mobile phase component; and (iii) the stationary phase component, such that the determined respective activity coefficients enables conducting chromatography for separating the one or more species from the mixture.

In certain embodiments, at least some portion of the computer program can be transmitted over a global network. In certain embodiments, the computer usable medium can include a removable storage medium. The removal storage medium can include a CD-ROM, a DVD-ROM, a diskette, a tape or a combination thereof.

In certain embodiments, the one or more chemical species includes an active pharmaceutical ingredient.

In certain embodiments, the set of computer program instructions embodied on the computer usable medium for conducting chromatography for separating one or more chemical species from a mixture can include an additional step of computing at least one physical property for each of the one or more species, for the mobile phase component and for the stationary phase component using the determined at least one conceptual segment.

In certain embodiments, the set of computer program instructions embodied on the computer usable medium for conducting chromatography for separating one or more chemical species from a mixture can include an additional step of selecting independently a solvent composition of the mobile phase component, the stationary phase component and a temperature for separating a desired species from the mixture.

A certain embodiment of the present invention is a computer system for conducting chromatography. The computer system for conducting chromatography includes:
a) a user input means for obtaining empirical data from a user;
b) a digital processor coupled to receive the empirical data from the input means, wherein the digital processor executes a modeling system in working memory, wherein the modeling system uses the empirical data for:
1) assigning molecular descriptors based on molecular interaction characteristics to each of: (i) each of the one or more species; (ii) a mobile phase component; and (iii) a stationary phase component;
2) measuring respective molecular interactive indices for the one or more species, and the mobile phase component and for the stationary phase component; and
3) determining activity coefficients of: (i) the one or more species; (ii) the mobile phase component; and (iii) the stationary phase component such that the determined respective activity coefficients enables conducting chromatography for separating the one or more species from the mixture.

In a certain embodiment, the computer system for conducting chromatography can further include an output means coupled to the digital processor. The output means provides to the user indications of selecting the mobile phase, and the stationary phase and, optionally, a reaction temperature for the one or more species from the modeling system.

In certain embodiments, the computer system enables transmission of some portion of the empirical data and results from the modeling system over a global network.

It should be understood that the method of conducting chromatography disclosed herein can be applied to any type of chromatographic techniques. Examples of techniques include any one of: gas-liquid, gas-solid, supercritical fluid, liquid-liquid, thin layer, liquid solid, ion-exchange, size-excursion, affinity, bonded phase, capillary electrochromatography, or capillary zone electrochromatography.

Yet in certain embodiments, the present invention is a method of determining the conceptual segment numbers for a chromatographic technique where a solute is an electrolyte. The segment number of an electrolyte accounts for additional segment numbers that are not present with a non-electrolyte species. For example, the segment interaction concept provides the framework to account for the attractive interaction ions with the hydrophilic segments of organic solvents and the repulsive interaction of ions with the hydrophobic segments of organic solvents. Once the segment numbers of the solute are determined, the methods disclosed herein can then predict solute activity coefficients and resulting phase behavior in one or more solvents. In a certain embodiment, the electrolyte is an active pharmaceutical ingredient.

One embodiment of the present invention is a method of determining equivalent numbers of a stationary phase component for a chromatography analysis. The conceptual segment numbers of the stationary phase component can be determined from measuring a degree of surface interaction of the plurality of predetermined solutes with the stationary phase when each of the plurality of predetermined solutes interacts with the stationary phase. The degree of the surface interactions between the plurality of predetermined solutes and the stationary phase can be measured by obtaining partition coefficient data or retention factor data of the plurality of the predetermined solutes. Such partition coefficient data or retention factor data reflects the nature of the solute-stationary phase surface interaction that is a basis for the determination of the conceptual segment numbers for the makeup of the stationary phase. The types of the solute-stationary phase surface interaction can include hydrophobic interaction, electrostatic solvation interaction, electrostatic polar interaction, and hydrophilic interaction.

Other parameters such as the size of the substrate that makes up the stationary phase component can be added to enhance the quality of the model.

The following Examples are illustrative of the invention, including the embodiment that are related to chromatography applications and are not meant to be limiting in any way.

EXAMPLE 1

Modeling a Mixture of Nonelectrolyte Chemical Species

A study was performed to determine how well the NRTL-SAC models the solubility of mixtures comprising a solid organic nonelectrolyte.

The solubility of a solid organic nonelectrolyte is described well by the expression:

$$\ln x_I^{SAT} = \frac{\Delta_{fus}S}{R}\left(1 - \frac{T_m}{T}\right) - \ln\gamma_I^{SAT} \qquad (9)$$

for $T \leq T_m$ and where the entropy of fusion of the solid ($\Delta_{fus}S$) is represented by:

$$\Delta_{fus}S = \frac{\Delta_{fus}H}{T_m} \qquad (10)$$

$x_I^{SAT}$ is the mole fraction of the solid (the solute) dissolved in the solvent phase at saturation, $\gamma_I^{SAT}$ is the activity coefficient for the solute in the solution at saturation, R is the gas constant, T is the temperature, and $T_m$ is the melting point of the solid. Given a polymorph, $\Delta_{fus}S$ and $T_m$ are fixed and the solubility is then a function of temperature and activity coefficient of the solute in the solution. The activity coefficient of the solute in the solution plays the key role in determining the solubility. In general, the activity coefficient of the solute in the solution is usually calculated from a liquid activity coefficient model.

Except for the ideal solution model, an activity coefficient model is often written in two parts as such:

$$\ln\gamma_I = \ln\gamma_I^C + \ln\gamma_I^R \qquad (11)$$

$\gamma_I^C$ and $\gamma_I^R$ are the combinatorial and residual contributions to the activity coefficient of component I, respectively.

In NRTL-SAC, the combinatorial part, $\gamma_I^C$, is calculated from the Flory-Huggins term for the entropy of mixing. The residual part, $\gamma_I^R$, is set equal to the local composition (lc) interaction contribution, $\gamma_I^{lc}$:

$$\ln\gamma_I^R = \ln\gamma_I^{lc} = \sum_m r_{m,I}[\ln\gamma_m^{lc} - \ln\gamma_m^{lc,I}] \qquad (12)$$

with $$\ln\gamma_m^{lc} = \frac{\sum_j x_j G_{jm}\tau_{jm}}{\sum_k x_k G_{km}} + \sum_{m'} \frac{x_{m'}G_{mm'}}{\sum_k x_k G_{km'}}\left(\tau_{mm'} - \frac{\sum_k x_k G_{km'}\tau_{km'}}{\sum_k x_k G_{km'}}\right),$$

$$\ln\gamma_m^{lc,I} = \qquad (13)$$

$$\frac{\sum_j x_{j,I}G_{jm}\tau_{jm}}{\sum_k x_{k,I}G_{km}} + \sum_{m'} \frac{x_{m',I}G_{mm'}}{\sum_k x_{k,I}G_{km'}}\left(\tau_{mm'} - \frac{\sum_k x_{k,I}G_{km'}\tau_{km'}}{\sum_k x_{k,I}G_{km'}}\right),$$

$$x_j = \frac{\sum_J x_J r_{j,J}}{\sum_I \sum_i x_I r_{i,I}},$$

$$x_{j,I} = \frac{r_{j,I}}{\sum_j r_{j,I}},$$

where i, j, k, m, m are the segment-based species index, I, J are the component index, $x_j$ is the segment-based mole fraction of segment species j, and $x_J$ is the mole fraction of component J, $r_{m,I}$ is the number of segment species m contained in component I, $\gamma_m^{lc}$ is the activity coefficient of segment species m, and $\gamma_m^{lc,I}$ is the activity coefficient of segment species m contained only in component I. G and $\tau$ are local binary quantities related to each other by the NRTL non-random factor parameter $\alpha$:

$$G = \exp(-\alpha\tau) \qquad (14)$$

The equation:

$$\ln\gamma_I^R = \ln\gamma_I^{lc} = \sum_m r_{m,I}[\ln\gamma_m^{lc} - \ln\gamma_m^{lc,I}] \qquad (15)$$

is a general form for the local composition interaction contribution to activity coefficients of components in the NRTL-SAC model of the present invention. For mono-segment solvent components(S), this equation can be simplified and reduced to the classical NRTL model as follows:

$$\ln\gamma_{I=S}^{lc} = \sum_m r_{m,S}[\ln\gamma_m^{lc} - \ln\gamma_m^{lc,S}] \qquad (16)$$

with $$r_{m,S} = 1, \ln\gamma_m^{lc,S} = 0. \qquad (17)$$

Therefore, $$\ln\gamma_{I=S}^{lc} = \frac{\sum_j x_j G_{jS}\tau_{jS}}{\sum_k x_k G_{kS}} + \sum_m \frac{x_m G_{Sm}}{\sum_k x_k G_{km}}\left(\tau_{Sm} - \frac{\sum_k x_k G_{km}\tau_{km}}{\sum_k x_k G_{km}}\right), \qquad (18)$$

where $$G_{jS} = \exp(-\alpha_{jS}\tau_{jS}), G_{Sj} = \exp(-\alpha_{jS}\tau_{Sj}). \qquad (19)$$

This is the same equation as the classical NRTL model.

Three conceptual segments were defined for nonelectrolyte molecules: a hydrophobic segment, a polar segment, a hydrophilic segment and a solvation segment. These conceptual segments qualitatively capture the phase behavior of real molecules and their corresponding segments. Real molecules in turn are used as reference molecules for the conceptual segments and available phase equilibrium data of these reference molecules are used to identify NRTL binary parameters for the conceptual segments. Preferably, these reference molecules possess distinct molecular characteristics (i.e., hydrophobic, hydrophilic, or polar) and have abundant, publicly available, thermodynamic data (e.g., phase equilibrium data).

The study was focused on the 59 ICH solvents used in pharmaceutical process design. Water, triethylamine, and n-octanol were also considered. Table 1 shows these 62 solvents and the solvent characteristics.

TABLE 1

Common Solvents in Pharmaceutical Process Design

| Solvent (Component 1) | $\tau_{12}^a$ | $\tau_{21}^a$ | $\tau_{12}^b$ | $\tau_{21}^b$ | $\tau_{12}^c$ | $\tau_{21}^c$ | Solvent characteristics |
|---|---|---|---|---|---|---|---|
| ACETIC-ACID | 1.365 | 0.797 | 2.445 | −1.108 | | | Complex |
| ACETONE | 0.880 | 0.935 | 0.806 | 1.244 | | | Polar |
| ACETONITRILE | 1.834 | 1.643 | 0.707 | 1.787 | | | Polar |
| ANISOLE | | | | | | | Hydrophobic |

TABLE 1-continued

Common Solvents in Pharmaceutical Process Design

| Solvent (Component 1) | $\tau_{12}{}^a$ | $\tau_{21}{}^a$ | $\tau_{12}{}^b$ | $\tau_{21}{}^b$ | $\tau_{12}{}^c$ | $\tau_{21}{}^c$ | Solvent characteristics |
|---|---|---|---|---|---|---|---|
| BENZENE | 1.490 | −0.614 | | | 3.692 | 5.977 | Hydrophobic |
| 1-BUTANOL | −0.113 | 2.639 | 0.269 | 2.870 | −2.157 | 5.843 | Hydrophobic/Hydrophilic |
| 2-BUTANOL | −0.165 | 2.149 | −0.168 | 3.021 | −1.539 | 5.083 | Hydrophobic/Hydrophilic |
| N-BUTYL-ACETATE | | | 1.430 | 2.131 | | | Hydrophobic/Polar |
| METHYL-TERT-BUTYL-ETHER | −0.148 | 0.368 | 1.534 | 4.263 | | | Hydrophobic |
| CARBON-TETRACHLORIDE | 1.309 | −0.850 | | | 5.314 | 7.369 | Hydrophobic |
| CHLOROBENZENE | 0.884 | −0.194 | | | 4.013 | 7.026 | Hydrophobic |
| CHLOROFORM | 1.121 | −0.424 | | | 3.587 | 4.954 | Hydrophobic |
| CUMENE | | | | | | | Hydrophobic |
| CYCLOHEXANE | −0.824 | 1.054 | | | 6.012 | 9.519 | Hydrophobic |
| 1,2-DICHLOROETHANE | 1.576 | −0.138 | 3.207 | 4.284 | 2.833 | 4.783 | Hydrophobic |
| 1,1-DICHLOROETHYLENE | | | | | | | Hydrophobic |
| 1,2-DICHLOROETHYLENE | | | | | | | Hydrophobic |
| DICHLOROMETHANE | 0.589 | 0.325 | 1.983 | 3.828 | | | Polar |
| 1,2-DIMETHOXYETHANE | | | 0.450 | 1.952 | | | Polar |
| N,N-DIMETHYLACETAMIDE | | | −0.564 | 1.109 | | | Polar |
| N,N-DIMETHYLFORMAMIDE | 1.245 | 1.636 | −1.167 | 2.044 | | | Polar |
| DIMETHYL-SULFOXIDE | | | −2.139 | 0.955 | | | Polar |
| 1,4-DIOXANE | 1.246 | 0.097 | 1.003 | 1.010 | | | Polar |
| ETHANOL | 0.533 | 2.192 | −0.024 | 1.597 | | | Hydrophobic/Hydrophilic |
| 2-ETHOXYETHANOL | −0.319 | 2.560 | −1.593 | 1.853 | | | Hydrophobic/Hydrophilic |
| ETHYL-ACETATE | 0.771 | 0.190 | | | 0.508 | 3.828 | Hydrophobic/Polar |
| ETHYLENE-GLYCOL | | | 1.380 | −1.660 | | | Hydrophilic |
| DIETHYL-ETHER | −0.940 | 1.400 | | | 1.612 | 3.103 | Hydrophobic |
| ETHYL-FORMATE | | | | | | | Polar |
| FORMAMIDE | | | | | | | Complex |
| FORMIC-ACID | | | −0.340 | −1.202 | | | Complex |
| N-HEPTANE | −0.414 | 0.398 | | | | | Hydrophobic |
| N-HEXANE | | | 6.547 | 10.949 | 6.547 | 10.949 | Hydrophobic |
| ISOBUTYL-ACETATE | | | | | | | Polar |
| ISOPROPYL-ACETATE | | | | | | | Polar |
| METHANOL | 1.478 | 1.155 | 0.103 | 0.396 | | | Hydrophobic/Hydrophilic |
| 2-METHOXYETHANOL | | | 1.389 | −0.566 | | | Hydrophobic/Hydrophilic |
| METHYL-ACETATE | | | 0.715 | 2.751 | | | Polar |
| 3-METHYL-1-BUTANOL | 0.062 | 2.374 | −0.042 | 3.029 | −0.598 | 5.680 | Hydrophobic/Hydrophilic |
| METHYL-BUTYL-KETONE | | | | | | | Hydrophobic/Polar |
| METHYLCYCLOHEXANE | 1.412 | −1.054 | | | | | Polar |
| METHYL-ETHYL-KETONE | −0.036 | 1.273 | 0.823 | 2.128 | −0.769 | 3.883 | Hydrophobic/Polar |
| METHYL-ISOBUTYL-KETONE | | | 0.977 | 4.868 | | | Hydrophobic/Polar |
| ISOBUTANOL | 0.021 | 2.027 | 0.592 | 2.702 | −1.479 | 5.269 | Hydrophobic/Hydrophilic |
| N-METHYL-2-PYRROLIDONE | −0.583 | 3.270 | −0.235 | 0.437 | | | Hydrophobic |
| NITROMETHANE | | | 1.968 | 2.556 | | | Polar |
| N-PENTANE | 0.496 | −0.523 | | | | | Hydrophobic |
| 1-PENTANOL | −0.320 | 2.567 | −0.029 | 3.583 | | | Hydrophobic/Hydrophilic |
| 1-PROPANOL | 0.049 | 2.558 | 0.197 | 2.541 | | | Hydrophobic/Hydrophilic |
| ISOPROPYL-ALCOHOL | 0.657 | 1.099 | 0.079 | 2.032 | | | Hydrophobic/Hydrophilic |
| N-PROPYL-ACETATE | | | 1.409 | 2.571 | | | Hydrophobic/Polar |
| PYRIDINE | −0.665 | 1.664 | −0.990 | 3.146 | | | Polar |
| SULFOLANE | | | 1.045 | 0.396 | | | Polar |
| TETRAHYDROFURAN | 0.631 | 1.981 | 1.773 | 0.563 | | | Polar |
| 1,2,3,4-TETRAHYDRONAPHTHALENE | 1.134 | −0.631 | | | | | Hydrophobic |
| TOLUENE | −0.869 | 1.292 | | | 4.241 | 7.224 | Hydrophobic |
| 1,1,1-TRICHLOROETHANE | 0.535 | −0.197 | | | | | Hydrophobic |
| TRICHLOROETHYLENE | 1.026 | −0.560 | | | | | Hydrophobic |
| M-XYLENE | | | | | | | Hydrophobic |
| WATER | 10.949 | 6.547 | | | | | Hydrophilic |
| TRIETHYLAMINE | −0.908 | 1.285 | 1.200 | 1.763 | −0.169 | 4.997 | Hydrophobic/Polar |
| 1-OCTANOL | −0.888 | 3.153 | | | 0.301 | 8.939 | Hydrophobic/Hydrophilic |

Wherein:
1. $\tau_{12}{}^a$ and $\tau_{21}{}^a$ are NRTL binary $\tau$ parameters for systems of the listed solvents and hexane. NRTL non-random factor parameter, $\alpha$, is fixed as a constant of 0.2. In these binary systems, solvent is component 1 and hexane component 2. $\tau$'s were determined from available VLE & LLE data.
2. $\tau_{12}{}^b$ and $\tau_{21}{}^b$ are NRTL binary $\tau$ parameters for systems of the listed solvents and water. NRTL non-random factor parameter, $\alpha$, is fixed as a constant of 0.3. In these binary systems, solvent is component 1 and water component 2. $\tau$'s were determined from available VLE data.
3. $\tau_{12}{}^c$ and $\tau_{21}{}^c$ are NRTL binary $\tau$ parameters for systems of the listed solvents and water. NRTL non-random factor parameter, $\alpha$, is fixed as a constant of 0.2. In these binary systems, solvent is component 1 and water component 2. $\tau$'s were determined from available LLE data.

Hydrocarbon solvents (aliphatic or aromatic), halogenated hydrocarbons, and ethers are mainly hydrophobic. Ketones, esters and amides are both hydrophobic and polar. Alcohols, glycols, and amines may have both substantial hydrophilicity and hydrophobicity. Acids are complex, with hydrophilicity, polarity, and hydrophobicity.

Also shown in Table 1 are the available NRTL binary parameters ($\tau$) for various solvent-water binary systems and solvent-hexane binary systems. Applicants obtained these binary parameters from fitting selected literature phase equilibrium data and deliberately ignoring the temperature dependency of these parameters. These values illustrate the range of values for these binary parameters. Note that many of the binary parameters are missing, as the phase equilibrium data is not found in the literature or simply has never been determined for that solvent mixture. Also note the sheer number of binary parameters needed for the prior art NRTL models for even a moderately sized system of solvents. For example, to model 60 solvents with the NRTL model, 60×60 NRTL binary parameters would be needed.

Table 1 shows that, for the NRTL binary parameters determined from VLE and LLE data for hydrophobic solvent (1) water (2) binaries, all hydrophobic solvents exhibit similar repulsive interactions with water and both $\tau_{12}$ and $\tau_{21}$ are large positive values for the solvent-water binaries. When the hydrophobic solvents also carry significant hydrophilic or polar characteristics, $\tau_{12}$ becomes negative while $\tau_{21}$ retain a large positive value.

Table 1 also illustrates that similar repulsive, but weaker, interactions between a polar solvent (1) and hexane (2), a representative hydrophobic solvent. Both $\tau_{12}$ and $\tau_{21}$ are small, positive values for the solvent-hexane binaries. The interactions between hydrophobic solvents and hexane are weak and the corresponding NRTL binary parameters are around or less than unity, characteristic of nearly ideal solutions.

The interactions between polar solvents (1) and water (2) are more subtle. While all $\tau_{21}$ are positive, $\tau_{12}$ can be positive or negative. This is probably due to different polar molecules exhibiting different interactions, some repulsive and others attractive, with hydrophilic molecules.

Hexane and water were chosen as the reference molecule for hydrophobic segment and for hydrophilic segment, respectively. The selection of reference molecule for polar segment requires attention to the wide variations of interactions between polar molecules and water. Acetonitrile was chosen as the reference molecule for a polar segment, and a mechanism was introduced to tune the way the polar segment is characterized. The tuning mechanism, as shown in Table 2, allows tuning of the interaction characteristics between the polar segment and the hydrophilic segment. In other words, instead of using only one polar segment ("Y"), two polar segments ("Y−" and "Y+") were used. The difference between Y− and Y+ is the way they interact with the hydrophilic segment.

The chosen values for the NRTL binary interactions parameters, $\alpha$ and $\tau$, for the three conceptual segments are summarized in Table 2.

TABLE 2

NRTL Binary Parameters for Conceptual Segments in NRTL-SAC

| Segment (1) | X (hydrophobic segment) | X (hydrophobic segment) | Y− (polar segment) | Y+ (polar segment) | X (hydrophobic segment) |
|---|---|---|---|---|---|
| Segment (2) | Y− (polar segment) | Z (hydrophilic segment) | Z (hydrophilic segment) | Z (hydrophilic segment) | Y+ (polar segment) |
| $\tau_{12}$ | 1.643 | 6.547 | −2.000 | 2.000 | 1.643 |
| $\tau_{21}$ | 1.834 | 10.949 | 1.787 | 1.787 | 1.834 |
| $\alpha_{12} = \alpha_{21}$ | 0.2 | 0.2 | 0.3 | 0.3 | 0.2 |

As a first approximation, the temperature dependency of the binary parameters was ignored.

The binary parameters for the hydrophobic segment (1)—hydrophilic segment (2) were determined from available liquid-liquid equilibrium data of hexane-water binary mixture (see Table 1). $\alpha$ was fixed at 0.2 because it is the customary value for $\alpha$ for systems that exhibit liquid-liquid separation. Here both $\tau_{12}$ and $\tau_{21}$ are large positive values (6.547, 10.950). They highlight the strong repulsive nature of the interactions between the hydrophobic segment and the hydrophilic segment.

Determining a suitable value for $\alpha$ is known in the art. See J. M. PRAUSNITZ, ET AL., MOLECULAR THERMODYNAMICS OF FLUID-PHASE EQUILIBRIA 261 (3d ed. 1999).

The binary parameters for the hydrophobic segment (1)—polar segment (2) were determined from available liquid-liquid equilibrium data of hexane-acetonitrile binary mixture (see Table 1). Again, at was fixed at 0.2. Both $\tau_{12}$ and $\tau_{21}$ were small positive values (1.643, 1.834). They highlight the weak repulsive nature of the interactions between hydrophobic segment and polar segment.

The binary parameters for the hydrophilic segment (1)—polar segment (2) were determined from available vapor-liquid equilibrium data of water-acetonitrile binary mixture (see Table 1). $\alpha$ was fixed at 0.3 for the hydrophilic segment—polar segment pair because this binary does not exhibit liquid-liquid separation. $\tau_{12}$ was fixed at a positive value (1.787) and $\tau_{21}$ was allowed to vary between −2 and 2. Two types of polar segments were allowed, Y− and Y+. For Y− polar segment, the values of $\tau_{12}$ and $\tau_{21}$ were (1.787, −2). For Y+ polar segment, they were (1.787, 2). Note that both Y− polar segment and Y+ polar segment exhibited the same repulsive interactions with hydrophobic segments as discussed in the previous paragraph. Also, ideal solution was assumed for Y− polar segment and Y+ polar segment mixtures (i.e., $\tau_{12}=\tau_{21}=0$).

Table 2 captures the general trends for the NRTL binary parameters that were observed for a wide variety of hydrophobic, polar, and hydrophilic molecules.

The application of the NRTL-SAC model requires a databank of molecular parameters for common solvents used in the industry. In this example, each solvent was described by using up to four molecular parameters, i.e., X, Y+, Y−, and Z. So, using four molecular parameters to model a system of 60 solvents, a set of up to 4×60 molecular parameters would be used. However, due to the fact that these molecular parameters represent certain unique molecular characteristics, often only one or two molecular parameters are needed for most solvents. For example, alkanes are hydrophobic and they are well represented with hydrophobicity, X, alone. Alcohols are hybrids of hydrophobic segments and hydrophilic segments and they are well represented with X and Z. Ketones, esters, and ethers are polar molecules with varying degrees of hydrophobic contents. They are well represented by X and Y's. Hence, the needed set of molecular parameters can be much smaller than 4×60.

Determination of solvent molecular parameters involves regression of experimental VLE or LLE data for binary systems of interested solvent and the above-mentioned reference molecules (i.e., hexane, acetonitrile, and water) or their substitutes. Solvent molecular parameters are the adjustable parameters in the regression. If binary data is lacking for the solvent with the reference molecules, data for other binaries may be used as long as the molecular parameters for the substitute reference molecules are already identified. In a way, these reference molecules can be thought of as molecular probes that are used to elucidate the interaction characteristics of the solvent molecules. These molecular probes express the interactions in terms of binary phase equilibrium data.

Table 3 list the molecular parameters identified for the common solvents in the ICH list.

TABLE 3

Molecular Parameters for Common Solvents.

| Solvent name | X | Y− | Y+ | Z |
|---|---|---|---|---|
| ACETIC-ACID | 0.045 | 0.164 | 0.157 | 0.217 |
| ACETONE | 0.131 | 0.109 | 0.513 | |
| ACETONITRILE | 0.018 | 0.131 | 0.883 | |
| ANISOLE | 0.722 | | | |
| BENZENE | 0.607 | | 0.190 | |
| 1-BUTANOL | 0.414 | 0.007 | | 0.485 |
| 2-BUTANOL | 0.335 | 0.082 | | 0.355 |
| N-BUTYL-ACETATE | 0.317 | 0.030 | 0.330 | |
| METHYL-TERT-BUTYL-ETHER | 1.040 | 0.219 | 0.172 | |
| CARBON-TETRACHLORIDE | 0.718 | | 0.141 | |
| CHLOROBENZENE | 0.710 | | 0.424 | |
| CHLOROFORM | 0.278 | | 0.039 | |
| CUMENE | 1.208 | | 0.541 | |
| CYCLOHEXANE | 0.892 | | | |
| 1,2-DICHLOROETHANE | 0.394 | | 0.691 | |
| 1,1-DICHLOROETHYLENE | 0.529 | | 0.208 | |
| 1,2-DICHLOROETHYLENE | 0.188 | | 0.832 | |
| DICHLOROMETHANE | 0.321 | | 1.262 | |
| 1,2-DIMETHOXYETHANE | 0.081 | 0.194 | 0.858 | |
| N,N-DIMETHYLACETAMIDE | 0.067 | 0.030 | 0.157 | |
| N,N-DIMETHYLFORMAMIDE | 0.073 | 0.564 | 0.372 | |
| DIMETHYL-SULFOXIDE | 0.532 | 2.890 | | |
| 1,4-DIOXANE | 0.154 | 0.086 | 0.401 | |
| ETHANOL | 0.256 | 0.081 | | 0.507 |
| 2-ETHOXYETHANOL | 0.071 | 0.318 | | 0.237 |
| ETHYL-ACETATE | 0.322 | 0.049 | 0.421 | |
| ETHYLENE-GLYCOL | | 0.141 | | 0.338 |

TABLE 3-continued

Molecular Parameters for Common Solvents.

| Solvent name | X | Y− | Y+ | Z |
|---|---|---|---|---|
| DIETHYL-ETHER | 0.448 | 0.041 | 0.165 | |
| ETHYL-FORMATE | 0.257 | | 0.280 | |
| FORMAMIDE | | 0.089 | 0.341 | 0.252 |
| FORMIC-ACID | 0.707 | 2.470 | | |
| N-HEPTANE | 1.340 | | | |
| N-HEXANE | 1.000 | | | |
| ISOBUTYL-ACETATE | 1.660 | | 0.108 | |
| ISOPROPYL-ACETATE | 0.552 | 0.154 | 0.498 | |
| METHANOL | 0.088 | 0.149 | 0.027 | 0.562 |
| 2-METHOXYETHANOL | 0.052 | 0.043 | 0.251 | 0.560 |
| METHYL-ACETATE | 0.236 | | 0.337 | |
| 3-METHYL-1-BUTANOL | 0.419 | | 0.538 | 0.314 |
| METHYL-BUTYL-KETONE | 0.673 | 0.224 | 0.469 | |
| METHYLCYCLOHEXANE | 1.162 | | 0.251 | |
| METHYL-ETHYL-KETONE | 0.247 | 0.036 | 0.480 | |
| METHYL-ISOBUTYL-KETONE | 0.673 | 0.224 | 0.469 | |
| ISOBUTANOL | 0.566 | | 0.067 | 0.485 |
| N-METHYL-2-PYRROLIDONE | 0.197 | 0.322 | | 0.305 |
| NITROMETHANE | 0.025 | | 1.216 | |
| N-PENTANE | 0.898 | | | |
| 1-PENTANOL | 0.474 | 0.223 | 0.426 | 0.248 |
| 1-PROPANOL | 0.375 | 0.030 | | 0.511 |
| ISOPROPYL-ALCOHOL | 0.351 | 0.070 | 0.003 | 0.353 |
| N-PROPYL-ACETATE | 0.514 | 0.134 | 0.587 | |
| PYRIDINE | 0.205 | 0.135 | 0.174 | |
| SULFOLANE | 0.210 | | | 0.457 |
| TETRAHYDROFURAN | 0.235 | 0.040 | 0.320 | |
| 1,2,3,4-TETRAHYDRONAPHTHALENE | 0.443 | 0.555 | | |
| TOLUENE | 0.604 | | 0.304 | |
| 1,1,1-TRICHLOROETHANE | 0.548 | | 0.287 | |
| TRICHLOROETHYLENE | 0.426 | 0.285 | | |
| M-XYLENE | 0.758 | 0.021 | 0.316 | |
| WATER | | | | 1.000 |
| TRIETHYLAMINE | 0.557 | 0.105 | | |
| 1-OCTANOL | 0.766 | 0.032 | 0.624 | 0.335 |

Among the ICH solvents, the molecular parameters identified for anisole, cumene, 1,2-dichloroethylene, 1,2-dimethoxyetane, N,N-dimethylacetamide, dimethyl sulfoxide, ethyl formate, isobutyl acetate, isopropyl acetate, methyl-butyl-ketone, tetralin, and trichloroethylene were questionable, due to lack of sufficient experimental binary phase equilibrium data. In fact, no public data for methyl-butyl-ketone (2-hexanone) was found and its molecular parameters were set to be the same as those for methyl-isobutyl-ketone.

Figure 5:
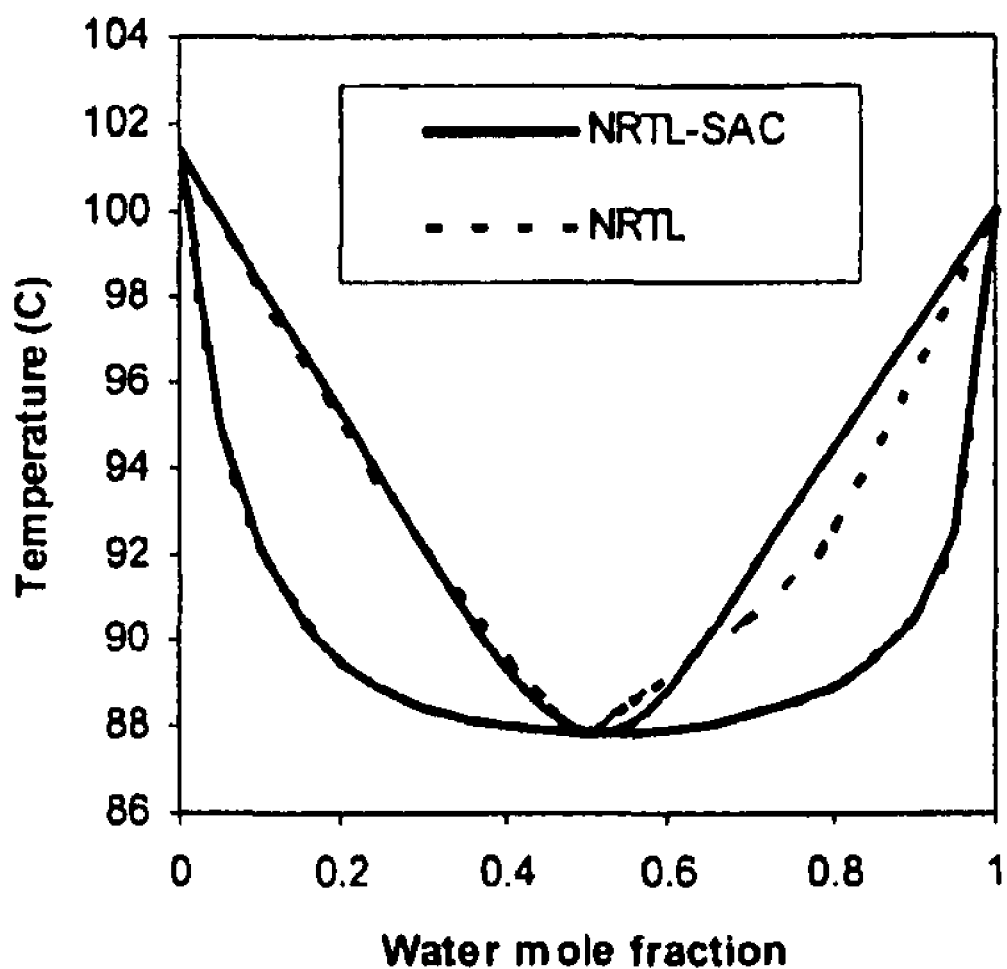
FIG. 5 illustrates a graph showing the binary phase diagram for a water, 1,4-dioxane mixture at atmospheric pressure.
Figure 6:
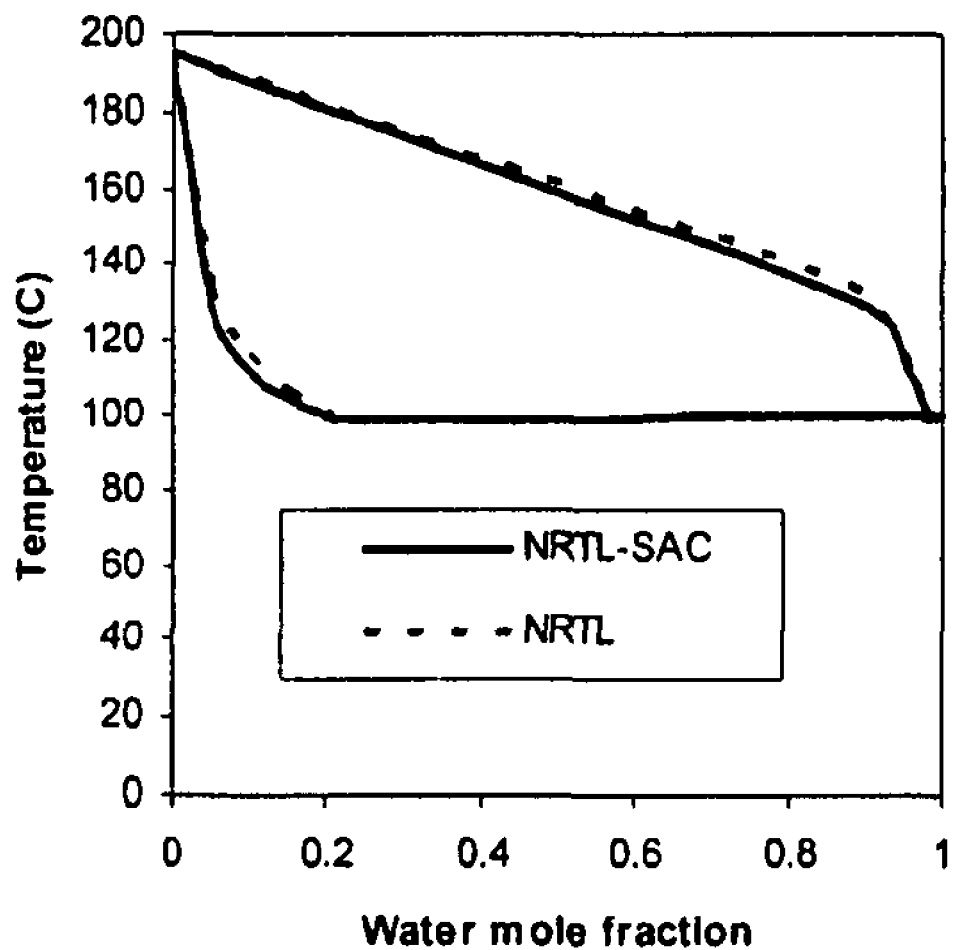
FIG. 6 illustrates a graph showing the binary phase diagram for a water, octanol mixture at atmospheric pressure.
Figure 7:
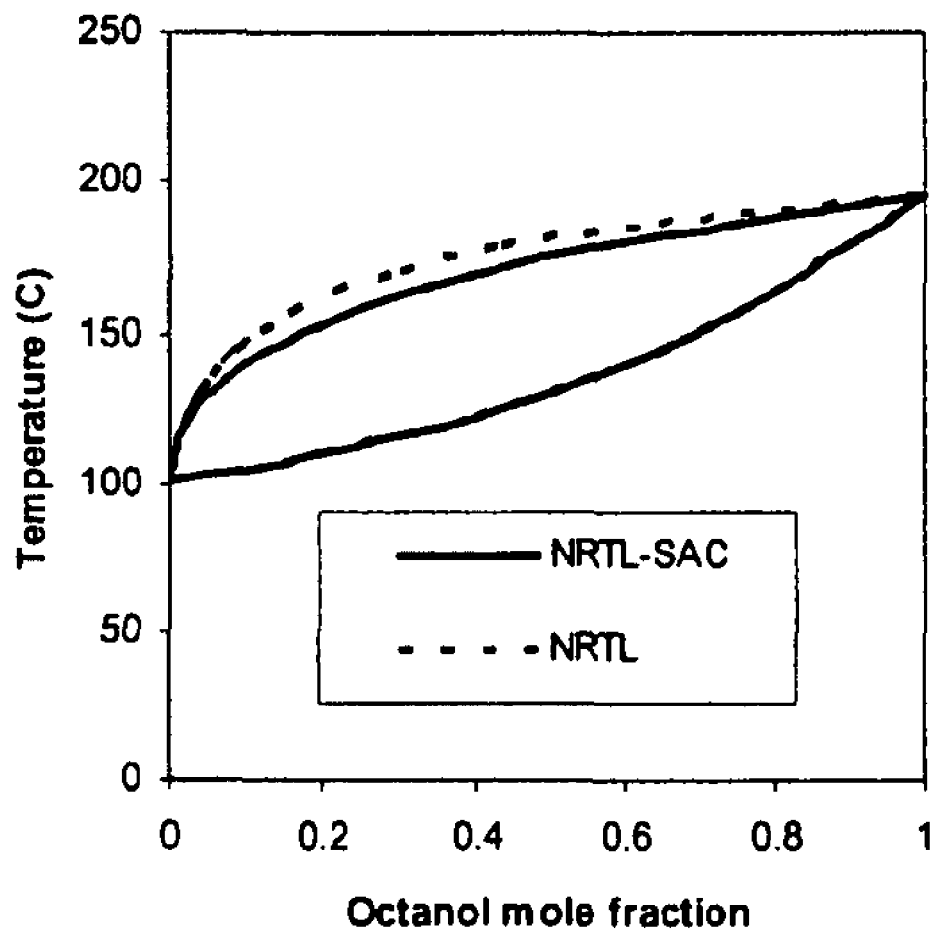
FIG. 7 illustrates a graph showing the binary phase diagram for an octanol, 1,4-dioxane mixture at atmospheric pressure.
Figure 8:
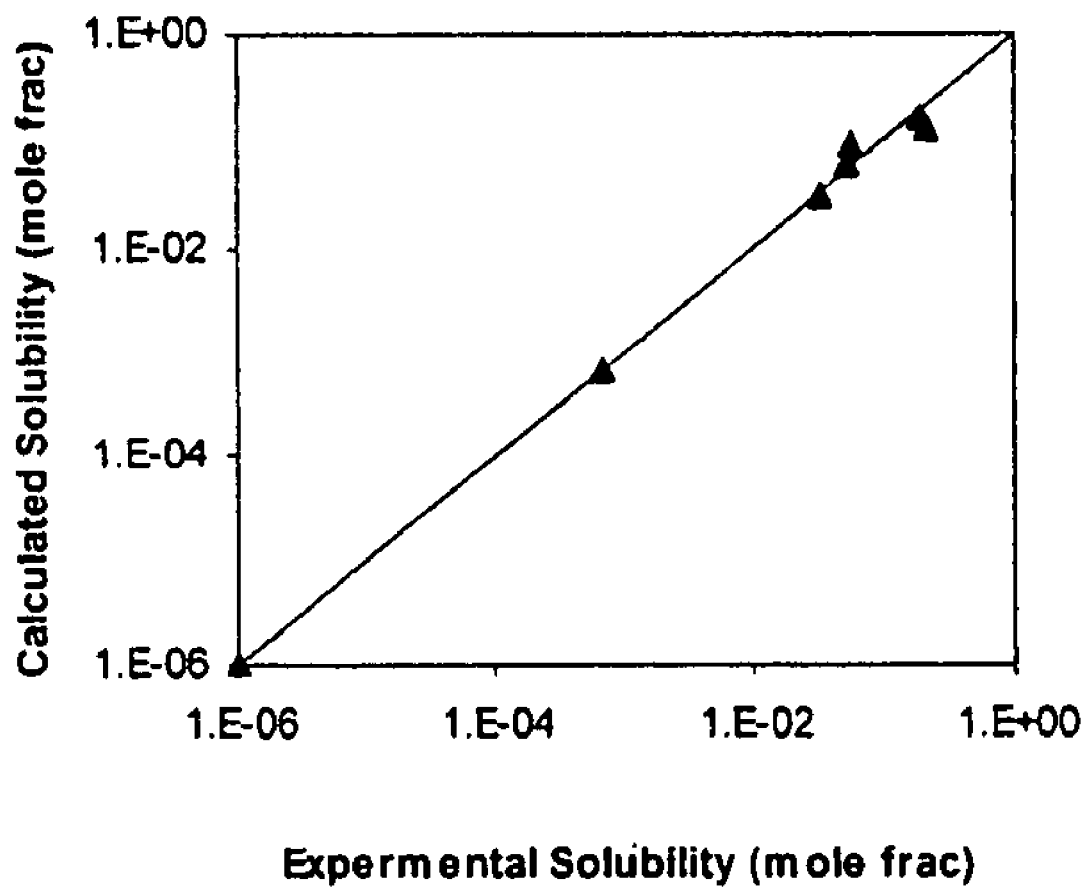
FIG. 8 illustrates a graph showing data of experimental solubilities vs. calculated solubilities for p-aminobenzoic acid in various solvents at 298.15K.
Figure 9:
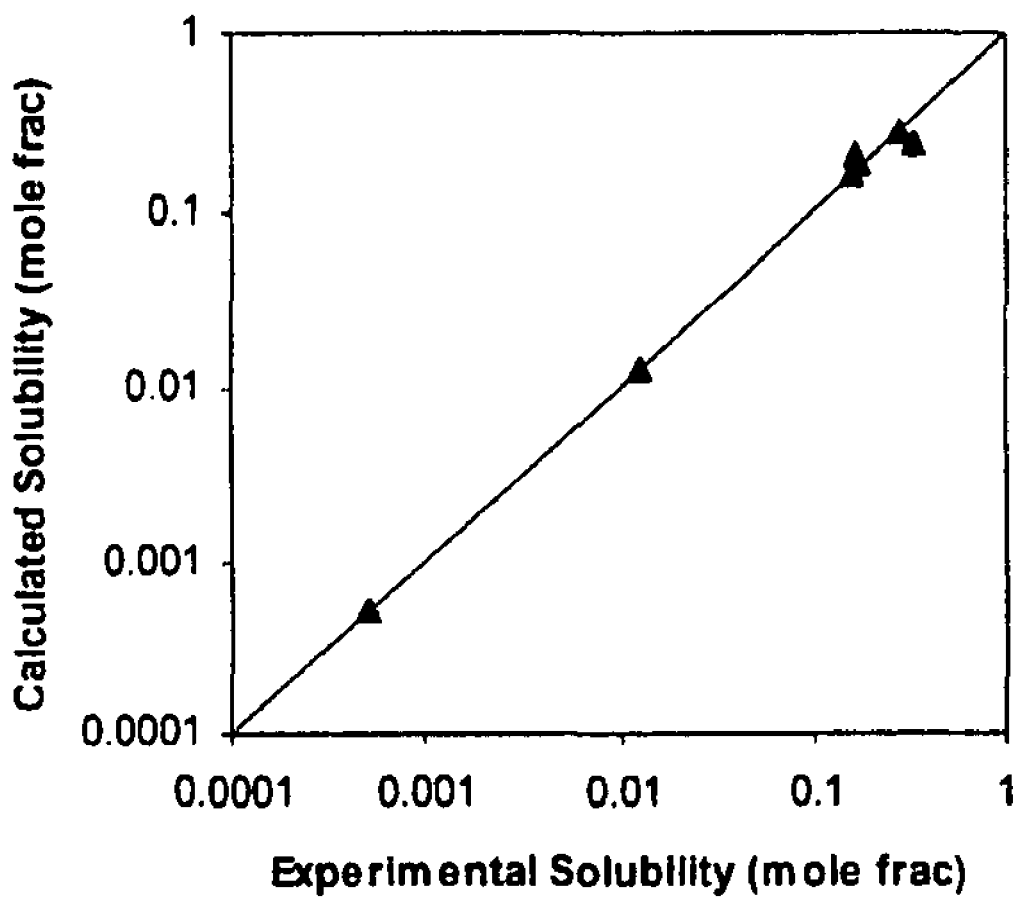
FIG. 9 illustrates a graph showing data of experimental solubilities vs. calculated solubilities for benzoic acid in various solvents at 298.15K.
Figure 10:
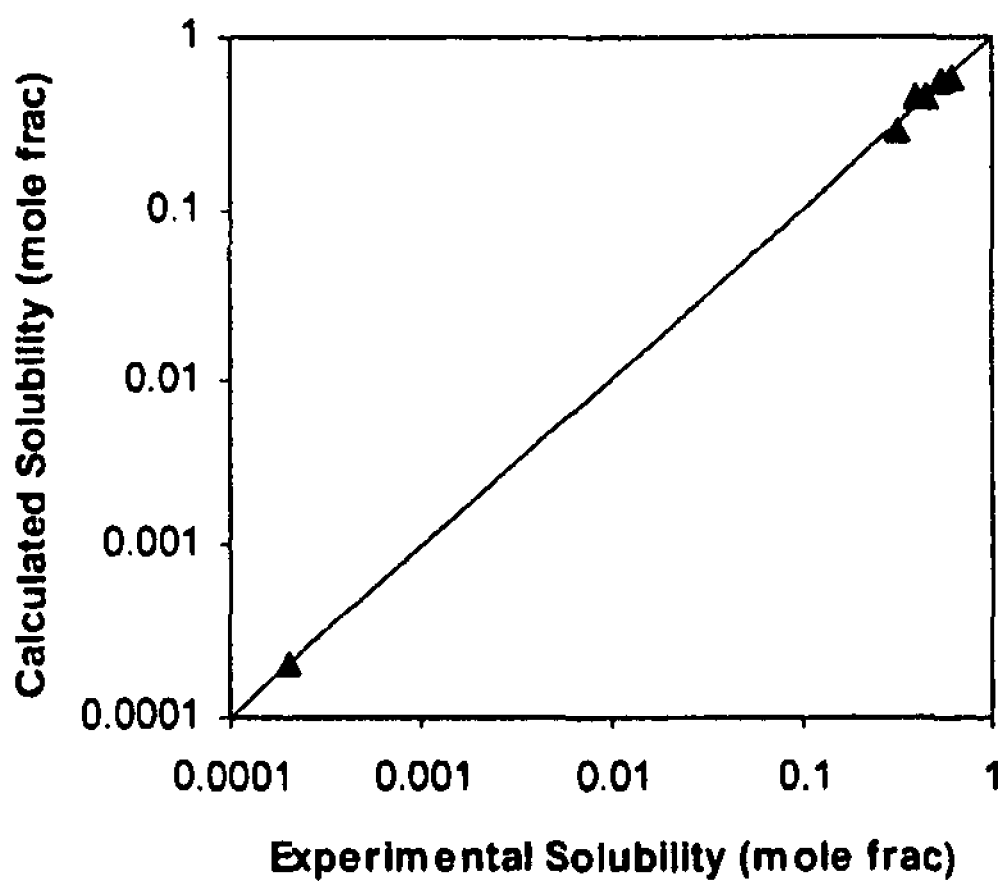
FIG. 10 illustrates a graph showing data of experimental solubilities vs. calculated solubilities for camphor in various solvents at 298.15K.
Figure 11:
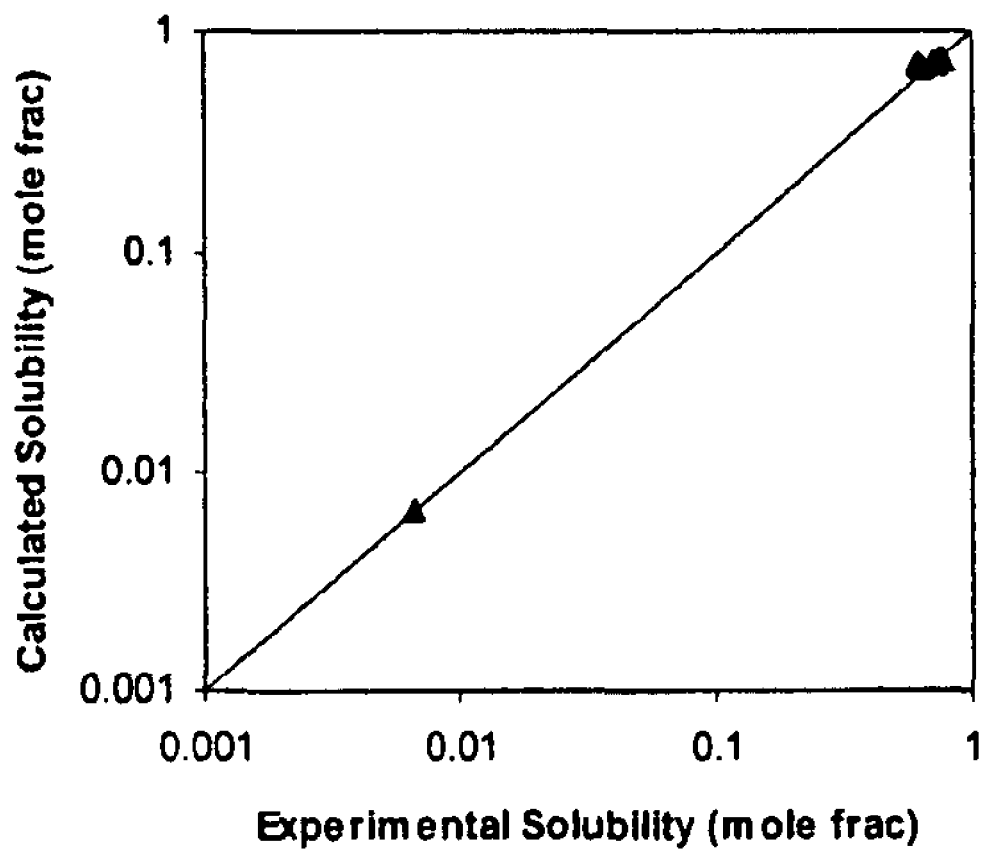
FIG. 11 illustrates a graph showing data of experimental solubilities vs. calculated solubilities for ephedrine in various solvents at 298.15K.
Figure 12:
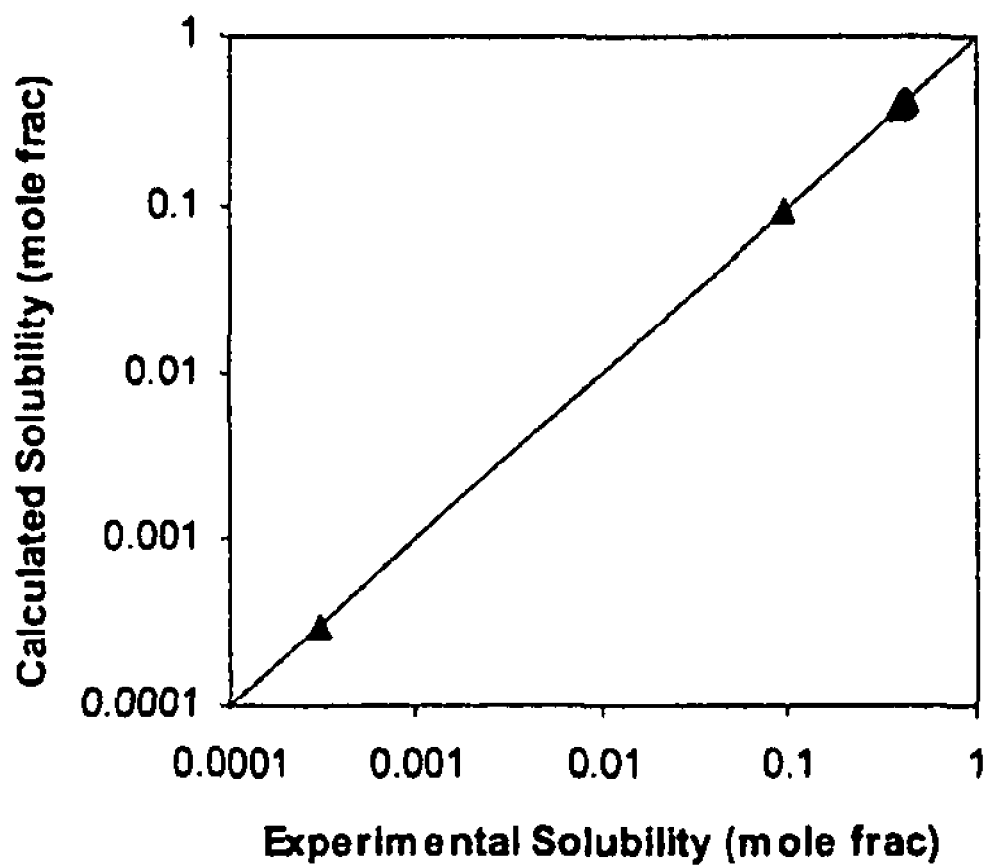
FIG. 12 illustrates a graph showing data of experimental solubilities vs. calculated solubilities for lidocaine in various solvents at 298.15K.
Figure 13:
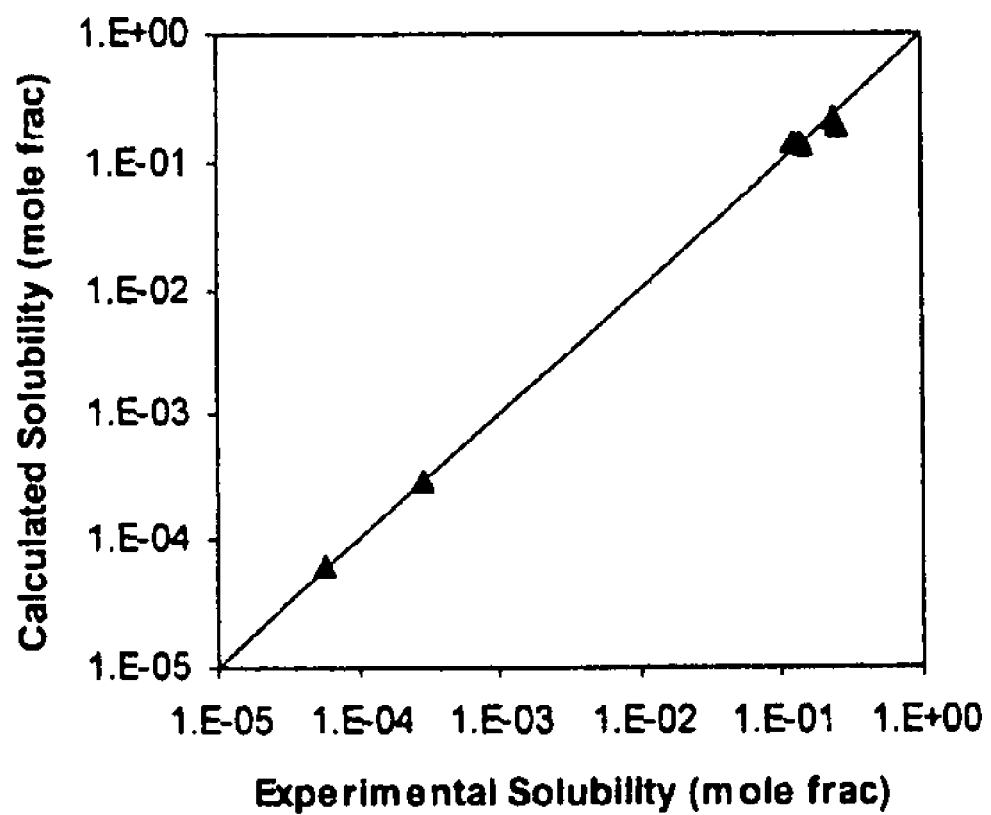
FIG. 13 illustrates a graph showing data of experimental solubilities vs. calculated solubilities for methylparaben in various solvents at 298.15K.
Figure 14:
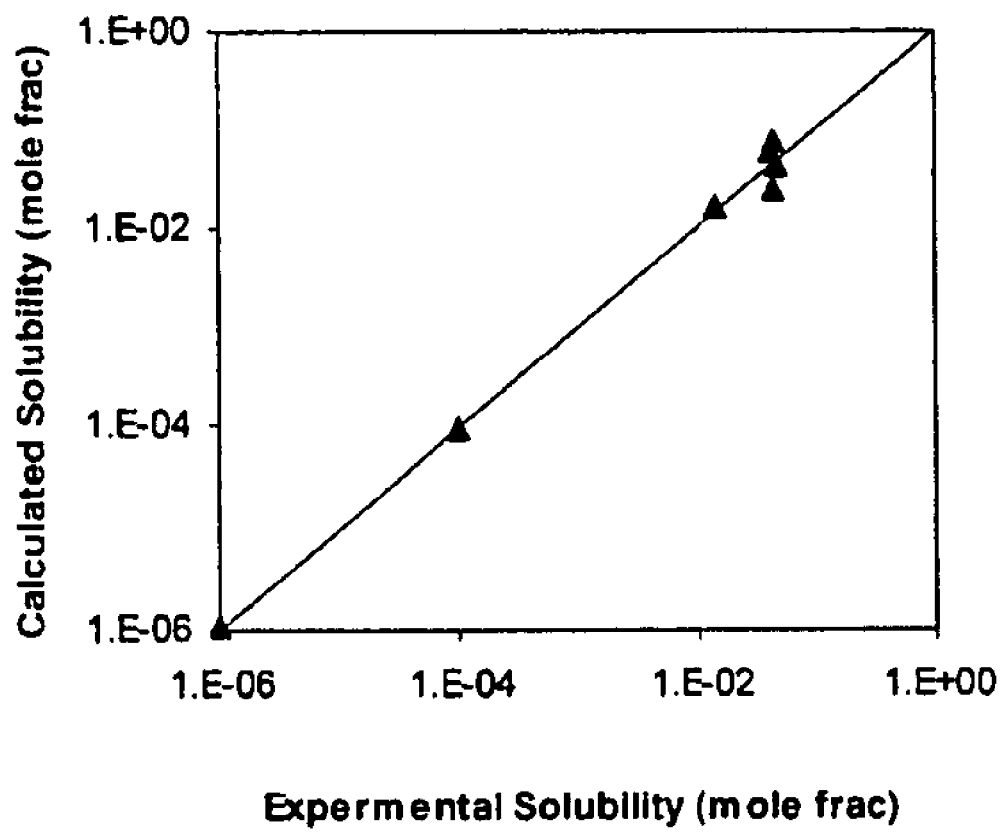
FIG. 14 illustrates a graph showing data of experimental solubilities vs. calculated solubilities for testosterone in various solvents at 298.15K.
Figure 15:
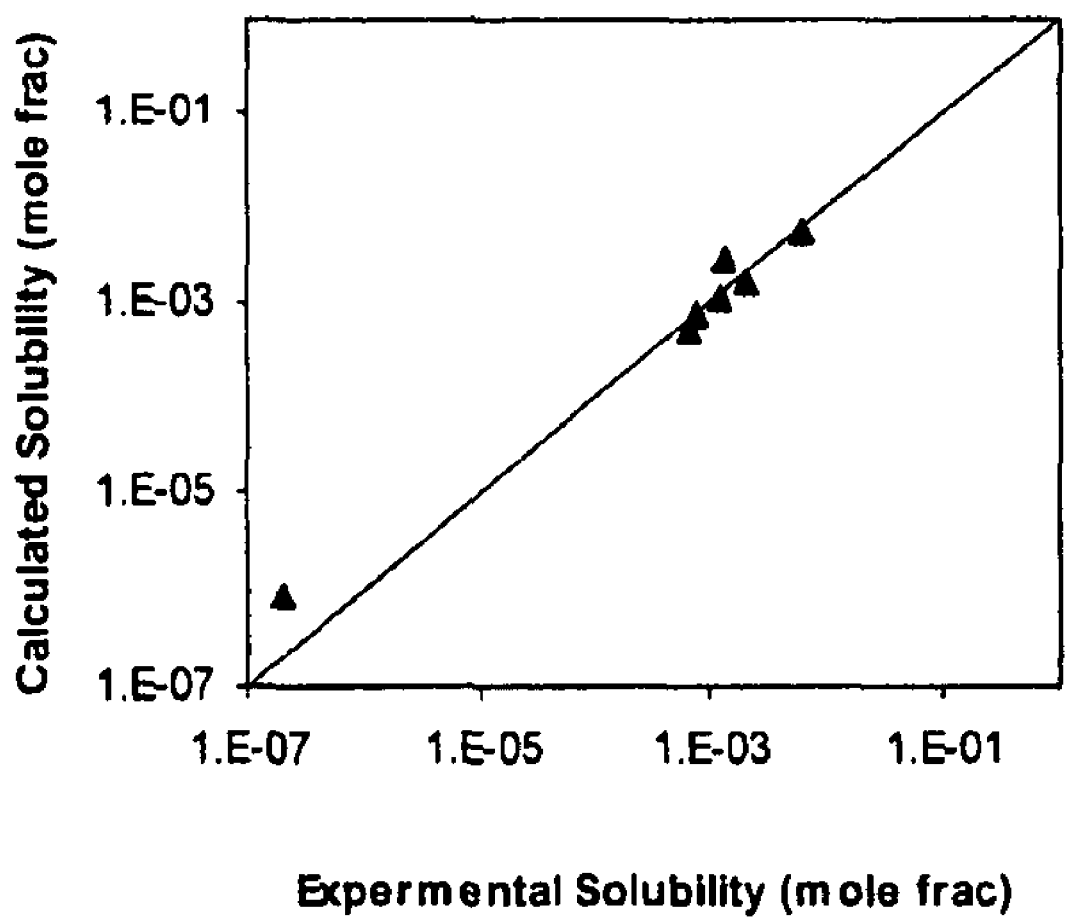
FIG. 15 illustrates a graph showing data of experimental solubilities vs. calculated solubilities for theophylline in various solvents at 298.15K.

The NRTL-SAC model with the molecular parameters qualitatively captures the interaction characteristics of the solvent mixtures and the resulting phase equilibrium behavior. FIGS. 5 to 7 contain three graphs illustrating the binary phase diagrams for a water, 1,4-dioxane, and octanol system at atmospheric pressure. The graphs illustrate the predictions of both the NRTL model with the binary parameters in Table 1 and NRTL-SAC models with the model parameters of Table 3. FIG. 5 illustrates the water, 1,4-dioxane mixture; FIG. 6 illustrates the water, octanol mixture; and FIG. 7 illustrates the octanol, 1,4-dioxane mixture. The predictions with the NRTL-SAC model are broadly consistent with the calculations from the NRTL model that are generally understood to represent experimental data within engineering accuracy.

EXAMPLE 2

Model Prediction Results

Data compiled by Marrero and Abildsko provides a good source of solubility data for large, complex chemicals. Marrero, J. & Abildskov, J., *Solubility and Related Properties of*

Large Complex Chemicals, Part 1. Organic Solutes Ranging from $C_4$ to $C_{40}$, CHEMISTRY DATA SERIES XV, DECHEMA, (2003). From that applicants extracted solubility data for the 8 molecules reported by Lin and Nash. Lin, H.-M. & R. A. Nash, An Experimental Method for Determining the Hildebrand Solubility Parameter of Organic Electrolytes, 82 J. PHARMACEUTICAL SCI. 1018 (1993). Also tested, were 6 additional molecules with sizable solubility data sets.

The NRTL-SAC model was applied to the solvents that are included in Table 3. The molecular parameters determined for the solutes are summarized in Table 4. During the data regression, all experimental solubility data, regardless of the order of magnitude, were assigned with a standard deviation of 20%. The comparisons between the experimental solubility and the calculated solubility are given in FIGS. 8 to 21, which illustrate phase diagrams for the systems at 298.15K and atmospheric pressure.

Good representations for the solubility data was obtained with the NRTL-SAC model. The RMS errors in ln x for the fits are given in Table 4.

TABLE 4

Molecular parameters for solutes.

| Solute | MW | # of solvents | T (K) | X | Y− | Y+ | Z | $lnK_{sp}$ | RMS error on ln x |
|---|---|---|---|---|---|---|---|---|---|
| p-Aminobenzoic acid | 137.14 | 7 | 298.15 | 0.218 | 0.681 | 1.935 | 0.760 | −2.861 | 0.284 |
| Benzoic acid | 122.12 | 7 | 298.15 | 0.524 | 0.089 | 0.450 | 0.405 | −1.540 | 0.160 |
| Camphor | 152.23 | 7 | 298.15 | 0.604 | 0.124 | 0.478 | 0.000 | −0.593 | 0.092 |
| Ephedrine | 165.23 | 7 | 298.15 | 0.458 | 0.068 | 0.000 | 0.193 | −0.296 | 0.067 |
| Lidocaine | 234.33 | 7 | 298.15 | 0.698 | 0.596 | 0.293 | 0.172 | −0.978 | 0.027 |
| Methylparaben | 152.14 | 7 | 298.15 | 0.479 | 0.484 | 1.218 | 0.683 | −2.103 | 0.120 |
| Testosterone | 288.41 | 7 | 298.15 | 1.051 | 0.771 | 0.233 | 0.669 | −3.797 | 0.334 |
| Theophylline | 180.18 | 7 | 298.15 | 0.000 | 0.757 | 1.208 | 0.341 | −6.110 | 0.661 |
| Estriol | 288.38 | 9[a] | 298.15 | 0.853 | 0.000 | 0.291 | 1.928 | −7.652 | 0.608 |
| Estrone | 270.37 | 12 | 298.15 | 0.499 | 0.679 | 1.521 | 0.196 | −6.531 | 0.519 |
| Morphine | 285.34 | 6 | 308.15 | 0.773 | 0.000 | 0.000 | 1.811 | −4.658 | 1.007 |
| Piroxicam | 331.35 | 14[b] | 298.15 | 0.665 | 0.000 | 1.803 | 0.169 | −7.656 | 0.665 |
| Hydrocortisone | 362.46 | 11[c] | 298.15 | 0.401 | 0.970 | 1.248 | 0.611 | −6.697 | 0.334 |
| Haloperidol | 375.86 | 13[d] | 298.15 | 0.827 | 0.000 | 0.000 | 0.131 | −4.398 | 0.311 |

[a]With THF excluded.
[b]With 1,2 dichloroethane, chloroform, diethyl ether, and DMF excluded.
[c]With hexane excluded.
[d]With chloroform and DMF excluded.

$K_{sp}$, the solubility product constant, corresponds to the ideal solubility (in mole fraction) for the solute. The quality of the fit reflects both the effectiveness of the NRTL-SAC model and the quality of the molecular parameters identified from the limited available experimental data for the solvents.

FIGS. 8, 9, 10, 11, 12, 13, 14 and 15 include graphs illustrating the experimental solubilities vs. calculated solubilities for p-aminobenzoic acid, benzoic acid, camphor, ephedrine, lidocaine, methylparaben, testosterone, and theophylline, respectively, in various solvents at 298.15K. The various solvents used were selected from a group of 33 solvents, including acetic acid, acetone, benzene, 1-butanol, n-butyl acetate, carbon tetrachloride, chlorobenzene, chloroform, cyclohexane, 1,2-dichloroethane, dichloromethane, 1,2-dimethoxyethane, N,N-dimethylformamide, dimethyl-sulfoxide, 1,4-dioxane, ethanol, 2-ethoxyethanol, ethyl acetate, ethylene glycol, diethyl ether, formamide, n-heptane, n-hexane, isopropyl acetate, methanol, methyl acetate, 1-pentanol, 1-propanol, isopropyl alcohol, teterhydrofuran, toluene, water, and 1-octanol. The experimental solubility data was represented well with the NRTL-SAC model.

Figure 16:
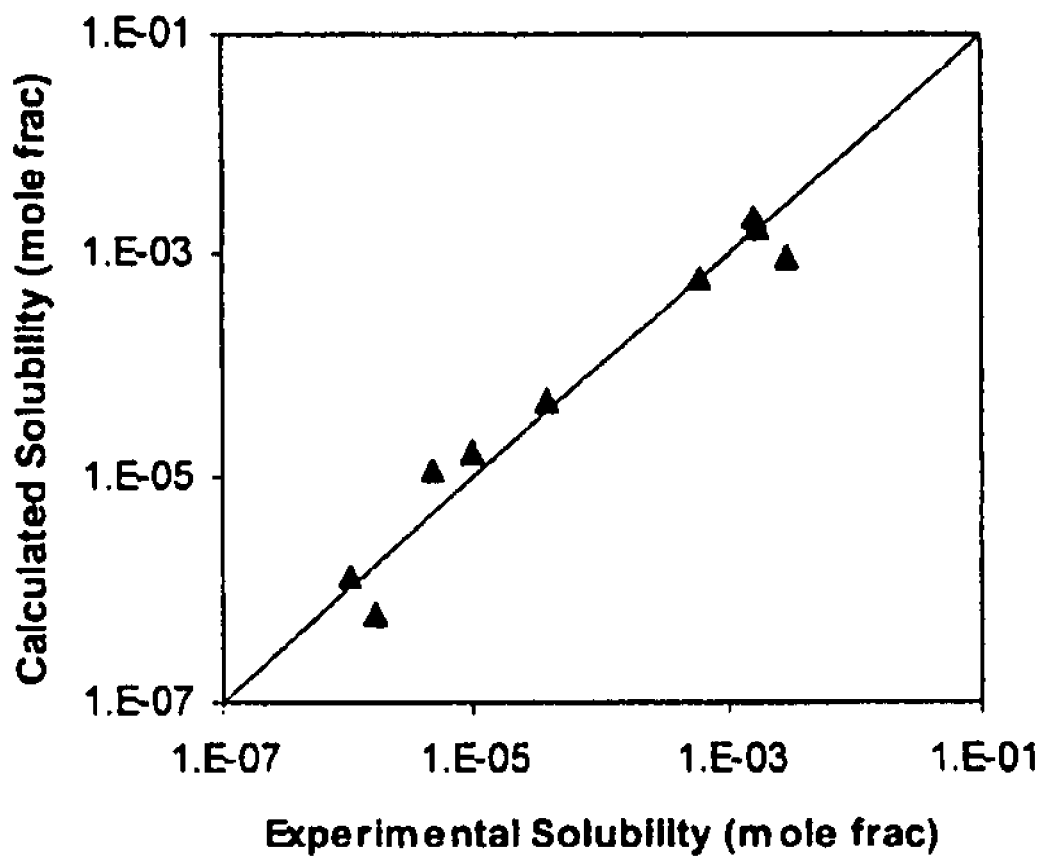
FIG. 16 illustrates a graph showing data of experimental solubilities vs. calculated solubilities for estriol in nine solvents at 298.15K.

FIG. 16 includes a graph illustrating the experimental solubilities vs. calculated solubilities for estriol in 9 solvents at 298.15K. The experimental solubility data was represented well with the NRTL-SAC model. The data for tetrahydrofuran is found to be a very significant outlier and it is not included in the 9 solvents shown in FIG. 16.

Figure 17:
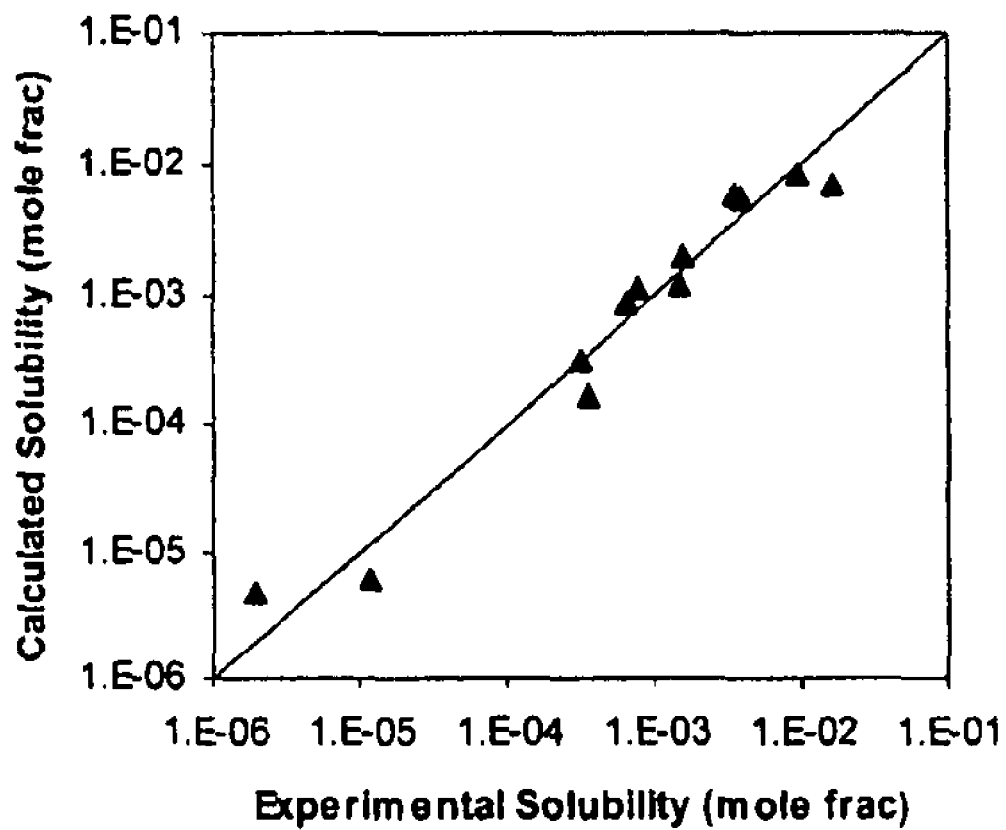
FIG. 17 illustrates a graph showing data of experimental solubilities vs. calculated solubilities for estrone in various solvents at 298.15K.

FIG. 17 includes a graph illustrating the experimental solubilities vs. calculated solubilities for estrone in various solvents at 298.15K. The experimental solubility data was represented well with the NRTL-SAC model.

Figure 18:
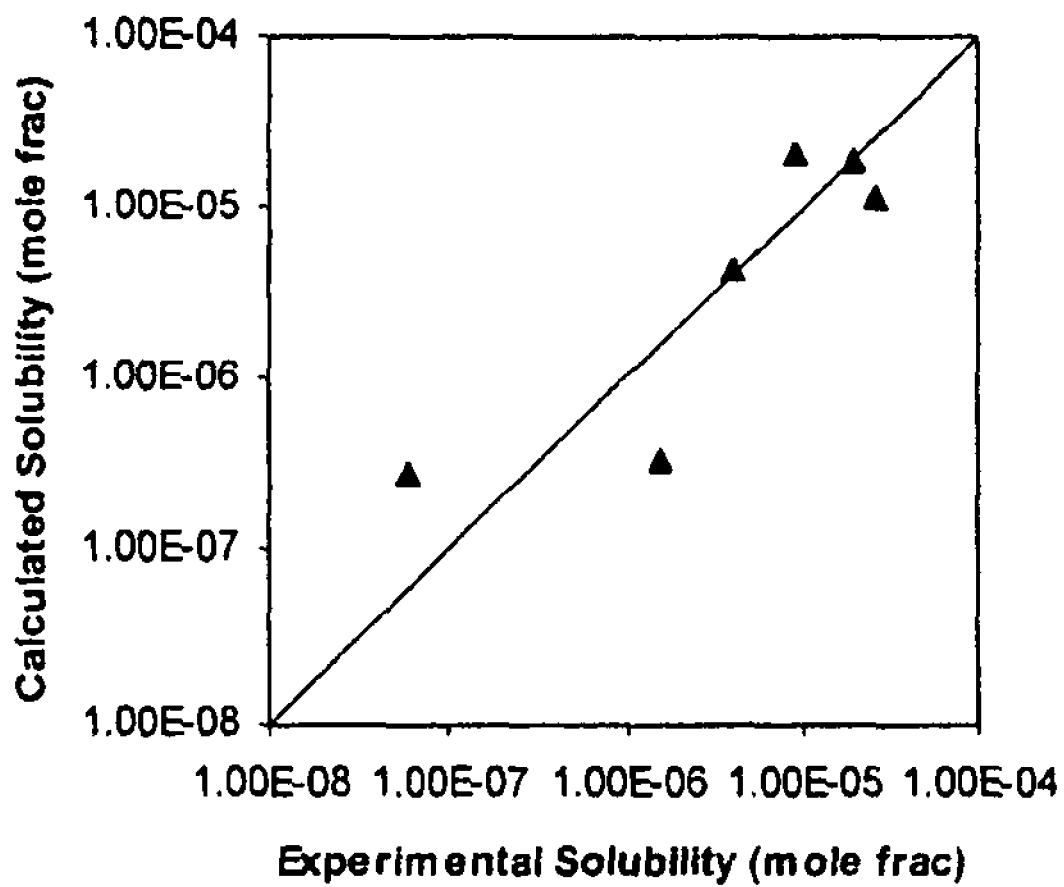
FIG. 18 illustrates a graph showing data of experimental solubilities vs. calculated solubilities for morphine in six solvents at 308.15K.

FIG. 18 includes a graph illustrating the experimental solubilities vs. calculated solubilities for morphine in 6 solvents at 308.15K. Cyclohexane and hexane were outliers. They are very low solubility solvents for morphine and the quality of the data is possibly subject to larger uncertainties.

Figure 19:
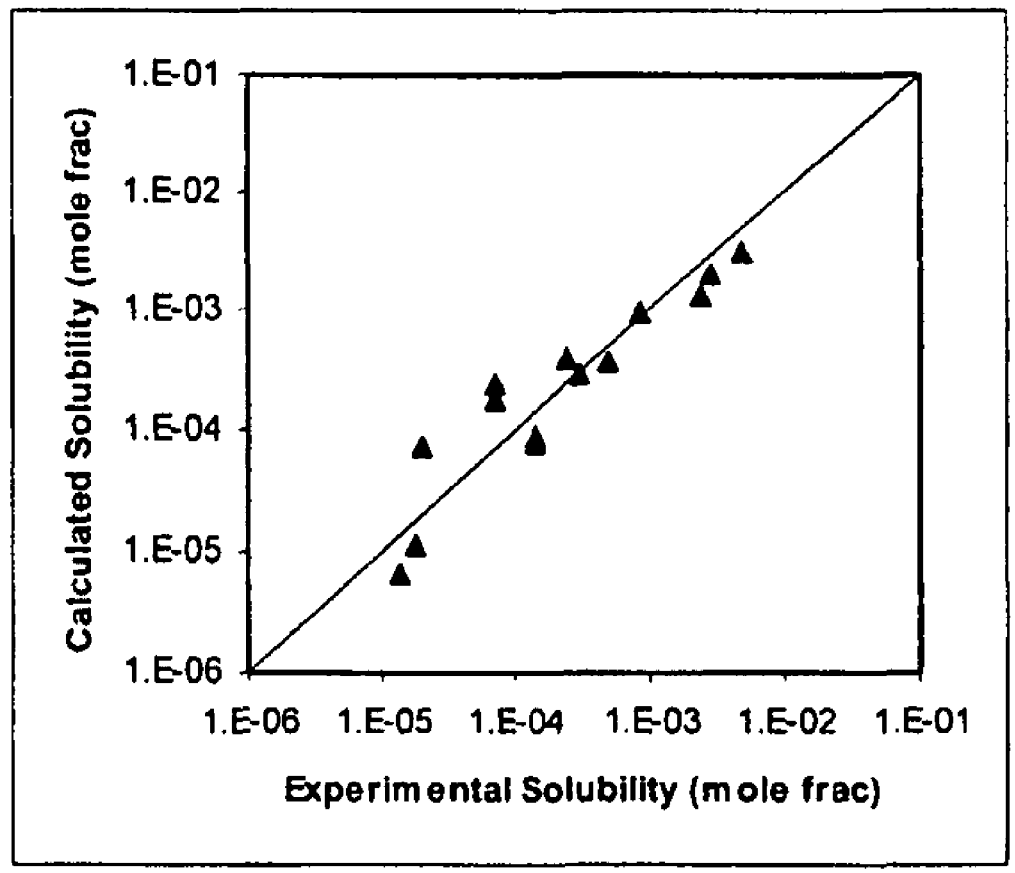
FIG. 19 illustrates a graph showing data of experimental solubilities vs. calculated solubilities for piroxicam in 14 solvents at 298.15K.

FIG. 19 illustrates a graph of the experimental solubilities vs. calculated solubilities for piroxicam in 14 solvents at 298.15K. 1,2-dichloroethane, chloroform, diethyl ether, and N,N-dimethylformamide (DMF) were found to be major outliers and are not included in the 14 solvents shown in FIG. 19. Interestingly, Bustamante, et al. also reported 1,2-dichloroethane, chloroform, and diethyl ether as outliers in their study based on solubility parameter models. P. Bustamante, et al., Partial Solubility Parameters of piroxicam and Niflumic Acid, 1998 INT. J. OF PHARM. 174, 141.

Figure 20:
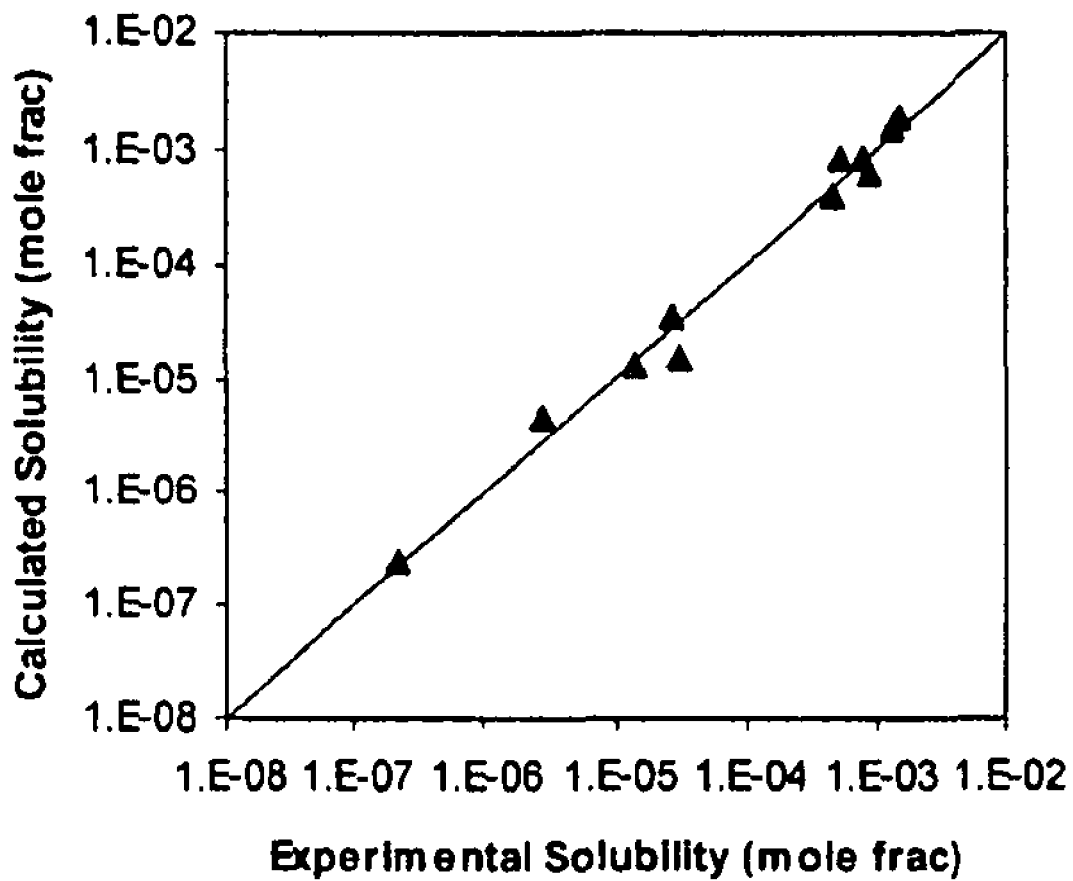
FIG. 20 illustrates a graph showing data of experimental solubilities vs. calculated solubilities for hydrocortisone in 11 solvents at 298.15K.

FIG. 20 illustrates a graph of the experimental solubilities vs. calculated solubilities for hydrocortisone in 11 solvents at 298.15K. Hexane is excluded because of the extreme low solubility of hydrocortisone in hexane which could possibly subject the data to larger uncertainty.

Figure 21:
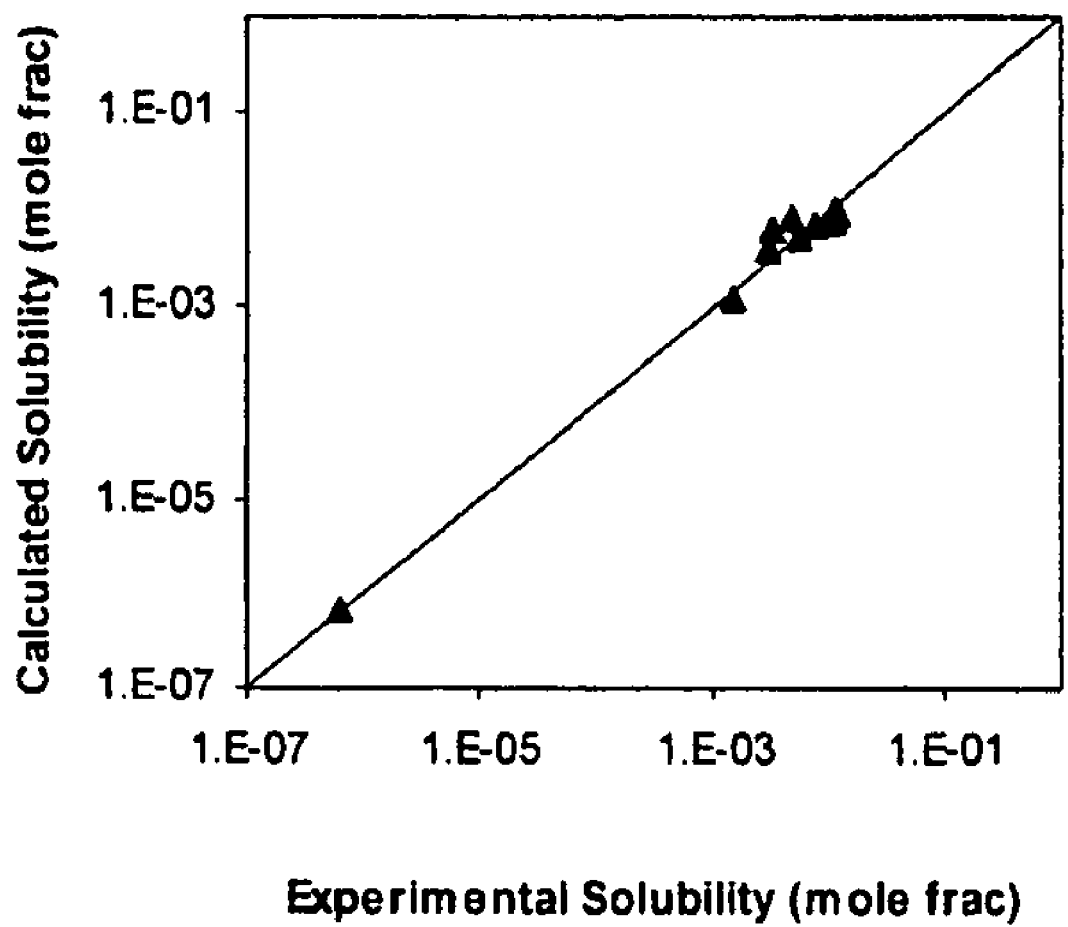
FIG. 21 illustrates a graph showing data of experimental solubilities vs. calculated solubilities for haloperidol in 13 solvents at 298.15K.
Figure 22:
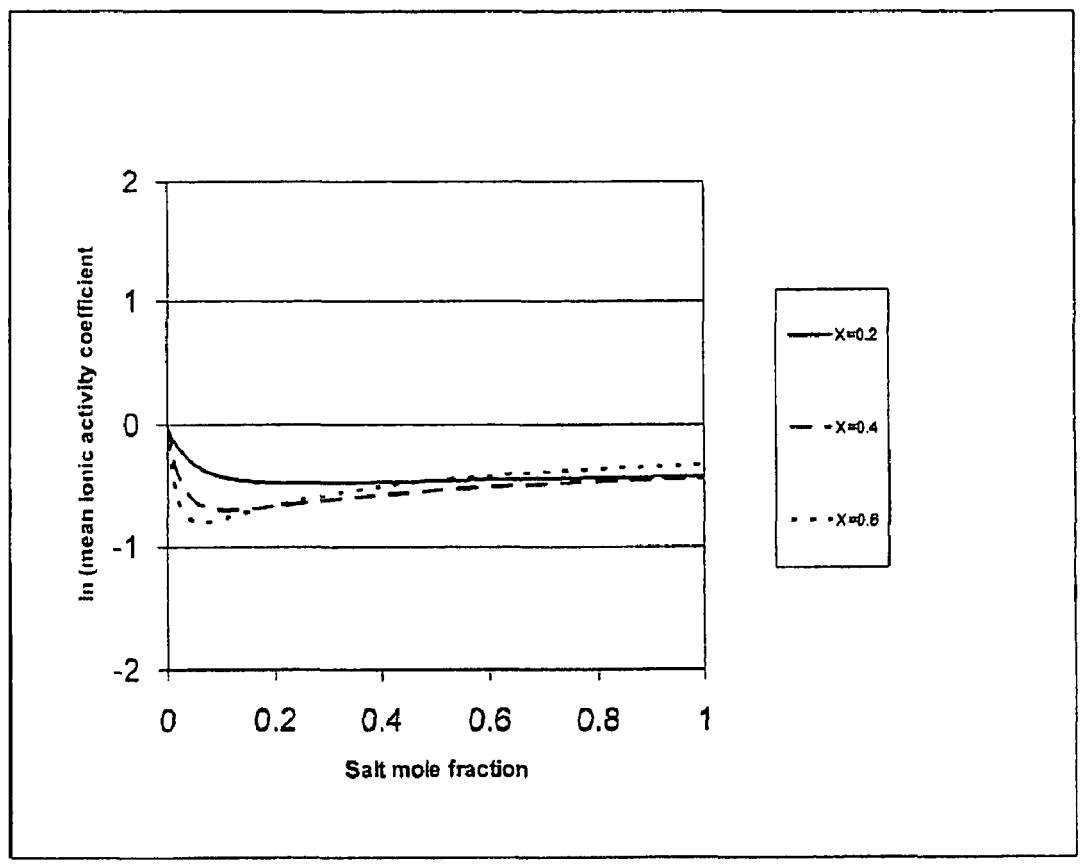
FIG. 22 is a graph illustrating the effect of hydrophobicity parameter X on natural logarithm of mean ionic activity coefficient of aqueous electrolytes with E=1.
Figure 23:
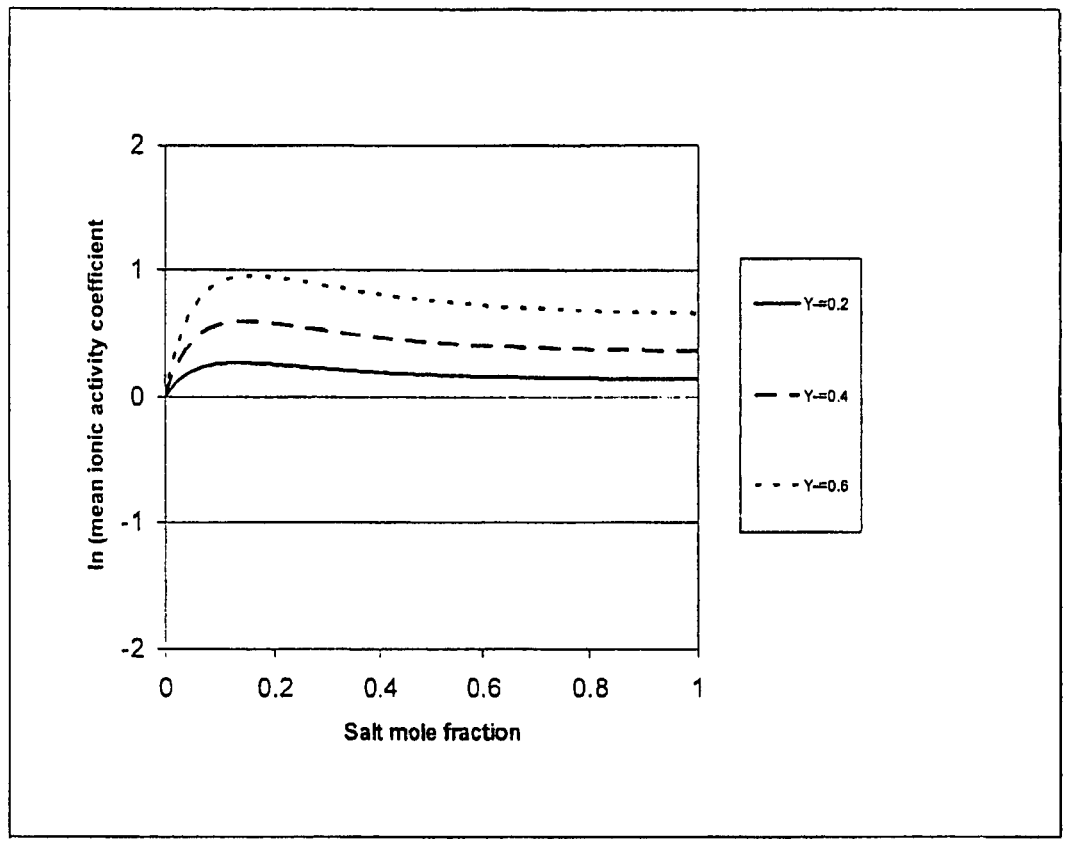
FIG. 23 is a graph illustrating the effect of polarity parameter Y− on natural logarithm of mean ionic activity coefficient of aqueous electrolytes with E=1.
Figure 24:
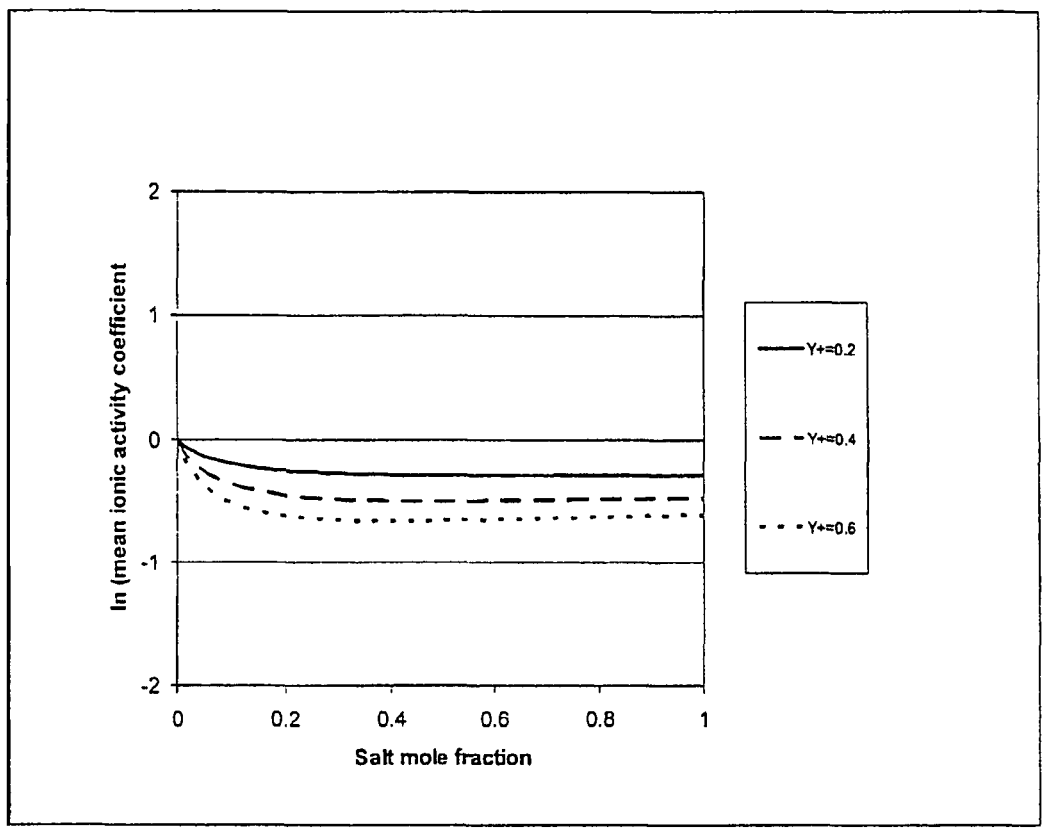
FIG. 24 is a graph illustrating the effect of polarity parameter Y+ on natural logarithm of mean ionic activity coefficient of aqueous electrolytes with E=1.
Figure 25:
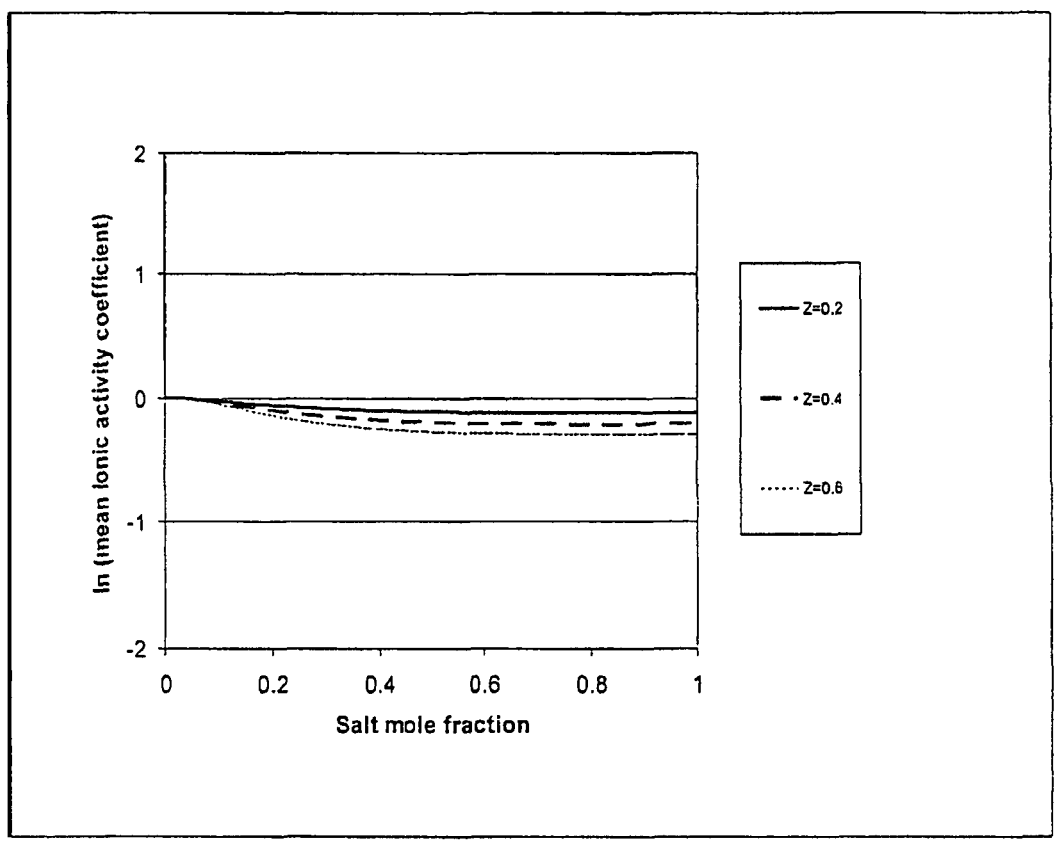
FIG. 25 is a graph illustrating the effect of hydrophilicity parameter E on natural logarithm of mean ionic activity coefficient of aqueous electrolytes with E=1.
Figure 26:
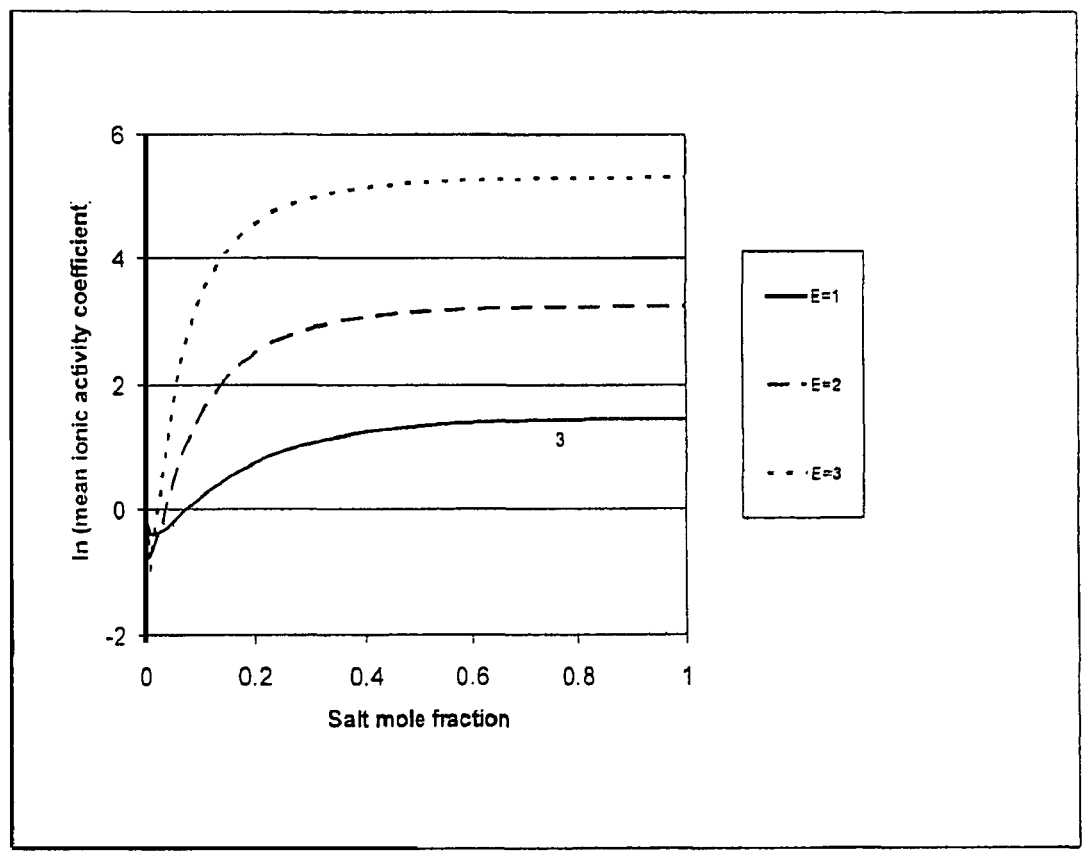
FIG. 26 is a graph illustrating the effect of electrolyte parameter E on natural logarithm of mean ionic activity coefficient of aqueous electrolytes.

FIG. 21 illustrates a graph of the experimental solubilities vs. calculated solubilities for haloperidol in 13 solvents at 298.15K. Haloperidol showed unusually high solubilities in chloroform and DMF and these two solvents are not included in the 13 solvents.

The average RMS error on ln x for the predictions vs. experimental solubility data in Table 4 is 0.37. This corresponds to about ±45% accuracy in solubility predictions.

EXAMPLE 3

Comparison of NRTL-SAC Model to Prior Art Methods for Pharmaceutical Components

The solubilities of various pharmaceutical compounds was modeled with the NRTL-SAC approach of the present invention as well as some prior art models (e.g., the Hanson model and the UNIFAC model) to compare their relative accuracies. The pharmaceutical compounds used included VIOXX®G, ARCOXIA®, Lovastatin, Simvastatin, FOSAMAX®. (Available from Merck & Co., Inc., Whitehouse Station, N.J.). The solvents used included water, N,N-Dimethylformamide ("DMF"), 1-propanol, 2-propanol, 1-butanol, toluene, Chloro-benzene, acetonitrile, ethyl acetate, methanol, ethanol, heptane, acetone, and triethylamine (TEA).

Saturated solutions of the compounds in the solvents were allowed to equilibrate for at least 48 hours. Supernatant fluid was filtered and diluted, and a high pressure liquid chromatography (HPLC) concentration analysis was performed to compare the predicted solubility values with actual solubility values.

The NRTL-SAC model of the present invention gave a RMS error on ln x of about 0.5 (i.e., an accuracy and predictive capability of ±~50%), while the Hansen model had a RMS error on ln x of more than 0.75 and the UNIFAC model had a RMS error on ln x of more than 1.75. Additional comparisons were made for dual-solvent/pharmaceutical systems, and acceptable predictions were obtained from the NRTL-SAC model of the present invention.

These experiments show that the NRTL-SAC model is a simple correlative activity coefficient equation that requires only component-specific molecular parameters (i.e., numbers and types of conceptual segments). Conceptually, the approach suggests that a practitioner account for the liquid ideality of both small solvent molecules and complex pharmaceutical molecules in terms of component-specific molecular parameters (e.g., hydrophobicity, polarity, and hydrophilicity). In practice, these molecular parameters become the adjustable parameters that are determined from selected experimental data. With the development of molecular parameters for solvents and organic solutes, engineering calculations can be performed for various phase equilibrium studies, including solubilities in solvents and solvent mixtures for solvent selection. The NRTL-SAC model provides good qualitative representation on phase behaviors of organic solvents and their complex pharmaceutical solutes and it offers a practical predictive methodology for use in pharmaceutical process design.

EXAMPLE 4

NRTL Segment Activity Coefficient Model

The NRTL-SAC activity coefficient model for component I is composed of the combinatorial term $\gamma_I^C$ and the residual term $\gamma_I^R$:

$$\ln \gamma_I = \ln \gamma_I^C + \ln \gamma_I^R \tag{20}$$

Here the combinatorial term $\gamma_I^C$ is calculated from the Flory-Huggins equation for the combinatorial entropy of mixing. The residual term $\gamma_I^R$ is calculated from the local composition (lc) interaction contribution $\gamma_I^{lc}$ of Polymer NRTL (Chen, C.-C., "A Segment-Based Local Composition Model for the Gibbs Energy of Polymer Solutions," *Fluid Phase Equilibria*, 83:301, 1993) (herein "Chen 1993"). The Polymer NRTL equation incorporates the segment interaction concept and computes activity coefficient for component I in a solution by summing up contributions to activity coefficient from all segments that make up component I. The equation is given as follows:

$$\ln \gamma_I^R = \ln \gamma_I^{lc} = \sum_m r_{m,I} [\ln \Gamma_m^{lc} - \ln \Gamma_m^{lc,I}] \tag{21}$$

with $$\ln \Gamma_m^{lc} = \frac{\sum_j x_j G_{jm} \tau_{jm}}{\sum_k x_k G_{km}} + \sum_{m'} \frac{x_{m'} G_{mm'}}{\sum_k x_k G_{km'}} \left( \tau_{mm'} - \frac{\sum_j x_j G_{jm'} \tau_{jm'}}{\sum_k x_k G_{km'}} \right) \tag{22}$$

$$\ln \Gamma_m^{lc,I} = \frac{\sum_j x_{j,I} G_{jm} \tau_{jm}}{\sum_k x_{k,I} G_{km}} + \sum_{m'} \frac{x_{m',I} G_{mm'}}{\sum_k x_{k,I} G_{km'}} \left( \tau_{mm'} - \frac{\sum_j x_{j,I} G_{jm'} \tau_{jm'}}{\sum_k x_{k,I} G_{km'}} \right) \tag{23}$$

$$x_j = \frac{\sum_I x_I r_{j,I}}{\sum_I \sum_i x_I r_{i,I}} \tag{24}$$

$$x_{j,I} = \frac{r_{j,I}}{\sum_j r_{j,I}}$$

where I is the component index, i, j, k, m, m are the segment species index, x, is the mole fraction of component I, $x_j$ is the segment-based mole fraction of segment species j, $r_{m,I}$ is the number of segment species m contained only in component I, $\gamma_m^{lc}$ is the activity coefficient of segment species m, and $\gamma_m^{lc,I}$ is the activity coefficient of segment species m contained only in component I. G and τ in Eqs. 22 and 23 are local binary quantities related to each other by the NRTL non-random factor parameter α:

$$G = \exp(-\alpha \tau). \tag{25}$$

Four pre-defined conceptual segments were suggested by Chen and Song (2004 above and in parent patent application): one hydrophobic (x), two polar (y− and y+), and one hydrophilic (z). The model molecular parameters, i.e., hydrophobicity X, polarity types Y− and Y+, and hydrophilicity Z, correspond to $r_{m,I}$ (m=x, y−, y+, z), numbers of various conceptual segments in component I.

In the notation used throughout this disclosure, subscript I (upper case) refers to components while subscript i (lower case) refers to segments.

EXAMPLE 5 eNRTL Segment Activity Coefficient Model

The extension of NRTL-SAC model for electrolytes is based on the generalized eNRTL model as summarized by Chen and Song (Chen, C.-C. and Y. Song, "Generalized Electrolyte NRTL Model for Mixed-Solvent Electrolyte Systems," *AIChE J.*, 50.1928, 2004b; herein incorporated by reference) (herein "Chen, 2004b). Here Applicants briefly present the generalized eNRTL model followed by details of the extended NRTL-SAC model of the present invention.

The generalized eNRTL model is applied to correlate mean ionic activity coefficient of mixed-solvent electrolyte systems. The segment interaction concept provides the framework to explicitly account for the attractive interaction of ions with the hydrophilic segments of organic solvents and the repulsive interaction of ions with the hydrophobic segments of organic solvents. In the generalized eNRTL model, any component, electrolyte or solvent, can be defined as an oligomer consisting of various segment species. For instance, an organic electrolyte species can be defined as an oligomer consisting of cationic segment, anionic segment and molecular segment. An organic solvent can be also defined as an oligomer consisting of multiple molecular segments of different nature. Accordingly, with the conventional activity coefficient accounting for the local interaction (Chen, 1993) and the long-range interaction, the model that uses the unsymmetric Pitzer-Debye-Hückel (PDH) formula (Pitzer, K. S., "Electrolytes: From Dilute Solutions to Fused Salts," *J. Am. Chem. Soc.*, 102, 2902 (1980)) (herein "Pitzer, 1980") is calculated as follows:

$$\ln \gamma_I^* = \frac{1}{RT}\left(\frac{\partial G_m^{*ex}}{\partial n_I}\right)_{T,P,n_{i \neq j}} \quad (26)$$

$$= \frac{1}{RT}\left(\frac{\partial G_m^{*ex,lc}}{\partial n_I}\right)_{T,P,n_{i \neq j}} + \frac{1}{RT}\left(\frac{\partial G_m^{*ex,PDH}}{\partial n_I}\right)_{T,P,n_{i \neq j}}$$

or $$\ln \gamma_I^* = \ln \gamma_I^{*lc} + \ln \gamma_I^{*PDH} \quad (27)$$

where I is the component index, "*" denotes the unsymmetric convention, $\gamma_I$ is the activity coefficient of the component I in the mixture; R is the gas constant; T is the temperature; P is the pressure; and $n_I$ is the mole number of the component I in the mixture. The unsymmetric PDH formula, $G_m^{*ex,PDH}$, is obtained by normalization to mole fractions of unity for solvents and zero for electrolytes (Pitzer, K. S., "Thermodynamics of Electrolytes. I: Theoretical and General Equations," *J. Phys. Chem.*, 77, 268 (1973)). The local interaction NRTL model, $G_m^{ex,lc}$, is developed as a symmetric model (Chen, C.-C., "A Segment-Based Local Composition Model for the Gibbs Energy of Polymer Solutions," *Fluid Phase Equilib.*, 83, 301 (1993); and Chen, C.-C., C. P. Bokis, and P. M. Mathias, "A Segment-Based Excess Gibbs Energy Model for Aqueous Organic Electrolyte Systems," *AIChE J.*, 47, 2593 (2001)), based on the symmetrical reference state so that the derived activity coefficient, is $\gamma_I^{lc}=1$ as $x_I \to 1$ for any component (species). The model is then normalized by the unsymmetric reference state (that is, the infinite-dilution activity coefficient in an aqueous or mixed-solvent solution) to obtain the unsymmetric model, $G_m^{*ex,lc}$. Accordingly, the unsymmetric convention activity coefficient is calculated as follows:

$$\ln \gamma_I^{*lc} = \ln \gamma_I^{lc} - \ln \gamma_I^{\infty lc} \quad (28)$$

$$\ln \gamma_I^{*lc} = \ln \gamma_I^{lc} - \ln \gamma_I^{\infty lc} \ln \gamma_I^{lc} = \frac{1}{RT}\left(\frac{\partial G_m^{ex,lc}}{\partial n_I}\right)_{T,P,n_{i \neq j}},$$

$$\gamma_I^{\infty}$$

$$\ln \gamma_I^{lc} = \frac{1}{RT}\left(\frac{\partial G_m^{ex,lc}}{\partial n_I}\right)_{T,P,n_{i \neq j}}, \quad (29)$$

where $\gamma_I^{\infty}$ is the infinite-dilution activity coefficient of the ionic component I in an aqueous or mixed-solvent solution as calculated by Equation 23. A more detailed description on the generalized electrolyte-NRTL model is depicted in Chen, 2004b.

This generalized segment interaction concept is advantageous when one must exactly account for the different interaction characteristics that may be attributed to different molecules, solvents or solutes. The ability to exactly account for such different segment-segment interactions between different species in a system is shown to be key for quantitative correlation of mean ionic activity coefficients in mixed-solvent electrolyte systems. In the generalized eNRTL model, however, it is necessary to account for an electrolyte segment for each and every species separately. Therefore, in a system that involves multiple components, there could be tens of different segments to consider and hundreds of segment-segment interactions to account for, and the computation for activity coefficients becomes much more complicated.

Derived from and improved upon the generalized eNRTL model, the electrolyte extension of NRTL model of the present invention provides one conceptual electrolyte segment. A "conceptual electrolyte segment" herein is one pre-defined electrolyte segment that characterizes the prominent interaction mechanisms between molecules in the liquid phase, that account for the liquid phase nonideality. This pre-defined electrolyte segment is used as a reference against which all electrolyte segments are measured in terms of their liquid phase interaction characteristics. Unlike the generalized eNRTL model, which has no such "conceptual electrolyte segment" as a reference point, surface interaction characteristics of electrolyte segments of the present invention are normalized against the "conceptual electrolyte segment" (in a preferred embodiment, one with interaction characteristics of NaCl) and mathematically expressed as an equivalent number of the reference one. Having a point of reference for the calculation of the electrolyte segment provides a unified and consistent description of liquid phase nonideality of all electrolyte segments and a more intuitive and powerful predictive tool in modeling physical properties including solubility. Together with the numbers of "conceptual" hydrophobic segment, hydrophilic segment and polar segment, the number of "conceptual electrolyte segment" reflects the nature of the surface interactions and their characteristic surface interaction areas that determine their phase behavior.

In the simplest case of a strong electrolyte CA, one may use the following chemical reaction to describe the complete dissociation of the electrolyte:

with $$v_C Z_C = v_A Z_A \quad (31)$$

where $v_C$ is the cationic stoichiometric coefficient, $v_A$ is the anionic stoichiometric coefficient, $Z_C$ is the absolute charge number for cation C, and $Z_A$ is the absolute charge number for anion A.

In applying the segment contribution concept to electrolytes, Applicants introduce a new conceptual electrolyte segment e. This conceptual segment e would completely dissociate to a cationic segment (c) and an anionic segment (a), both of unity charge. Applicants then follow the like-ion repulsion and the electroneutrality constraints imposed by the generalized eNRTL model to derive the activity coefficient equations for ionic segments c and a. All electrolytes, organic or inorganic, symmetric or unsymmetric, univalent or multivalent, are to be represented with this conceptual uni-univalent electrolyte segment e together with previously defined hydrophobic segment, x, polar segments, y– and y+, and hydrophilic segment, z. Due to the fact that Applicants introduce only one (a universally useable one) conceptual electrolyte segment e, the resulting eNRTL-SAC model of the present invention is much simpler than the generalized eNRTL model proposed earlier.

EXAMPLE 6

Solubility of an Electrolyte

Described below is the solubility of an electrolyte by the expression:

$$K_{sp}(T) = \prod_C x_C^{\nu_C,SAT} \gamma_C^{*\nu_C,SAT} \prod_A x_A^{\nu_A,SAT} \gamma_A^{*\nu_A,SAT} \prod_M x_M^{SAT} \gamma_M^{SAT}, \quad (32)$$

where Ksp is the solubility product constant for the electrolyte, T is the temperature of the mixture, $x_C^{\nu_C SAT}$ is the mole fraction of a cation derived from the electrolyte at saturation point of the electrolyte, $x_A^{\nu_A SAT}$ is the mole fraction of an anion derived from the electrolyte at saturation point of the electrolyte, $x_M^{\nu_M SAT}$ is the mole fraction of a neutral molecule derived from the electrolyte at saturation point of the electrolyte, $\gamma_C^{*\nu_C,SAT}$ is the activity coefficient of a cation derived from the electrolyte at the saturation concentration, $\gamma_A^{*\nu_A,SAT}$ is the activity coefficient of an anion derived from the electrolyte at the saturation concentration, $\gamma_M^{*\nu_M,SAT}$ is the activity coefficient of a neutral molecule derived from the electrolyte at the saturation concentration, C is the cation, A is the anion, M is solvent or solute molecule, T is the temperature of the mixture, $\gamma^*$ is the unsymmetric activity coefficient of a species in solution, SAT is saturation concentration, $\nu_C$ is the cationic stoichiometric coefficient, $\nu_A$ is the anionic stoichiometric coefficient, and $\nu_M$ is the neutral molecule stoichiometric coefficient.

A major consideration in the extension of NRTL-SAC for electrolytes is the treatment of reference state for activity coefficient calculations. While the conventional reference state for nonelectrolyte systems is the pure liquid component, the conventional reference state for electrolytes in solution is the infinite-dilution aqueous solution and the corresponding activity coefficient is "unsymmetric."

Following the generalized eNRTL model, the logarithm of unsymmetric activity coefficient of an ionic species, $\ln \gamma_I^*$, is the sum of three terms: the local composition term, $\ln \gamma_I^{*lc}$, the Pitzer-Debye-Hückel term, $\ln \gamma_I^{*PDH}$, and the Flory-Huggins term, $\ln \gamma_I^{*FH}$.

$$\ln \gamma_I^* = \ln \gamma_I^{*lc} + \ln \gamma_I^{*PDH} + \ln \gamma_I^{*FH} \quad (33)$$

Eq. 33 applies to aqueous electrolyte systems where water is a sole solvent within the solution. For mixed-solvent solutions, the Born term, $\Delta \ln \gamma_I^{Born}$, is used to correct the change of the infinite dilution reference state from the mixed-solvent composition to the aqueous solution for the Pitzer-Debye-Hückel term:

$$\ln \gamma_I^* = \ln \gamma_I^{*lc} + \ln \gamma_I^{*PDH} + \ln \gamma_I^{*FH} + \Delta \ln \gamma_I^{Born} \quad (34)$$

Since Applicants adopt the aqueous phase infinite dilution reference state for $\gamma_I^*$, the Born term correction is required for non-aqueous systems.

With the introduction of the conceptual electrolyte segment e and the corresponding conceptual ionic segments c and a, one can rewrite Eq. 34 in terms of contributions from all conceptual segments:

$$\ln \gamma_I^* = \ln \gamma_I^{*lc} + \ln \gamma_I^{*PDH} + \ln \gamma_I^{*FH} + \Delta \ln \gamma_I^{Born} \quad (35)$$

$$= \sum_m r_{m,I}(\ln \Gamma_m^{*lc} + \ln \Gamma_m^{*PDH}) + r_{c,I}(\ln \Gamma_c^{*lc} + \ln \Gamma_c^{*PDH} + \Delta \ln \Gamma_c^{Born}) +$$

$$r_{a,I}(\ln \Gamma_a^{*lc} + \ln \Gamma_a^{*PDH} + \Delta \ln \Gamma_a^{Born}) + \ln \gamma_I^{*FH}$$

where r is the segment number, m is the conceptual molecular segment index (i.e., m=x, y−, y+, z), c and a are cationic and anionic segments, respectively, resulting from the dissociation of the conceptual electrolyte segment e. Also notice that in Eq. 35, unlike the local composition term and the long range ion-ion interaction terms, the Flory-Huggins term remains as the component-based contribution.

For systems of single electrolyte CA with a segment number $r_e$, $r_c$ and $r_a$ must satisfy electroneutrality and they can be computed from $r_e$, $Z_C$, and $Z_A$.

$$r_{c,C} = r_{e,CA} Z_C \quad (36)$$

$$r_{a,A} = r_{e,CA} Z_A \quad (37)$$

For systems of multiple electrolytes, the mixing rule is needed to compute segment number $r_c$ and $r_a$ for each cation C and anion A.

$$r_{c,C} = \sum_A r_{e,CA} Z_C \left( x_A Z_A \Big/ \sum_{A'} x_{A'} Z_{A'} \right) \quad (38)$$

$$r_{a,A} = \sum_C r_{e,CA} Z_A \left( x_C Z_C \Big/ \sum_{C'} x_{C'} Z_{C'} \right) \quad (39)$$

$r_{e,CA}$, the number of conceptual electrolyte segment e in electrolyte CA, becomes the new model parameter for electrolytes. For the sake of brevity, Applicants call $r_{e,CA}$ parameter E, the electrolyte segment number.

EXAMPLE 7

Local Composition Interaction Contribution

To derive the expression for the local composition interaction contribution, Applicants simplify the generalized excess Gibbs energy expression of the prior Chen and Song model (Chen, 2004b) for systems with multiple molecular segments m and single electrolyte segment e. The single electrolyte segment e is then decomposed into a cationic segment c and an anionic segment a:

$$\frac{G^{ex,lc}}{nRT} = \sum_I \left[ \sum_m r_{m,I} x_I \left( \frac{\sum_j x_j G_{jm} \tau_{jm}}{\sum_k x_k G_{km}} \right) + r_{c,I} x_I \left( \frac{\sum_j x_j G_{jc,ac} \tau_{jc,ac}}{\sum_k x_k G_{kc,ac}} \right) + r_{a,I} x_I \left( \frac{\sum_j x_j G_{ja,ca} \tau_{ja,ca}}{\sum_k x_k G_{ka,ca}} \right) \right] \quad (40)$$

with $$x_j = \frac{\sum_l x_l r_{j,l}}{\sum_l \sum_i x_l r_{i,l}} \quad i, j = m, c, a \tag{41}$$

where $G^{ex,lc}$ is the excess Gibbs energy from local composition interactions, n is the total mole number, R is the gas constant and T is the temperature.

To derive the segment activity coefficient, one can rewrite Eq. 40 as follows:

$$\frac{G^{ex,lc}}{n_S RT} = \sum_m x_m \left( \frac{\sum_j x_j G_{jm} \tau_{jm}}{\sum_k x_k G_{km}} \right) + x_c \left( \frac{\sum_j x_j G_{jc,ac} \tau_{jc,ac}}{\sum_k x_k G_{kc,ac}} \right) + x_a \left( \frac{\sum_j x_j G_{ja,ca} \tau_{ja,ca}}{\sum_k x_k G_{ka,ca}} \right) \tag{42}$$

where $n_S$ is the total number of all segments. Accordingly, the segment activity coefficient can be calculated as follows:

$$\ln \Gamma_j^{lc} = \frac{1}{RT} \left( \frac{\partial G^{ex,lc}}{\partial n_j} \right)_{T,P,n_{i \neq j}} \tag{43}$$

$$i, j = m, c, a$$

Specifically, the activity coefficients from Eq. 43 for molecular segments, cationic segment, and anionic segment can be carried out as follows:

$$\ln \Gamma_m^{lc} = \frac{\sum_j x_j G_{jm} \tau_{jm}}{\sum_k x_k G_{km}} + \sum_{m'} \frac{x_{m'} G_{mm'}}{\sum_k x_k G_{km'}} \left( \tau_{mm'} - \frac{\sum_j x_j G_{jm'} \tau_{jm'}}{\sum_k x_k G_{km'}} \right) + \frac{x_c G_{mc,ac}}{\sum_k x_k G_{kc,ac}} \left( \tau_{mc,ac} - \frac{\sum_j x_j G_{jc,ac} \tau_{jc,ac}}{\sum_k x_k G_{kc,ac}} \right) + \frac{x_a G_{ma,ca}}{\sum_k x_k G_{ka,ac}} \left( \tau_{ma,ca} - \frac{\sum_j x_j G_{ja,ca} \tau_{ja,ca}}{\sum_k x_k G_{ka,ca}} \right) \tag{44}$$

$$\ln \Gamma_c^{lc} = \sum_m \frac{\sum_j x_m G_{cm}}{\sum_k x_k G_{km}} \left( \tau_{cm} - \frac{\sum_j x_j G_{jm} \tau_{jm}}{\sum_k x_k G_{km}} \right) + \frac{\sum_j x_j G_{jc,ac} \tau_{jc,ac}}{\sum_k x_k G_{kc,ac}} - \frac{x_a}{\sum_k x_k G_{ka,ca}} \left( \frac{\sum_j x_j G_{ja,ca} \tau_{ja,ca}}{\sum_k x_k G_{ka,ca}} \right) \tag{45}$$

$$\ln \Gamma_a^{lc} = \sum_m \frac{\sum_j x_m G_{am}}{\sum_k x_k G_{km}} \left( \tau_{am} - \frac{\sum_j x_j G_{jm} \tau_{jm}}{\sum_k x_k G_{km}} \right) + \frac{\sum_j x_j G_{ja,ca} \tau_{ja,ca}}{\sum_k x_k G_{ka,ca}} - \frac{x_c}{\sum_k x_k G_{kc,ac}} \left( \frac{\sum_m x_m G_{mc,ac} \tau_{mc,ac}}{\sum_k x_k G_{kc,ac}} \right) \tag{46}$$

The local composition term for the logarithm of activity coefficient of component I is computed as the sum of the individual segment contributions.

$$\ln \gamma_I^{lc} = \sum_i r_{i,I} \ln \Gamma_i^{lc} \quad i = m, c, a \tag{47}$$

$$= \sum_m r_{m,I} \ln \Gamma_m^{lc} + r_{c,I} \ln \Gamma_c^{lc} + r_{a,I} \ln \Gamma_a^{lc}$$

However, the activity coefficient by Eq. 47 needs to be further normalized so that $\gamma_I^{lc} = 1$ as $x_I \to 1$ for any component; this is the so-called symmetric reference state. The normalization can be done as follows:

$$\ln \gamma_I^{lc} = \sum_i r_{i,I} [\ln \Gamma_i^{lc} - \ln \Gamma_i^{lc,I}] \quad i = m, c, a \tag{48}$$

$$= \sum_m r_{m,I} [\ln \Gamma_m^{lc} - \ln \Gamma_m^{lc,I}] + r_{c,I} [\ln \Gamma_c^{lc} - \ln \Gamma_c^{lc,I}] + r_{a,I} [\ln \Gamma_a^{lc} - \ln \Gamma_a^{lc,I}]$$

Here $\Gamma_i^{lc,I}$ is the activity coefficient of the segment i contained in the symmetric reference state of component I; it can be calculated from Eqs. 44-46 by setting $x_I=1$:

$$\ln \Gamma_i^{lc,I} = \ln \Gamma_i^{lc}(x_I=1) \quad i=m,c,a \tag{49}$$

Finally, the unsymmetric convention in Eq. 34 requires us to compute the infinite-dilution activity coefficient, $\gamma_I^{\infty lc}$, for a component:

$$\ln \gamma_I^{*lc} = \ln \gamma_I^{lc} - \ln \gamma_I^{\infty lc} \tag{50}$$

with $$\ln \gamma_I^{\infty lc} = \sum_i r_{i,I} [\ln \Gamma_i^{\infty lc} - \ln \Gamma_i^{lc,I}] \quad i = m, c, a \tag{51}$$

$$= \sum_m r_{m,I} [\ln \Gamma_m^{\infty lc} - \ln \Gamma_m^{lc,I}] + r_{c,I} [\ln \Gamma_c^{\infty lc} - \ln \Gamma_c^{lc,I}] + r_{a,I} [\ln \Gamma_a^{\infty lc} - \ln \Gamma_a^{lc,I}]$$

Combining Eqs. 48 and 51, one can obtain:

$$\ln \gamma_I^{*lc} = \ln \gamma_I^{lc} - \ln \gamma_I^{\infty lc} \tag{52}$$

$$= \sum_i r_{i,I} [\ln \Gamma_i^{lc} - \ln \Gamma_i^{\infty lc}] \quad i = m, c, a$$

$$= \sum_m r_{m,I} [\ln \Gamma_m^{lc} - \ln \Gamma_m^{\infty lc}] + r_{c,I} [\ln \Gamma_c^{lc} - \ln \Gamma_c^{\infty lc}] + r_{a,I} [\ln \Gamma_a^{lc} - \ln \Gamma_a^{\infty lc}]$$

$$= \sum_m r_{m,I} \ln \Gamma_m^{*lc} + r_{c,I} \ln \Gamma_c^{*lc} + r_{a,I} \ln \Gamma_a^{*lc}$$

with $$\ln \Gamma_m^{*lc} = \ln \Gamma_m^{lc} - \ln \Gamma_m^{\infty lc} \tag{53}$$

$$\ln \Gamma_c^{*lc} = \ln \Gamma_c^{lc} - \ln \Gamma_c^{\infty lc} \tag{54}$$

$$\ln \Gamma_a^{*lc} = \ln \Gamma_a^{lc} - \ln \Gamma_a^{\infty lc} \tag{55}$$

Because Applicants adopt the aqueous phase infinite dilution reference state, the infinite-dilution activity coefficients of conceptual segments can be calculated from Eqs. 44-47 by setting $x_w=1$:

$$\ln \Gamma_i^{\infty lc} = \ln \Gamma_i^{lc}(x_W=1) \quad i=m,c,a \tag{56}$$

where $x_W$ is the mole fraction of water in the solution.

EXAMPLE 8

Long-Range Interaction Contribution from Pitzer-Debye-Hückel (PDH) Model

To account for the long-range ion-ion interactions, the present invention eNRTL-SAC model uses the unsymmetric Pitzer-Debye-Hückel (PDH) formula (Pitzer, 1980) on the segment basis:

$$\frac{G^{*ex,PDH}}{n_S RT} = \left(\frac{1000}{\overline{M}_S}\right)^{1/2} \left(\frac{4A_\varphi I_x}{\rho}\right) \ln(1 + \rho I_x^{1/2}) \qquad (57)$$

with $$A_\varphi = 1/3 \left(\frac{2\pi N_A \overline{d}_S}{1000}\right)^{1/2} \left(\frac{Q_e^2}{\overline{\varepsilon}_S k_B T}\right)^{3/2} \qquad (58)$$

$$I_x = 1/2 \sum_i x_i z_i^2 \qquad (59)$$

where $A_\varphi$ is the Debye-Hückel parameter, $I_x$ is the ionic strength (segment mole fraction scale), $\overline{M}_S$ is the average molecular weight of the mixed-solvents, $\rho$ is the closest approach parameter, $N_A$ is the Avogadro's number, $\overline{d}_S$ is the average density of the mixed-solvents, $Q_e$ is the electron charge, $\overline{\varepsilon}_S$ is the average dielectric constant of the mixed-solvents, $k_B$ is the Boltzmann constant, and $z_i$ ($z_m=0$; $z_c=z_a=1$) is the charge number of segment-based species i.

Applying the PDH model to the conceptual segments, the activity coefficient of segment species i can be derived as follows:

$$\ln \Gamma_i^{*PDH} = \frac{1}{RT}\left(\frac{\partial G^{*ex,PDH}}{\partial n_i}\right)_{T,P,n_{j \neq i}} \quad i, j = m, c, a \qquad (60)$$

$$= -\left(\frac{1000}{\overline{M}_S}\right)^{1/2} A_\varphi \left[\left(\frac{2z_i^2}{\rho}\right)\ln(1 + \rho I_x^{1/2}) + \frac{z_i^2 I_x^{1/2} - 2I_x^{3/2}}{1 + \rho I_x^{1/2}}\right]$$

The unsymmetric long range term for the logarithm of activity coefficient of component I is the sum of contributions from its various segments:

$$\ln \gamma_I^{*PDH} = \sum_m r_{m,I} \ln \Gamma_m^{*PDH} + r_{c,I} \ln \Gamma_c^{*PDH} + r_{a,I} \ln \Gamma_a^{*PDH} \qquad (61)$$

where $$\ln \Gamma_m^{*PDH} = 2\left(\frac{1000}{\overline{M}_S}\right)^{1/2} \frac{A_\varphi I_x^{3/2}}{1 + \rho I_x^{1/2}} \qquad (62)$$

$$\ln \Gamma_c^{*PDH} = \ln \Gamma_a^{*PDH} \qquad (63)$$

$$= -\left(\frac{1000}{\overline{M}_S}\right)^{1/2} A_\varphi \left[\left(\frac{2}{\rho}\right)\ln(1 + \rho I_x^{1/2}) + \frac{I_x^{1/2} - 2I_x^{3/2}}{1 + \rho I_x^{1/2}}\right]$$

With $$A_\varphi = 1/3\left(\frac{2\pi N_A \overline{d}_S}{1000}\right)^{1/2}\left(\frac{Q_e^2}{\overline{\varepsilon}_S k_B T}\right)^{3/2} \qquad (64)$$

$$I_x = \frac{1}{2}(x_c + x_a) \qquad (65)$$

The Debye-Hückel theory is based on the infinite dilution reference state for ionic species in the actual solvent media. For systems with water as the only solvent, the reference state is the infinite dilution aqueous solution. For mixed-solvent systems, the reference state for which the Pitzer-Debye-Hückel formula remains valid is the infinite dilution solution with the corresponding mixed-solvent composition. Consequently, the molecular quantities for the single solvent need to be extended for mixed-solvents; simple composition average mixing rules are adequate to calculate them as follows:

$$\overline{M}_S = \sum_S x'_S M_S \qquad (66)$$

$$\frac{1}{\overline{d}_S} = \sum_S \frac{x'_S}{d_S} \qquad (67)$$

$$\overline{\varepsilon}_S = \sum_S w'_S \varepsilon_S \qquad (68)$$

with $$x'_S = \frac{x_S}{\sum_S x_S} \qquad (69)$$

$$w'_S = \frac{M_S x_S}{\sum_S M_S x_S} \qquad (70)$$

where S is a solvent component in the mixture, and $M_S$ is the molecular weight of the solvent S. It should be pointed out that Eqs. 66-70 should be used only in Eq. 54 and $\overline{M}_S$, $\overline{d}_S$, and $\overline{\varepsilon}_S$ were already assumed as constants in Eqs. 57 and 58 when deriving Eq. 60 for mixed-solvent systems. Table 1 shows the values of dielectric constant at 298.15 K used in this study for the same sixty-two solvents investigated by Chen and Song (Chen, 2004a and U.S. Publication No. 2005/0187748) above. These values were compiled from various sources including internet websites and commercial software Aspen Properties v2004.1 (by Aspen Technology, Inc. of Cambridge, Mass., assignee of the present invention).

EXAMPLE 9

Born Term Correction to Activity Coefficient

Given that the infinite dilution aqueous solution is chosen as the reference state, one needs to correct the change of the reference state from the mixed-solvent composition to aqueous solution for the Pitzer-Debye-Hückel term. The Born term (Robinson, R. A. and R. H. Stokes, *Electrolyte Solutions*, 2$^{nd}$ ed., Butterworths (1970), Rashin, A. A. and B. Honig, "Reevaluation of the Born Model of Ion Hydration, *J. Phys. Chem.*, 89: 5588 (1985)) on the segment basis is used for this purpose:

$$\frac{\Delta G^{Born}}{n_S RT} = \frac{Q_e^2}{2k_B T}\left(\frac{1}{\overline{\varepsilon}_S} - \frac{1}{\varepsilon_W}\right)\sum_i \frac{x_i z_i^2}{r_i} 10^{-2} \qquad (71)$$

$\Delta G^{Born}$ is the Born term correction to the unsymmetric Pitzer-Debye-Hückel formula $G^{*ex,PDH}$, $\varepsilon_W$ is the dielectric constant of water, and $r_i$ is the Born radius of segment specie i.

Applying Eq. 65 to all conceptual segments, the corresponding expression for the activity coefficient of segment species i can be derived as follows:

$$\Delta \ln \Gamma_m^{Born} = \frac{1}{RT}\left(\frac{\partial \Delta G^{Born}}{\partial n_m}\right)_{T,P,n_{j \neq m}} \qquad (72)$$

$$= 0 \quad m = x, y-, y+, z$$

-continued $$\Delta \ln \Gamma_i^{Born} = \frac{1}{RT}\left(\frac{\partial \Delta G^{Born}}{\partial n_i}\right)_{T, P, n_{j \neq i}} \quad (73)$$

$$= \frac{Q_e^2}{2k_B T}\left(\frac{1}{\bar{\varepsilon}_S} - \frac{1}{\varepsilon_W}\right)\frac{z_i^2}{r_i}10^{-2}$$

$$i = c, a$$

The Born correction term on the logarithm of activity coefficient of component I is the sum of contributions from its various segments:

$$\Delta \ln \gamma_I^{Born} = r_{r,I}\Delta \ln \Gamma_c^{Born} + r_{a,I}\Delta \ln \Gamma_a^{Born} \quad (74)$$

$$\Delta \ln \Gamma_c^{Born} = \frac{Q_e^2}{2k_B T}\left(\frac{1}{\bar{\varepsilon}_S} - \frac{1}{\varepsilon_W}\right)\frac{1}{r_c}10^{-2} \quad (75)$$

$$\Delta \ln \Gamma_a^{Born} = \frac{Q_e^2}{2k_B T}\left(\frac{1}{\bar{\varepsilon}_S} - \frac{1}{\varepsilon_W}\right)\frac{1}{r_a}10^{-2} \quad (76)$$

EXAMPLE 10

Flory-Huggins Term Correction to Activity Coefficient

Although in most common electrolyte systems, the combinatorial entropy of mixing term is much smaller than the residual term, one may still want to include it in a general model. Applicants follow the Polymer NRTL model (Chen 1993 above) and use the Flory-Huggins term to describe the combinatorial term:

$$\frac{G^{ex,FH}}{nRT} = \sum_I x_I \ln\left(\frac{\phi_I}{x_I}\right) \quad (77)$$

with $$\phi_I = \frac{x_I r_I}{\sum_J x_J r_J} \quad (78)$$

where $G^{ex,FH}$ is the Flory-Huggins term for the excess Gibbs energy, $\phi_I$ is the segment fraction of component I, and $r_I$ is the number of all conceptual segments in component I:

$$r_I = \sum_m r_{m,I} + r_{c,I} + r_{a,I} \quad (79)$$

The activity coefficient of component I from the combinatorial term can be derived from Eq. 66:

$$\ln \gamma_I^{FH} = \ln\left(\frac{\phi_I}{x_I}\right) + 1 - r_I \sum_J \frac{\phi_J}{r_J} = \ln\left(\frac{r_I}{\sum_J x_J r_J}\right) + 1 - \frac{r_I}{\sum_J x_J r_J} \quad (80)$$

The infinite-dilution activity coefficient of a component in water is:

$$\ln \gamma_I^{\infty FH} = \ln\left(\frac{r_I}{r_W}\right) + 1 - \frac{r_I}{r_W} \quad (81)$$

In both NRTL-SAC (parent patent application) and present invention eNRTL-SAC, water is selected as the reference for the hydrophilic segment z. Therefore, one can set $r_W=1$. Thus, one has:

$$\ln \gamma_I^{\infty FH} = \ln r_I + 1 - r_I \quad (82)$$

One can then compute the unsymmetric activity coefficient from the Flory-Huggins term as follows:

$$\ln \gamma_I^{*,FH} = \ln \gamma_I^{FH} - \ln \gamma_I^{\infty FH} = r_I - \ln\left(\sum_J x_J r_J\right) - \frac{r_I}{\sum_J x_J r_J} \quad (83)$$

EXAMPLE 11

NRTL Binary Parameters

In Eqs. 20 and 21 for NRTL-SAC, the model formulation requires the asymmetric interaction energy parameters, τ, and the symmetric nonrandom factor parameters, α, for each binary pair of the conceptual segments. In Eqs. 44-46 for eNRTL-SAC of the present invention, one needs additional binary parameters of τ and α between conceptual molecular segments, m and ionic segments, c or a. In practice, Applicants fix the values of α's for the binary pairs of molecular segment and ionic segment to the single value of 0.2 while the values of τ for the binary pairs of molecular segment and ionic segment are calculated from the τ's for the binary pairs of molecular segment and electrolyte segment. Following the same scheme in generalized eNRTL (Chen and Song, 2004b above), one can calculate these binary interaction energy parameters as follows:

$$\tau_{cm} = \tau_{am} = \tau_{em} \quad (84)$$

$$\tau_{mc,ac} = \tau_{ma,ca} = \tau_{me} \quad (85)$$

Following the treatment of NRTL-SAC (disclosed in U.S. Publication No. 2005/0187748), Applicants identify a reference electrolyte for the conceptual electrolyte segment e. In searching for the reference electrolyte, Applicants choose one elemental electrolyte that has abundant literature data. In one example study, NaCl is used as the reference electrolyte for e. The ionic radii for sodium ion and chloride ion are 1.680× $10^{-10}$ m and 1.937×$10^{-10}$ m, respectively. With NaCl as the reference electrolyte, the energy parameters for the z-e pair are set to (8.885, −4.549) for the water-NaCl pair. The energy parameters for the x-e pair are set to (15, 5), in line with the parameters identified for $C_2H_4$—NaCl pair earlier by Chen and Song (Chen, 2004b). The energy parameters for the y-e pairs are set to (12, −3) after limited trials to optimize the performance of the model in this study. The complete set of NRTL binary interaction energy parameters are given in Table 6. Other choices of the reference electrolyte and parameter values may be suitable. The below reports the general behavior of the present invention eNRTL-SAC model based on the parameters reported in Table 6.

The electrolyte segment e is the only extra molecular descriptor and the electrolyte parameter E is the only extra molecular parameter for all electrolytes, inorganic or organic. All local and long range interactions derived from the existence of cationic and anionic species of various ionic charge valence, radius, chemical make-up, etc., are to be accounted for with this extra molecular descriptor for electrolytes together with combinations of conceptual molecular segments, i.e., hydrophobicity, polarity and hydrophilicity. In other words, every electrolyte, organic or inorganic, are modeled as combinations of E, X, Y, and Z. As such, electrolytes are recognized as "hydrophobic" electrolytes, "polar" electrolytes, "hydrophilic" electrolytes, and their various combinations. Likewise, ionic activity coefficient of each ionic species will be computed from its share of E, X, Y, and Z. The ions are to be considered as "hydrophobic" ions, "polar" ions, or "hydrophilic" ions.

FIGS. 22 to 26 show effects of the molecular parameters on mean ionic activity coefficients (mole fraction scale) of the reference electrolyte, i.e., electrolyte with E=1. As shown in FIGS. 22 to 26, hydrophobicity parameter X brings down the mean ionic activity coefficient at low electrolyte concentration but in a rather nonlinear way. Polarity parameter Y− raises the mean ionic activity coefficient while polarity parameter Y+ lowers the mean ionic activity coefficient. Hydrophilicity parameter Z has a relatively slight downshift effect on the mean ionic activity coefficient. Electrolyte parameter E brings down the mean ionic activity coefficient at low electrolyte concentration and pushes up the mean ionic activity coefficient at high electrolyte concentration.

Experimental data for ionic activity coefficients are not readily available though emerging (Wilczek-Vera, G. et al, "On the Activity of Ions and the Junction Potential: Revised Values for All Data," *AIChE J.*, 50:445, 2004). Given the fact that existing experimental data are limited to mean ionic activity coefficient for neutral electrolytes, Applicants are not able to directly identify the molecular parameters for ionic species. In preparing FIGS. 22 to 26 discussed above and the subsequent studies reported in the Model Applications section below, Applicants use Eqs. 36-37 to determine from electrolyte parameter E the ionic segment numbers for the ions and Applicants arbitrarily assign molecular segment parameters (X, Y−, Y+, and Z) only to the anion. This practice is acceptable since virtually all electrolytes investigated in this study are electrolytes with elemental cations.

Limited amount of mean ionic activity coefficient data are available in the public literature for aqueous electrolytes. Applicants test the eNRTL-SAC model 20 as shown in FIG. 3 against mean ionic activity coefficient data of aqueous electrolyte systems. In addition, Applicants test the eNRTL-SAC model against salt solubility data in multiple solvents for a number of inorganic electrolytes and organic electrolytes. To the best of Applicants' knowledge, public literature data is very scarce for such salt solubility data. Proprietary solubility data from industrial collaborators was also used to test the applicability of the eNRTL-SAC model. However, results with such proprietary solubility data are not included in this discussion.

EXAMPLE 12

Mean Ionic Activity Coefficients in Aqueous Systems

For an electrolyte CA that dissociates to cation C and anion A, the mean ionic activity coefficients $\gamma_\pm^*$ is related to individual ionic activity coefficients as follows:

$$\ln \gamma_\pm^* = \frac{1}{\nu}(\nu_C \ln \gamma_C^* + \nu_A \ln \gamma_A^*) \quad (86)$$

where $\nu = \nu_C + \nu_A$.

Equation 83 gives the mean ionic activity coefficient on the mole fraction scale and it can be converted to the molality scale:

$$\ln \gamma_{\pm m}^* = \ln \gamma_\pm^* - \ln(1 + \nu m M_S/1000) \quad (87)$$

where $\gamma_{\pm m}^*$ is the mean ionic activity coefficient on the molality scale, m is the molality of the salt (mol/kg-solvent), and Ms is the molecular weight of the solvent (g/mol).

Table 7 shows the fit to molality scale mean ionic activity coefficient data and the identified electrolyte and molecular parameters for the aqueous inorganic and organic electrolytes at 298.15 K as compiled by of Robinson and Stokes (1970) cited above. All mean ionic activity coefficient data are assumed to have standard deviation of 5%. The data for C5 and higher sodium carboxylates were excluded from the fit because these organic electrolytes were known to form micelles at high electrolyte concentrations (Chen, C.-C. et al., "Segment-Based Excess Gibbs Energy Model for Aqueous Organic Electrolytes, *AIChE J.*, 47.2593, 2001). With a few exceptions such as LiBr, most uni-univalent and uni-bivalent electrolytes are well represented as combinations of E and Y− or Y+ parameters. Most uni-univalent electrolytes have E parameter around unity while higher E values are found for higher valent electrolytes. Applicants also found that the fit seems to deteriorate for electrolytes with higher E values. This observation is consistent with the understanding that higher valent electrolytes are known to prone to the formation of hydrated species or other complexation species. The relatively poor representation of these electrolytes with the model reflects the inadequate assumption of complete dissociation for such electrolytes (Chen, C.-C.; et al., "Unification of Hydration and Dissociation Chemistries with the Electrolyte NRTL Model," *AIChE Journal*, 45.1576, 1999). As a derived property, mean ionic activity coefficient becomes meaningless if the complete dissociation assumption of electrolytes does not hold true.

Figure 27:
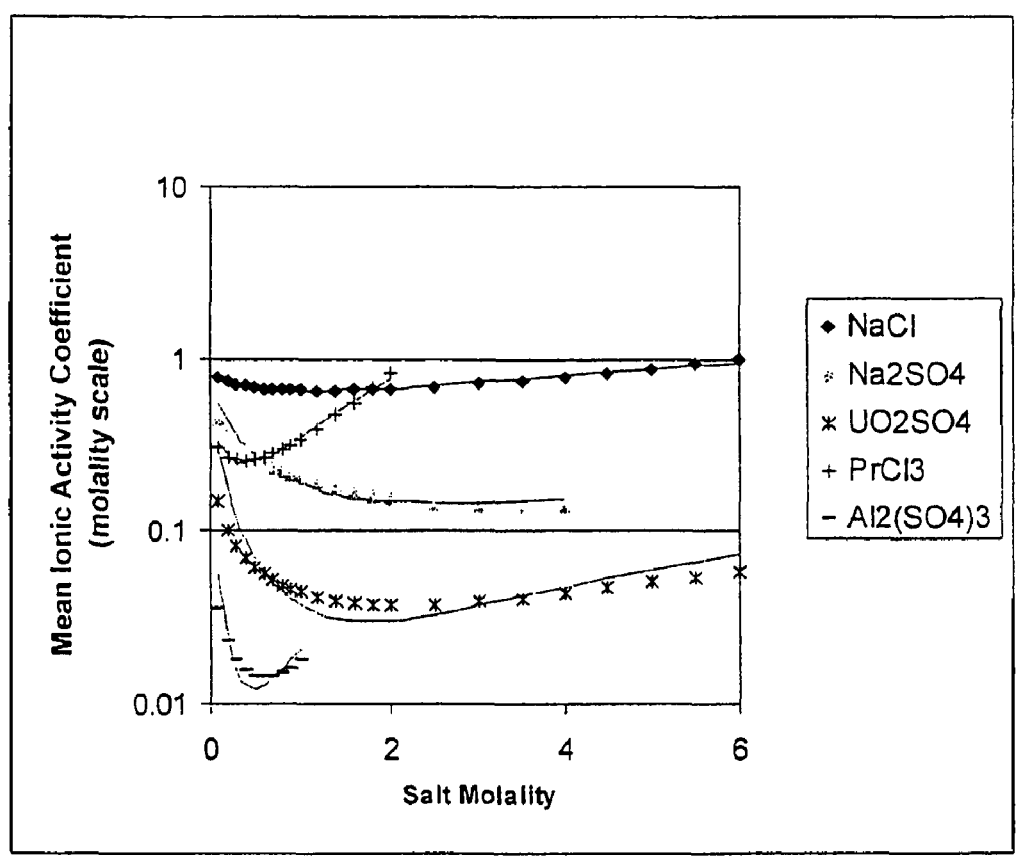
FIG. 27 is a graph illustrating comparison of experimental and calculated molality scale mean ionic activity coefficients of representative aqueous electrolytes at 298.15 K.

To illustrate the quality of the fit, FIG. 27 shows the comparison of experimental and calculated molality scale mean ionic activity coefficients for five aqueous electrolytes at 298.15 K. The solid lines are the calculated values from the model. It shows that the eNRTL-SAC model provides reasonable qualitative representation of the data while the original eNRTL model (Chen, C.-C. et al., "Local Composition Model for Excess Gibbs Energy of Electrolyte Systems," *AIChE J.*, 28:588, 1982) achieves excellent quantitative representation of the data.

EXAMPLE 13

Salt Solubility in Mixed Solvent Systems

At the solubility limit of a nonelectrolytes, the solubility product constant, $K_{sp}$, can be written in terms of the product of the solute concentration and the solute activity coefficient at the saturation concentration:

$$K_{sp} = x_I \gamma_I \quad (88)$$

At the solubility limit of an electrolyte, ionic species precipitate to form salt.

$$\nu_C C^{Z_C} + \nu_A A^{Z_A} \rightarrow C_{\nu_C} A_{\nu_A(s)} \quad (89)$$

The corresponding solubility product constant can be defined as follows.

$$K_{sp} = x_C^{\nu_C} \gamma_C^{*\nu_C} x_A^{\nu_A} \gamma_A^{*\nu_A} \quad (90)$$

Eqs. 89 and 90 can be expanded to include solvent molecules and other species if the solid polymorph involves hydrates, other solvent-containing salts, double salts, triple salts, and others.

Applicants tested the applicability of eNRTL-SAC with the very limited public literature data and some proprietary data on solubilities of a number of inorganic and organic electrolytes in various solvents. This description presents the results with solubility data from public literature. To bring certain consistency to the data treatment, Applicants convert all solute solubility data to mole fraction (except for sodium chloride and sodium acetate). Applicants also assign standard deviation of 10% to all solute solubility data within range of 1 to 0.1, standard deviation of 20% to all solute solubility data with range of 0.1 to 0.01, standard deviation of 30% to data with range of 0.01 to 0.001, and so on.

Figure 28:
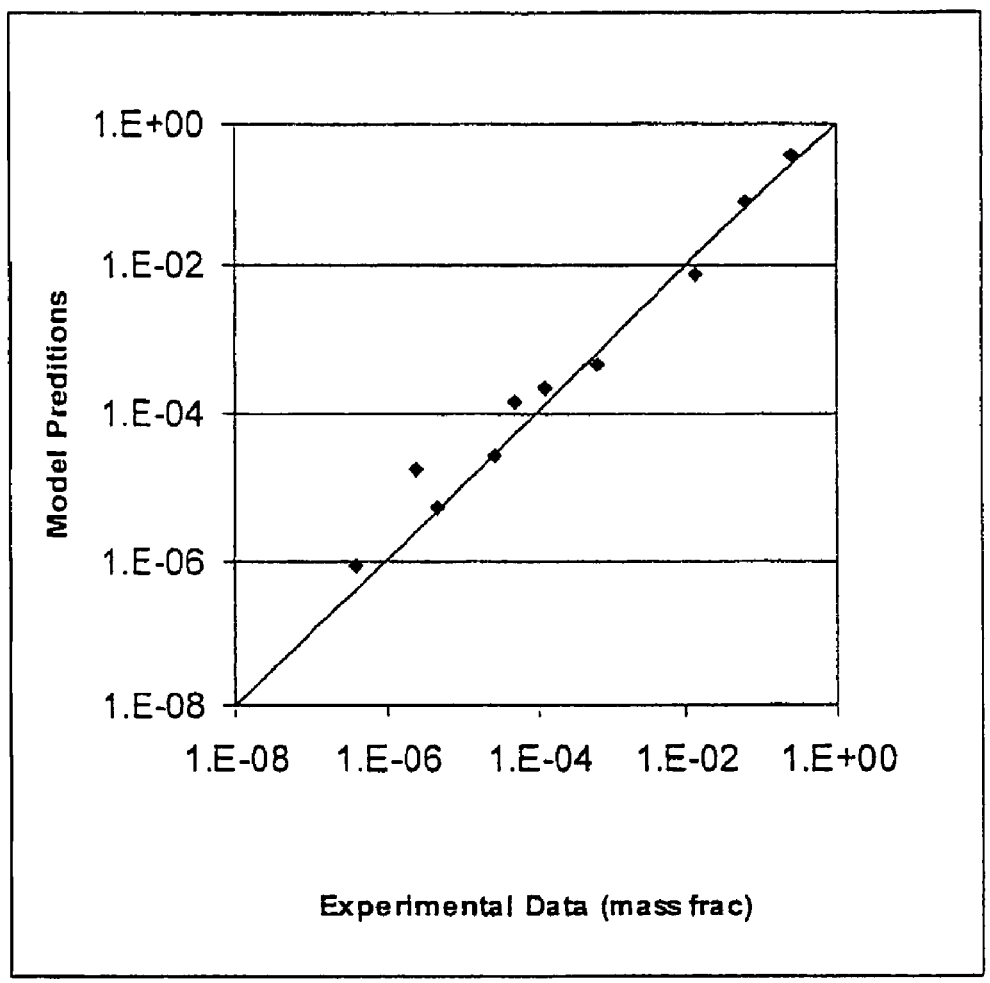
FIG. 28 is a graph illustrating the present invention model results for sodium chloride solubility at 298.15 K.

Solubility data of sodium chloride in twelve different solvents at 298.15 K were successfully fitted with the eNRTL-SAC model. (Note that the temperature for the acetone data is 291.15 K and the temperature for the ethyl acetate data is 292.15 K. However, they are included as if they were data at 298.15 K.) The sodium chloride solubilities in the twelve solvents vary by six orders of magnitude. The satisfactory fit of the data for ten solvents (formic acid and ethyl acetate excluded) is shown in FIG. 28. The eNRTL-SAC model predicts one order-of-magnitude higher solubility for sodium chloride in formic acid and virtually no solubility for sodium chloride in ethyl acetate while the data suggests very low but measurable solubility. The molecular parameters and the solubility product constant were adjusted simultaneously to provide the best fit to the data and the identified values are given in Table 8. In Table 8, the last column to the right quantifies goodness of fit to data. It is worth noting that the electrolyte parameter E for sodium chloride is near unity, similar to the parameters reported in Table 3 for sodium chloride.

Figure 29:
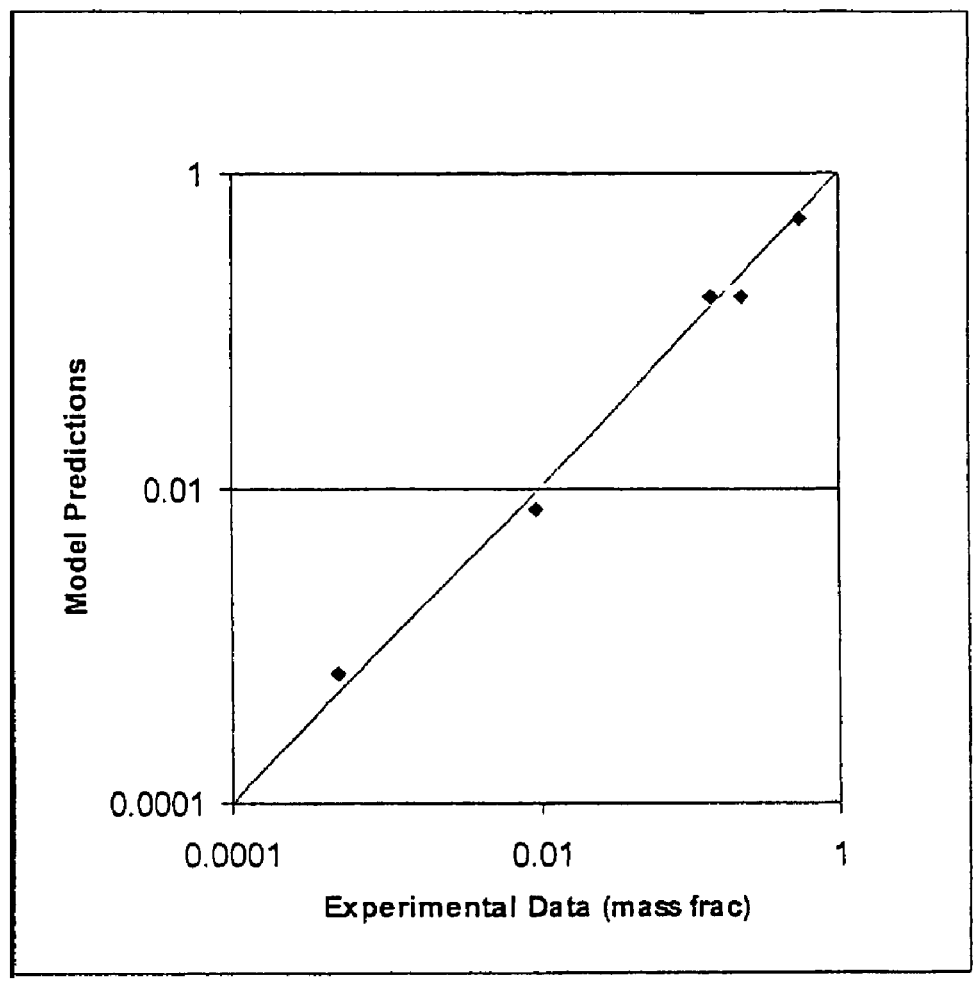
FIG. 29 is a graph illustrating the present invention model results for sodium acetate solubility at 298.15 K.

Solubility data of sodium acetate in five different solvents was also fitted successfully with the eNRTL-SAC model. The solubilities in the five solvents vary by four orders of magnitude. The fit of the data is shown in FIG. 29. The solid phase for the solubility measurements is anhydrous sodium acetate. Note that the data for methanol and acetone was taken at 291.15 K while the data for water and ethylene glycol was taken at 298.15 K. The temperature for the 1-propanol data is not known. In fitting the data, Applicants treated all data as if it was 298.15 K data. The identified molecular parameters and the solubility product constant are given in Table 8. As an organic electrolyte, the electrolyte parameter E for sodium acetate is found to be significantly less than unity.

Figure 30A:
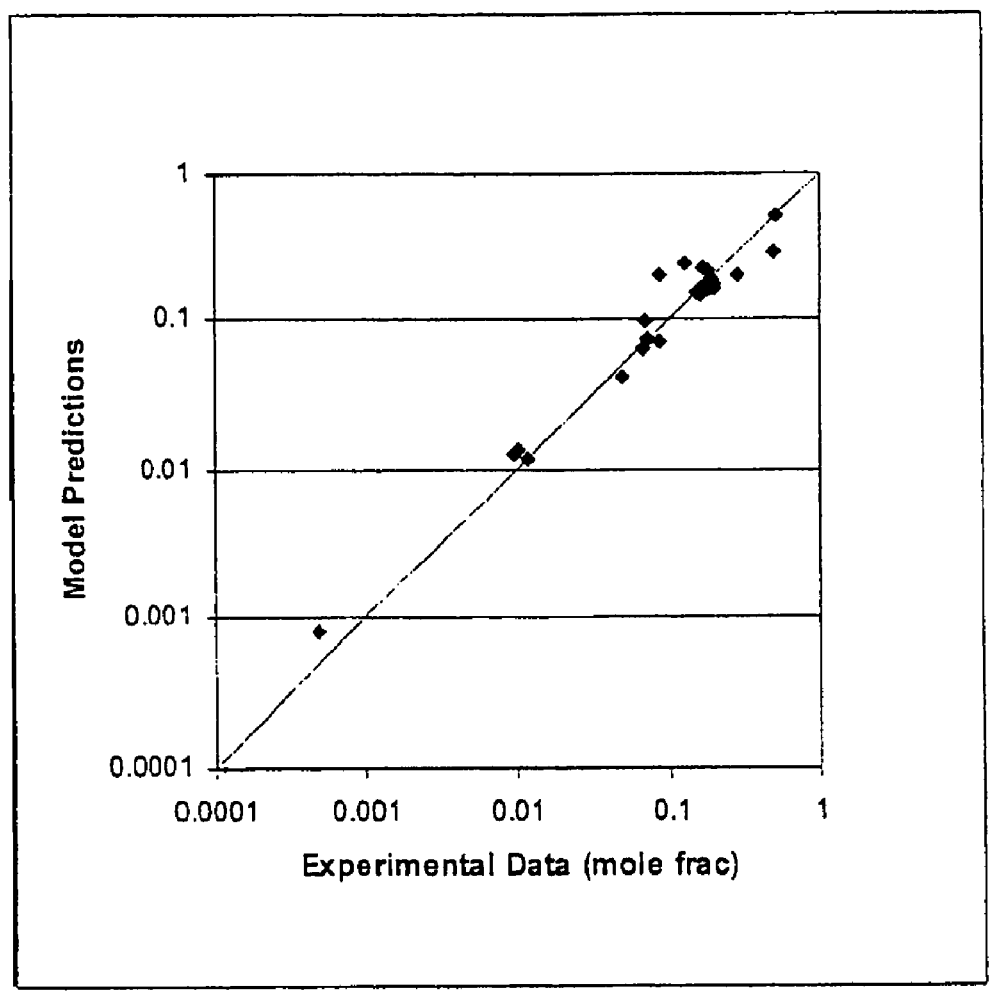
FIG. 30a is a graph illustrating the present invention model results for benzoic acid solubility at 298.15 K.
Figure 30B:
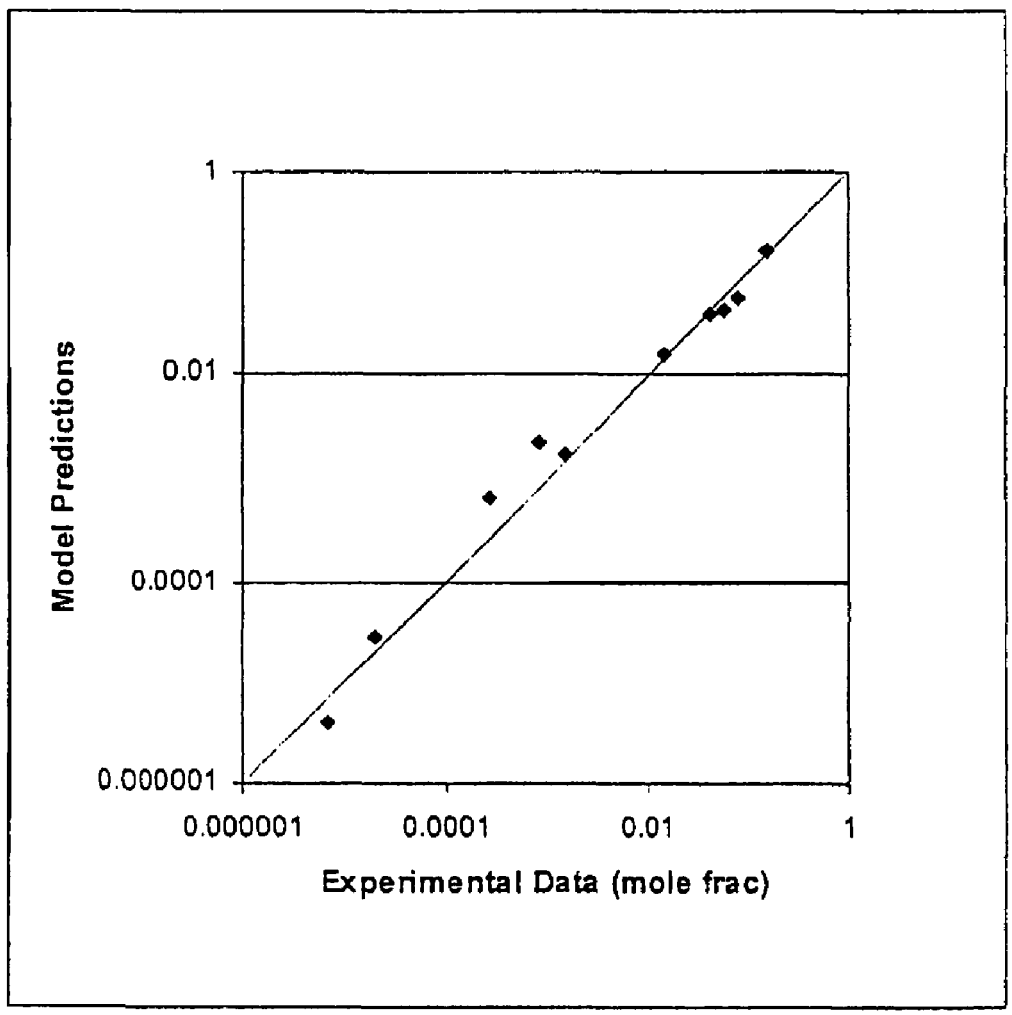
FIG. 30b is a graph illustrating the present invention model results for sodium benzoate solubility at 298.15 K.

FIGS. 30a and 30b show satisfactory representations of the solubility data of benzoic acid in twenty-six solvents (Beerbower, A. et al., "Expanded Solubility Parameter Approach. I. Naphthalene and Benzoic Acid in Individual Solvents," *J. Pharm. Sci.*, 73:179, 1984) and the solubility data of sodium benzoate in ten solvents (Bustamante, P. et al., "The Modified Extended Hansen Method to Determine Partial Solubility Parameters of Drugs Containing a Single Hydrogen Bonding Group and Their Sodium Derivatives: Benzoic Acid/Na and Ibuprofen/Na," *Int. J. of Pharmaceutics*, 194:117, 2000). These solvents are chosen in this study because of the availability of the NRTL-SAC parameters for the solvents from Applicants' prior work. The identified molecular parameters for the two solutes were given in Table 8. It is interesting that the molecular parameters identified for benzoic acid with twenty-six solvents in this study are quite similar to the molecular parameters identified for benzoic acid with seven solvents in Applicants' earlier study. Applicants also noted that the solubility range expands as benzoic acid is converted to sodium benzoate. Furthermore, the molecular parameters have changed from a hydrophobic/polar/hydrophilic combination (benzoic acid) to a polar/hydrophilic/electrolytic combination (sodium benzoate). Solubility data of sodium benzoate in seven other solvents (chloroform, benzene, dioxane, cyclohexane, ethyl acetate, heptane and chlorobenzene) is excluded from FIG. 29b because the eNRTL-SAC model predicts virtually no solubility for sodium benzoate in these solvents while the data suggests very low but measurable solubility. It is probable that the molecular form of sodium benzoate may be present in such highly hydrophobic solvents. However, due to their low concentrations, Applicants chose to ignore these low solubility solvents in this study although the current thermodynamic framework can be used to account for the two solubility routes, i.e., Eqs. 88 and 90, individually or simultaneously.

Figure 31A:
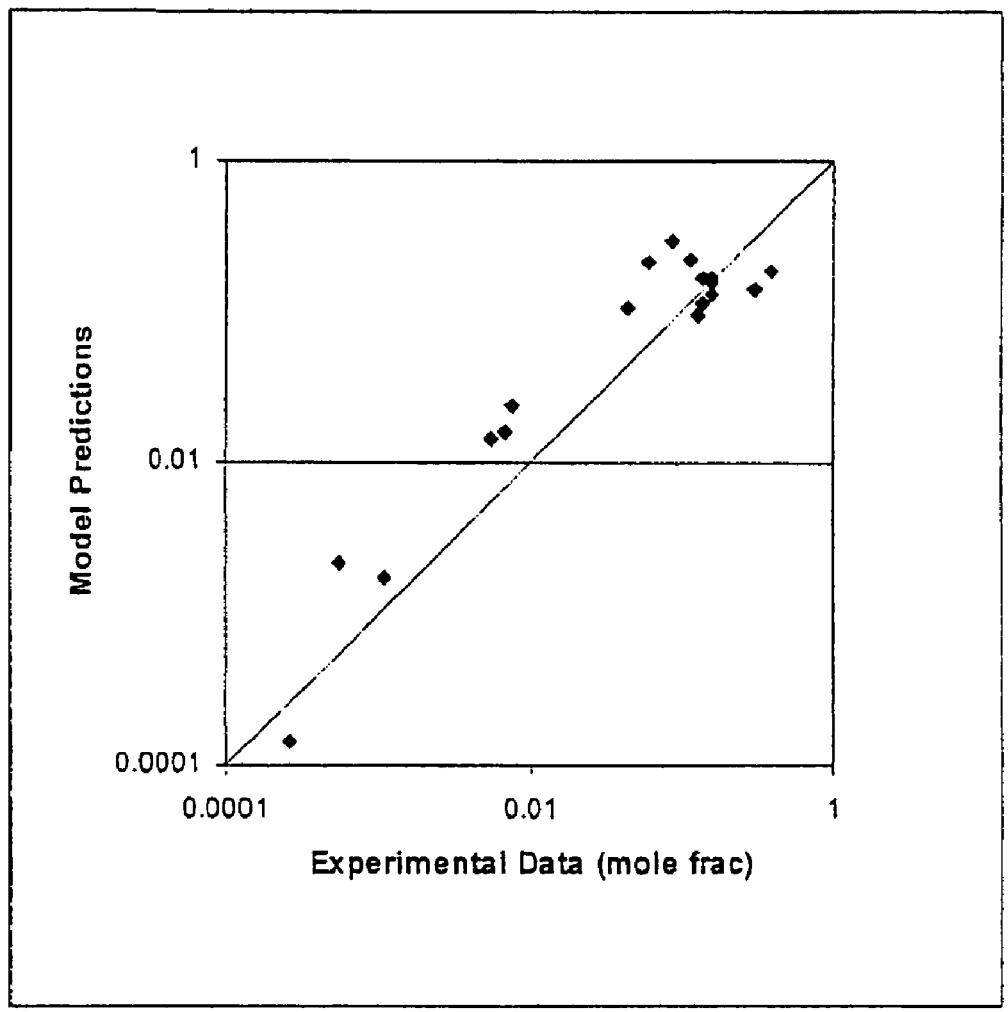
FIG. 31a is a graph illustrating the present invention model results for salicylic acid solubility at 298.15 K.
Figure 31B:
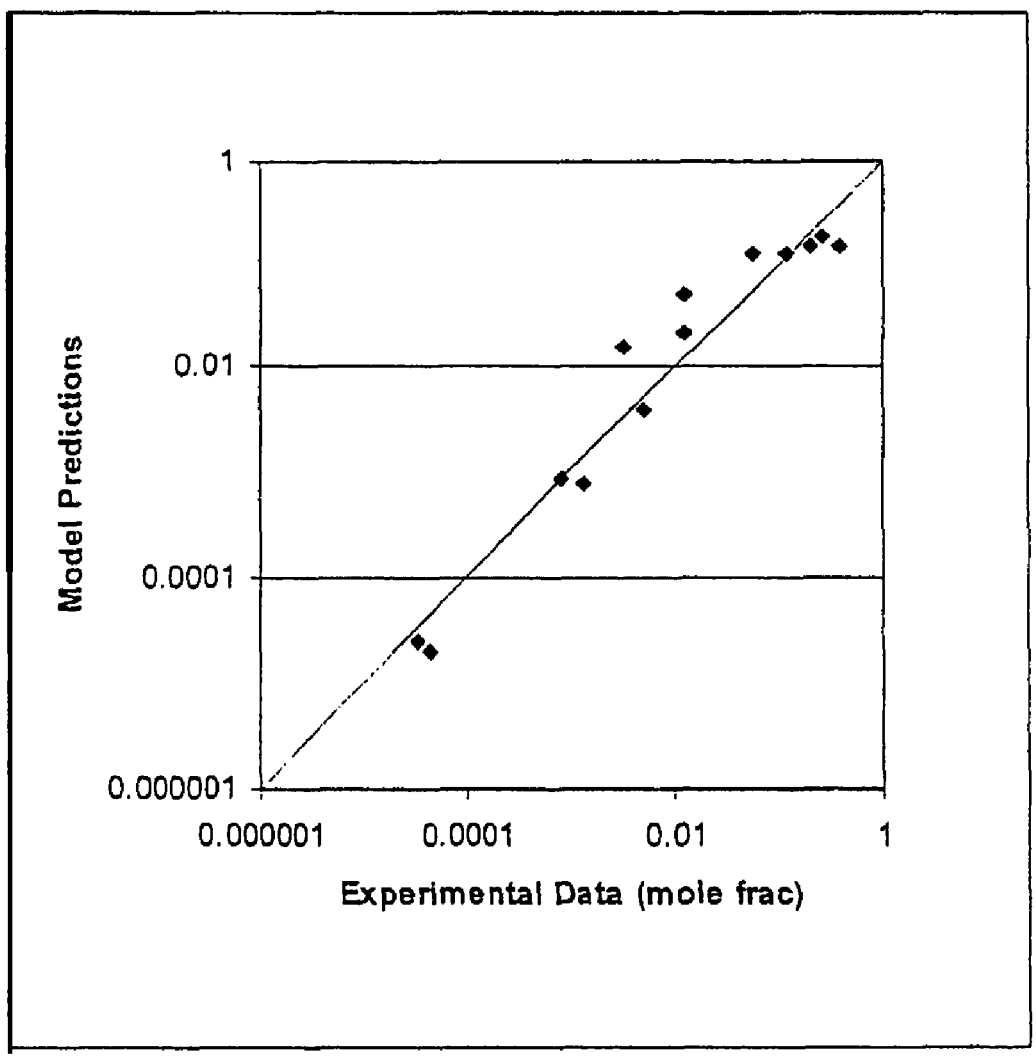
FIG. 31b is a graph illustrating the present invention model results for sodium salicylate solubility at 298.15 K.

FIGS. 31a and 31b show successful representations of the solubility data of salicylic acid in eighteen solvents and the solubility data of sodium salicylate in thirteen solvents (Barra, J. et al., "Proposition of Group Molar Constants for Sodium to Calculate the Partial Solubility Parameters of Sodium Salts Using the van Krevelen Group Contribution Method," *Eur. J. of Pharm. Sci.*, 10:153, 2000). Their molecular parameters were given in Table 8. Like the molecular parameters for benzoic acid and the sodium salt, the molecular parameters have changed from a hydrophobic/polar/hydrophilic combination (salicylic acid) to a polar/hydrophilic/electrolytic combination (sodium salicylate). Solubility data of sodium salicylate in benzene, cyclohexane, and heptane is excluded from FIG. 31b, again because the eNRTL-SAC model predicts virtually no solubility of sodium salicylate in these three solvents although the data suggests very low but measurable solubility. Acetic acid is the only outlier among solvents with significant solubility for sodium salicylate. The eNRTL-SAC model prediction for the solubility of sodium salicylate in acetic acid is about one order of magnitude too high. Acetic acid is not included in the thirteen solvents shown in FIG. 31b.

Figure 32A:
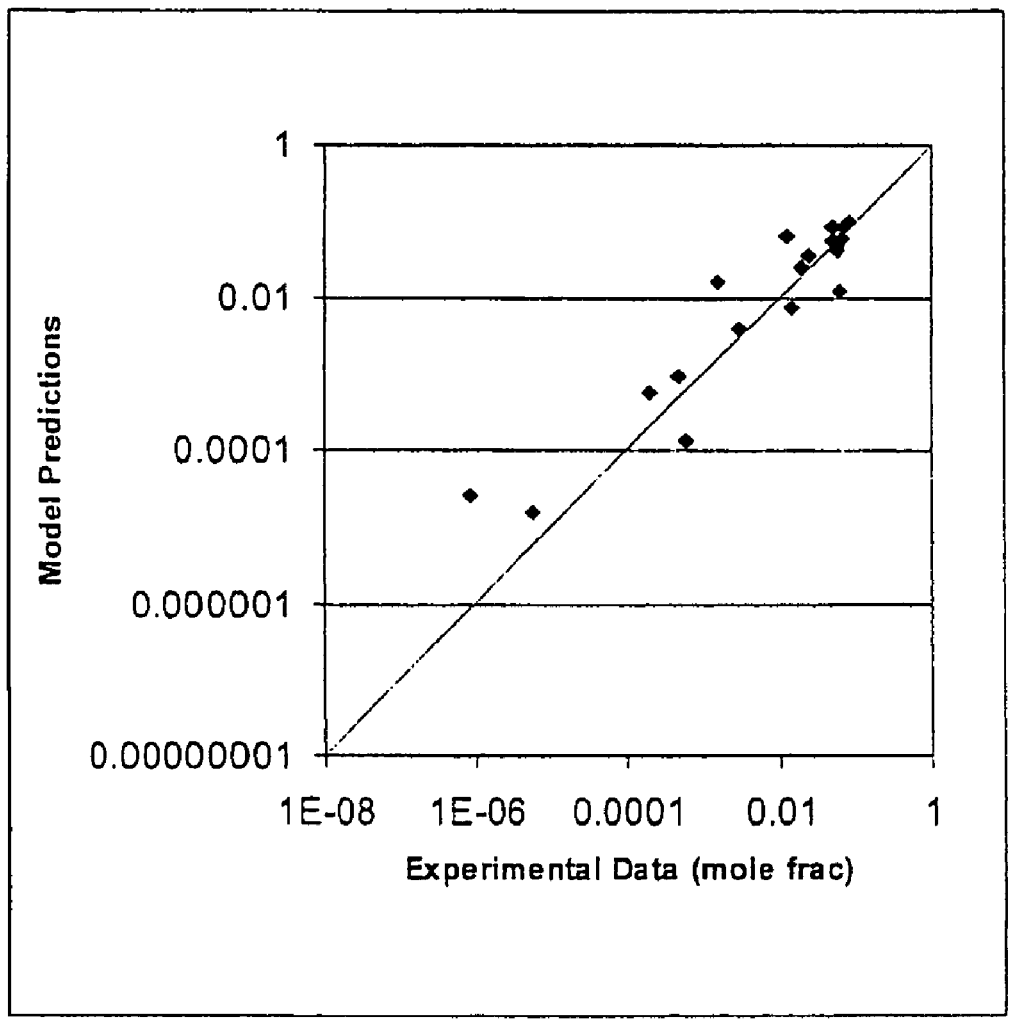
FIG. 32a is a graph illustrating the present invention model results for p-aminobenzoic acid solubility at 298.15 K.
Figure 32B:
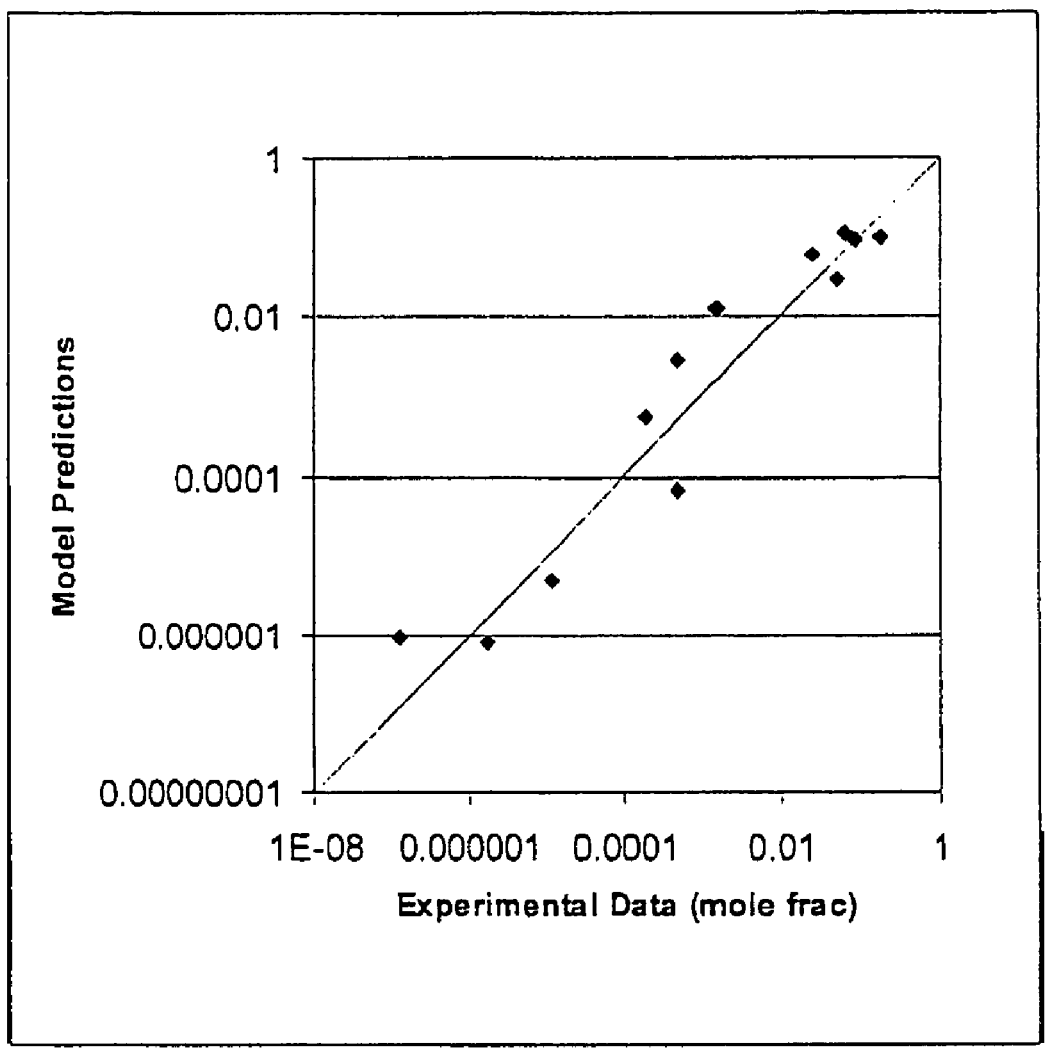
FIG. 32b is a graph illustrating the present invention model results for sodium p-aminobenzoate solubility at 298.15 K.

The eNRTL-SAC model results for the solubility data of p-aminobenzoic acid in nineteen solvents and sodium p-aminobenzoate in twelve solvents (Barra et al., 2000, above) are given in FIGS. 32a and 32b. Again, low solubility solvents (benzene, cyclohexane and heptane) are excluded from FIG. 32b for sodium aminobenzoate. Acetone and DMF are two outliers for sodium aminobenzoate and they are also excluded from FIG. 32b. The eNRTL-SAC model predicts two orders of magnitude higher solubilities in these two solvents.

Figure 33A:
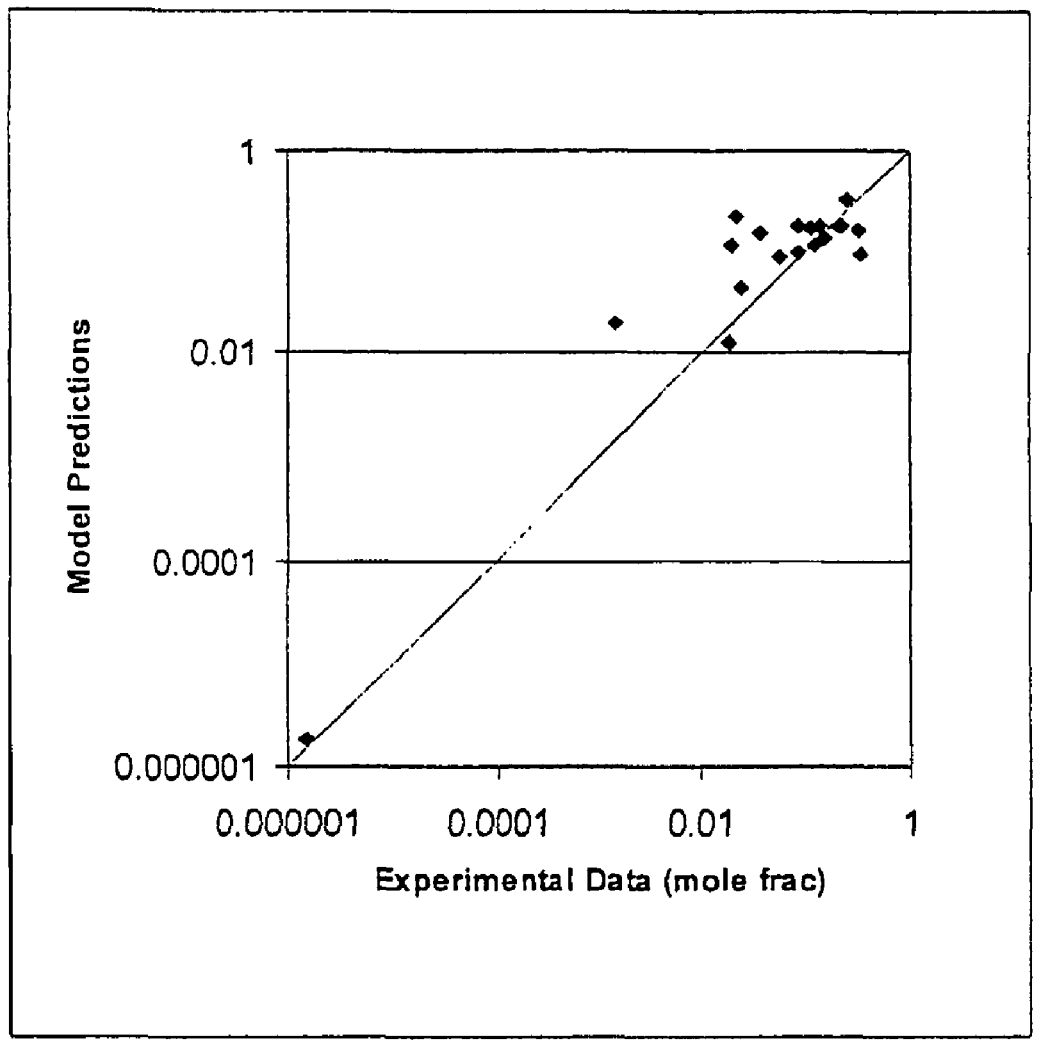
FIG. 33a is a graph illustrating the present invention model results for ibuprofen solubility at 298.15 K
Figure 33B:
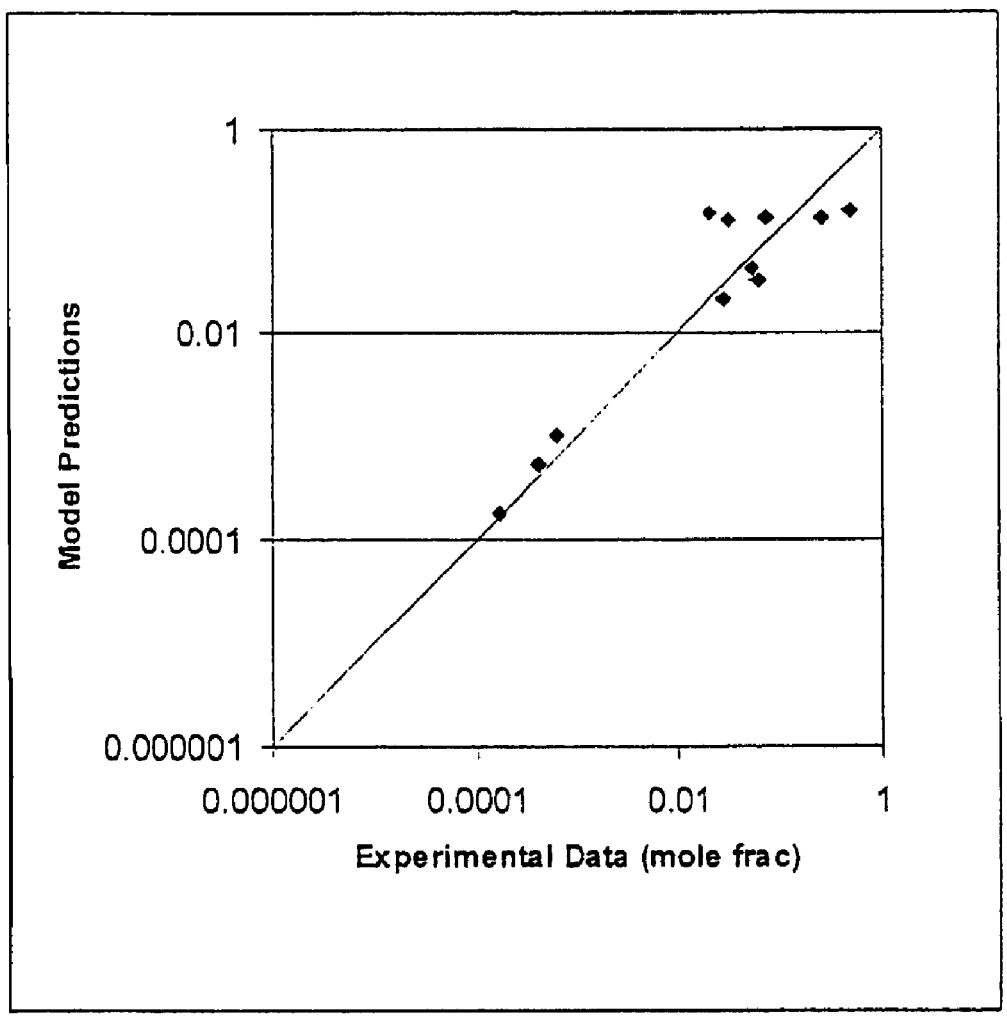
FIG. 33b is a graph illustrating the present invention model results for sodium ibuprofen solubility at 298.15 K.

The solubility data and model calculations for ibuprofen in nineteen solvents and sodium ibuprofen in eleven solvents (Bustamante et al., 2000 above) are given in FIGS. 33a and 33b. In comparison to other organic solutes, one embodiment of the eNRTL-SAC model provides a rather poor fit to the ibuprofen data albeit a better fit than in prior nonelectrolyte models. Applicants did notice that the ibuprofen solubility data from Bustamante et al. are significantly different from those reported by Gracin and Rasmuson (Gracin, S, and A. C. Rasmuson, "Solubility of Phenylacetic Acid, p-Hydroxyphenylacetic Acid, p-Aminophenylacetic acid, p-Hydroxybenzoic acid, and Ibuprofen in Pure Solvents," *J. Chem. Eng Data*, 47.1379, 2002) for certain common solvents including methanol, ethanol, acetone and ethyl acetate. No attempt was made to reconcile the differences between the Bustamante data and the Gracin and Rasmuson data. The eNRTL-SAC model fit to the sodium ibuprofen solubility data appears to be more satisfactory. Again, the eleven solvents reported in FIG. 33b do not include low solubility solvents (benzene, cyclohexane, heptane, and chlorobenzene). Similarly, acetone and DMF are two outliers for sodium ibuprofen and they are also excluded from FIG. 33b. The eNRTL-SAC model predicts two orders of magnitude higher solubilities in these two solvents than the available data. Bustamante et al. (2000, above) reported high water content of the ibuprofen sample (3.3 wt % water) and the sodium ibuprofen sample (13 wt % water). It is not clear how such high water contents in the samples could impact on the solubility measurements.

Figure 34A:
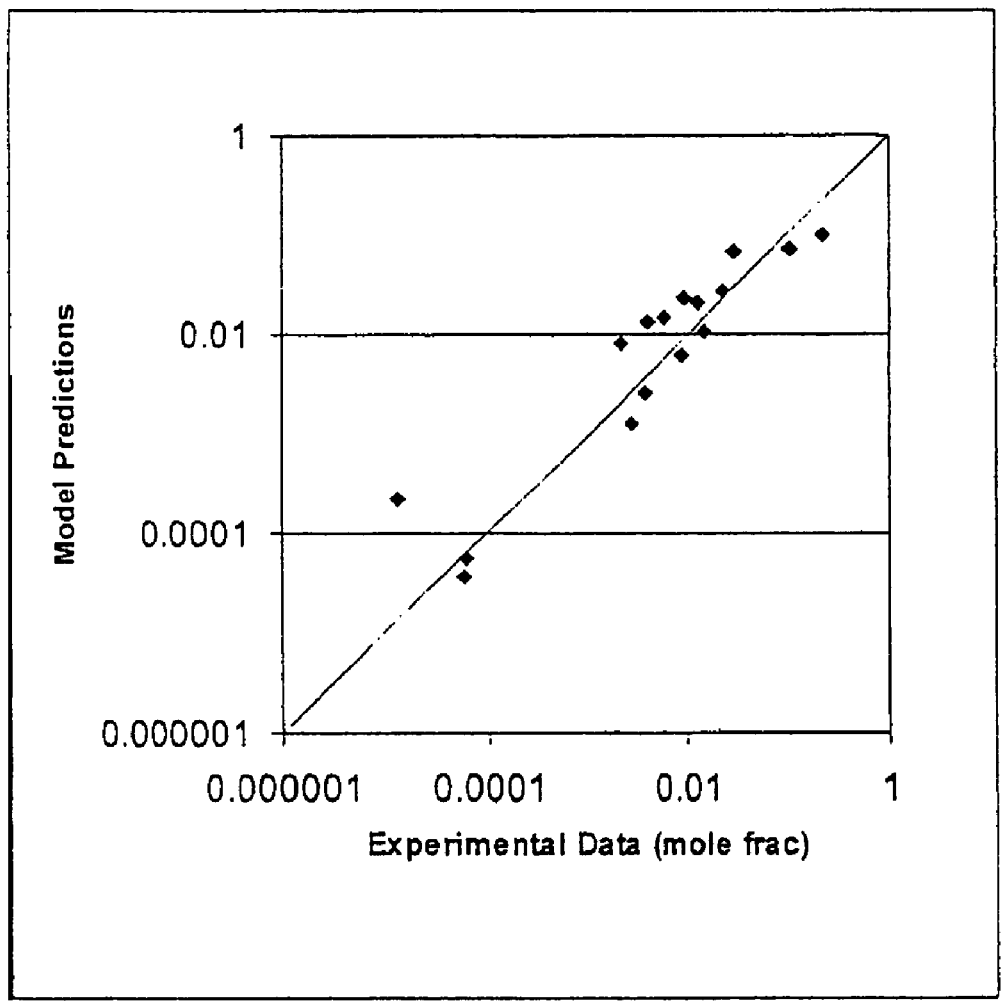
FIG. 34a is a graph illustrating the present invention model results for diclofenac solubility at 298.15 K.
Figure 34B:
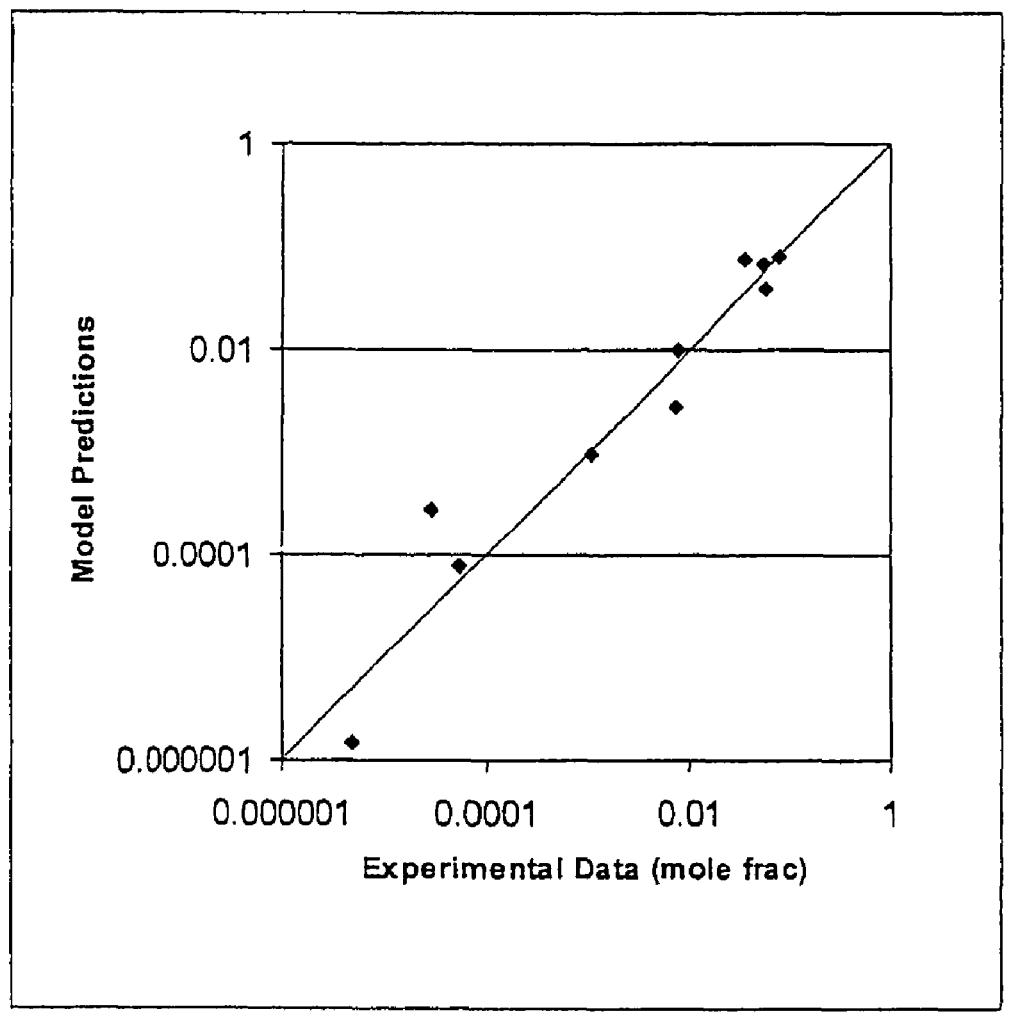
FIG. 34b is a graph illustrating the present invention model results for sodium diclofenac solubility at 298.15 K.

The solubility data for diclofenac in sixteen solvents and sodium diclofenac in ten solvents (Barra et al., 2000 above) are fitted and reported in FIGS. 34a and 34b. The eNRTL-SAC model significantly overestimates the solubilities of diclofenac in acetic acid, formamide and ethylene glycol. These three solvents are excluded from the sixteen solvents shown in FIG. 34a. Data for low solubility solvents (benzene, cyclohexane, ethyl acetate, heptane and chlorobenzene) for sodium diclofenac are excluded from FIG. 34b. Acetic acid and acetone are two outliers with the model estimations one to three orders of magnitude higher solubilities for sodium diclofenac. The two solvents are not included in FIG. 34b.

The solubility data treatment above assumes complete dissociation of electrolytes and considers the solubility problem as formation of salts from ionized species of electrolytes, i.e., Eq. 90. One may argue that electrolytes do not dissociate completely into ionic species especially in organic solvents of low dielectric constant. In the absence of dissociation to ionic species, the solubility relationship can be described by Eq. 88 and the eNRTL-SAC model of the present invention reduces to the NRTL-SAC model of the parent patent application. Applicants have treated the electrolyte systems above as non-electrolytes (i.e., no dissociation to ionic species) with NRTL-SAC and the model results are also included in Table 8. With the absence of electrolyte parameter, the representation of the solubility data deteriorates substantially. Applicants also noted that the identified molecular parameters (X, Y−, Y+, and Z) with the complete dissociation treatment are roughly twice as large as those reported with the non-dissociation treatment. This finding is consistent with the fact that Applicants only assign the molecular parameters (X, Y−, Y+, and Z) to the anion.

TABLE 5

Dielectric Constant of Solvents at 298.15 K.

| solvent name | dielectric constant at 298.15 K. |
|---|---|
| Acetic acid | 6.13 |
| Acetone | 20.83 |
| Acetonitrile | 36.97 |
| Anisole | 4.3 |
| Benzene | 2.27 |
| 1-Butanol | 17.7 |
| 2-Butanol | 15.8 |
| n-Butyl-acetate | 5.1 |
| Methyl-tert-butyl-ether | 2.6 |
| Carbon-tetrachloride | 2.23 |
| Chlorobenzene | 5.56 |
| Chloroform | 4.7 |
| Cumene | 2.22 |
| Cyclohexane | 2.02 |
| 1,2-Dichloroethane | 10.19 |
| 1,1-Dichloroethylene | 4.6 |
| 1,2-Dichloroethylene | 4.6 |
| Dichloromethane | 8.9 |
| 1,2-Dimethoxyethane | not available |
| N,N-Dimethylacetamide | not available |
| N,N-Dimethylformamide | 38.3 |
| Dimethyl-sulfoxide | 47.2 |
| 1,4-Dioxane | 2.21 |
| Ethanol | 24.11 |
| 2-Ethoxyethanol | not available |
| Ethyl-acetate | 6.02 |
| Ethylene-glycol | 41.2 |
| Diethyl-ether | 4.26 |
| Ethyl-formate | 7.16 |
| Formamide | 109.5 |
| Formic-acid | 58.5 |
| n-Heptane | 1.92 |

TABLE 5-continued

Dielectric Constant of Solvents at 298.15 K.

| solvent name | dielectric constant at 298.15 K. |
|---|---|
| n-Hexane | 1.89 |
| Isobutyl-acetate | 5.6 |
| Isopropyl-acetate | not available |
| Methanol | 32.62 |
| 2-Methoxyethanol | not available |
| Methyl-acetate | 6.68 |
| 3-Methyl-1-butanol | 14.7 |
| 2-Hexanone | 14.6 |
| Methylcyclohexane | 2.02 |
| Methyl-ethyl-ketone | 18.5 |
| Methyl-isobutyl-ketone | 13.1 |
| Isobutanol | 17.9 |
| N-Methyl-2-pyrrolidone | 33 |
| Nitromethane | 6.26 |
| n-Pentane | 1.84 |
| 1-Pentanol | 13.9 |
| 1-Propanol | 20.1 |
| Isopropyl-alcohol | 19.9 |
| n-propyl-acetate | 6 |
| Pyridine | 2.3 |
| Sulfolane | 43.3 |
| Tetrahydrofuran | 7.52 |
| 1,2,3,4-Tetrahydronaphthalene | not available |
| Toluene | 2.36 |
| 1,1,1-Trichloroethane | 7.5 |
| Trichloroethylene | 3.42 |
| m-Xylene | 2.24 |
| Water | 78.54 |
| Triethylamine | 2.44 |
| 1-Octanol | 10.3 |

TABLE 6

NRTL Binary Interaction Parameters

| | Segment (1) | | | | |
|---|---|---|---|---|---|
| | X | X | y− | y+ | X |
| | Segment (2) | | | | |
| | y− | z | z | z | y+ |
| $\tau_{12}$ | 1.643 | 6.547 | −2.000 | 2.000 | 1.643 |
| $\tau_{21}$ | 1.834 | 10.949 | 1.787 | 1.787 | 1.834 |
| $\alpha_{12}=\alpha_{21}$ | 0.2 | 0.2 | 0.3 | 0.3 | 0.2 |

| | Segment (1) | | | |
|---|---|---|---|---|
| | x | y− | y+ | z |
| | Segment (2) | | | |
| | e | e | e | e |
| $\tau_{12}$ | 15 | 12 | 12 | 8.885 |
| $\tau_{21}$ | 5 | −3 | −3 | −4.549 |
| $\alpha_{12}=\alpha_{21}$ | 0.2 | 0.2 | 0.2 | 0.2 |

TABLE 7

Results of Fit for Molality Scale Mean Ionic Activity Coefficient Data of Aqueous Electrolytes at 298.15 K. (Data from Robinson and Stokes, 1970)

| | E | Y− | Y+ | $\sigma^1$ | max. molality |
|---|---|---|---|---|---|
| 1-1 Electrolytes | | | | | |
| AgNO$_3$ | 0.738 | | 1.758 | 0.050 | 6.0 |
| CsAc | 1.002 | 0.438 | | 0.011 | 3.5 |
| CsBr | 0.950 | | 0.678 | 0.013 | 5.0 |
| CsCl | 0.948 | | 0.643 | 0.014 | 6.0 |

TABLE 7-continued

Results of Fit for Molality Scale Mean Ionic Activity Coefficient Data of Aqueous Electrolytes at 298.15 K. (Data from Robinson and Stokes, 1970)

| | E | Y- | Y+ | $\sigma^1$ | max. molality |
|---|---|---|---|---|---|
| CsI | 0.956 | | 0.719 | 0.012 | 3.0 |
| CsNO$_3$ | 0.981 | | 1.328 | 0.005 | 1.4 |
| CsOH | 0.942 | 0.354 | | 0.002 | 1.0 |
| HBr | 1.135 | 0.654 | | 0.034 | 3.0 |
| HCl | 1.324 | 0.524 | | 0.087 | 6.0 |
| HClO$_4$ | 1.476 | 0.569 | | 0.136 | 6.0 |
| HI | 1.117 | 0.824 | | 0.035 | 3.0 |
| HNO$_3$ | 0.971 | 0.211 | | 0.005 | 3.0 |
| KAc | 0.998 | 0.386 | | 0.009 | 3.5 |
| KBr | 0.910 | | 0.311 | 0.011 | 5.5 |
| KBrO$_3$ | 0.968 | | 1.141 | 0.002 | 0.5 |
| KCl | 0.920 | | 0.370 | 0.010 | 4.5 |
| KClO$_3$ | 0.958 | | 1.053 | 0.003 | 0.7 |
| KCNS | 0.876 | | 0.477 | 0.019 | 5.0 |
| KF | 0.987 | | 0.042 | 0.004 | 4.0 |
| KH Malonate | 0.846 | | 0.920 | 0.022 | 5.0 |
| KH Succinate | 0.912 | | 0.665 | 0.011 | 4.5 |
| KH$_2$PO$_4$ | 0.970 | | 1.362 | 0.006 | 1.8 |
| KI | 0.903 | | 0.168 | 0.011 | 4.5 |
| KNO$_3$ | 0.856 | | 1.461 | 0.027 | 3.5 |
| KOH | 1.236 | 0.344 | | 0.058 | 6.0 |
| K Tol | 0.750 | | 1.296 | 0.026 | 3.5 |
| LiAc | 0.962 | 0.097 | | 0.002 | 4.0 |
| LiBr | 1.422 | 0.526 | | 0.116 | 6.0 |
| LiCl | 1.282 | 0.436 | | 0.084 | 6.0 |
| LiClO$_4$ | 1.145 | 0.681 | | 0.047 | 4.0 |
| LiI | 1.058 | 0.712 | | 0.033 | 3.0 |
| LiNO$_3$ | 1.050 | 0.294 | | 0.022 | 6.0 |
| LiOH | 1.028 | | 0.652 | 0.022 | 4.0 |
| LiTol | 0.881 | | 0.392 | 0.014 | 4.5 |
| NaAc | 0.978 | 0.301 | | 0.005 | 3.5 |
| NaBr | 0.992 | 0.115 | | 0.008 | 4.0 |
| NaBrO$_3$ | 0.923 | | 0.802 | 0.010 | 2.5 |
| Na Butyrate | 0.989 | 0.566 | | 0.009 | 3.5 |
| NaCl | 1.000 | | | 0.017 | 6.0 |
| NaClO$_3$ | 0.891 | | 0.507 | 0.011 | 3.5 |
| NaClO$_4$ | 0.894 | | 0.267 | 0.010 | 6.0 |
| NaCNS | 0.925 | 0.128 | | 0.006 | 4.0 |
| NaF | 0.976 | | 0.425 | 0.002 | 1.0 |
| Na Formate | 0.905 | | 0.094 | 0.013 | 3.5 |
| NaH Malonate | 0.878 | | 0.664 | 0.019 | 5.0 |
| NaH Succinate | 0.924 | | 0.495 | 0.010 | 5.0 |
| NaH$_2$PO$_4$ | 0.864 | | 1.256 | 0.020 | 6.0 |
| NaI | 1.009 | 0.266 | | 0.012 | 3.5 |
| NaNO$_3$ | 0.825 | | 0.842 | 0.029 | 6.0 |
| NaOH | 1.080 | 0.109 | | 0.039 | 6.0 |
| Na Propionate | 0.992 | 0.448 | | 0.006 | 3.0 |
| Na Tol | 0.793 | | 0.920 | 0.026 | 4.0 |
| NH$_4$Cl | 0.884 | | 0.424 | 0.019 | 6.0 |
| NH$_4$NO$_3$ | 0.813 | | 1.128 | 0.043 | 6.0 |
| RbAc | 1.012 | 0.416 | | 0.011 | 3.5 |
| RbBr | 0.914 | | 0.519 | 0.016 | 5.0 |
| RbCl | 0.929 | | 0.466 | 0.012 | 5.0 |
| RbI | 0.925 | | 0.520 | 0.014 | 5.0 |
| RbNO$_3$ | 0.815 | | 1.611 | 0.038 | 4.5 |
| TlAc | 0.864 | | 0.952 | 0.033 | 6.0 |
| TlClO$_4$ | 1.020 | | 1.231 | 0.000 | 0.5 |
| TlNO3 | 1.069 | | 1.692 | 0.003 | 0.4 |
| 1-2 Electrolytes | | | | | |
| Cs$_2$SO$_4$ | 1.161 | | 2.568 | 0.050 | 1.8 |
| K$_2$CrO$_4$ | 1.048 | | 2.738 | 0.075 | 3.5 |
| K$_2$SO$_4$ | 1.386 | | 2.475 | 0.021 | 0.7 |
| Li$_2$SO$_4$ | 1.138 | | 2.177 | 0.051 | 3.0 |
| Na$_2$CrO$_4$ | 1.091 | | 2.443 | 0.051 | 4.0 |
| Na$_2$ Fumarate | 1.259 | | 1.770 | 0.041 | 2.0 |
| Na$_2$ Maleate | 1.202 | | 2.699 | 0.075 | 3.0 |
| Na$_2$SO$_4$ | 0.988 | | 3.273 | 0.090 | 4.0 |
| Na$_2$S$_2$O$_3$ | 1.071 | | 2.709 | 0.064 | 3.5 |
| (NH$_4$)$_2$SO$_4$ | 1.006 | | 3.477 | 0.118 | 4.0 |
| Rb$_2$SO$_4$ | 1.150 | | 2.743 | 0.052 | 1.8 |
| 1-3 Electrolytes | | | | | |
| K$_3$Fe(CN)$_6$ | 1.328 | | 4.996 | 0.101 | 1.4 |
| 1-4 Electrolytes | | | | | |
| K$_4$Fe(CN)$_6$ | 1.449 | | 9.448 | 0.146 | 0.9 |
| 2-1 Electrolytes | | | | | |
| BaAc$_2$ | 1.016 | | 0.997 | 0.128 | 3.5 |
| BaBr$_2$ | 1.267 | | 0.358 | 0.018 | 2.0 |
| BaCl$_2$ | 1.227 | | 0.585 | 0.029 | 1.8 |
| Ba(ClO$_4$)$_2$ | 1.305 | | 0.261 | 0.049 | 5.0 |
| BaI$_2$ | 1.354 | 0.028 | | 0.017 | 2.0 |
| Ba(NO$_3$)$_2$ | 1.435 | | 1.268 | 0.008 | 0.4 |
| CaBr$_2$ | 1.969 | | 0.171 | 0.495 | 6.0 |
| CaCl$_2$ | 1.701 | | 0.309 | 0.283 | 6.0 |
| Ca(ClO$_4$)$_2$ | 2.021 | | | 0.431 | 6.0 |
| CaI$_2$ | 1.419 | 0.131 | | 0.036 | 2.0 |
| Ca(NO$_3$)$_2$ | 1.108 | | 0.875 | 0.053 | 6.0 |
| CdBr$_2$ | 1.324 | | 3.164 | 0.294 | 4.0 |
| CdCl$_2$ | 1.052 | | 3.047 | 0.315 | 6.0 |
| CdI$_2$ | 1.780 | | 3.820 | 0.337 | 2.5 |
| Cd(NO$_3$)$_2$ | 1.176 | | 0.500 | 0.037 | 2.5 |
| CoBr$_2$ | 1.779 | | | 0.218 | 5.0 |
| CoCl$_2$ | 1.397 | | 0.194 | 0.046 | 4.0 |
| CoI$_2$ | 2.260 | | | 0.488 | 6.0 |
| Co(NO$_3$)$_2$ | 1.444 | | 0.296 | 0.113 | 5.0 |
| CuCl$_2$ | 1.033 | 0.425 | 1.217 | 0.069 | 6.0 |
| Cu(NO$_3$)$_2$ | 1.409 | | 0.416 | 0.117 | 6.0 |
| FeCl$_2$ | 1.319 | | 0.255 | 0.011 | 2.0 |
| MgAc$_2$ | 1.192 | | 0.946 | 0.059 | 4.0 |
| MgBr$_2$ | 1.941 | | | 0.347 | 5.0 |
| MgCl$_2$ | 1.745 | | 0.144 | 0.275 | 5.0 |
| Mg(ClO$_4$)$_2$ | 1.988 | 0.162 | | 0.303 | 4.0 |
| MgI$_2$ | 2.237 | | | 0.470 | 5.0 |
| Mg(NO$_3$)$_2$ | 1.493 | | 0.198 | 0.140 | 5.0 |
| MnCl$_2$ | 1.273 | | 0.343 | 0.020 | 6.0 |
| NiCl$_2$ | 1.533 | | 0.189 | 0.123 | 5.0 |
| Pb(ClO$_4$)$_2$ | 1.549 | | 0.236 | 0.184 | 6.0 |
| Pb(NO$_3$)$_2$ | 1.129 | | 1.964 | 0.083 | 2.0 |
| SrBr$_2$ | 1.330 | | 0.183 | 0.023 | 2.0 |
| SrCl$_2$ | 1.401 | | 0.357 | 0.082 | 4.0 |
| Sr(ClO$_4$)$_2$ | 1.742 | | 0.034 | 0.261 | 6.0 |
| SrI$_2$ | 1.384 | 0.076 | | 0.030 | 2.0 |
| Sr(NO$_3$)$_2$ | 0.978 | | 1.250 | 0.091 | 4.0 |
| UO$_2$Cl$_2$ | 1.277 | | 0.024 | 0.017 | 3.0 |
| UO$_2$(ClO$_4$)$_2$ | 2.854 | | | 0.883 | 5.5 |
| UO$_2$(NO$_3$)$_2$ | 1.392 | 0.372 | 0.490 | 0.036 | 5.5 |
| ZnBr$_2$ | 0.906 | | 0.337 | 0.088 | 6.0 |
| ZnCl$_2$ | 0.953 | | 0.971 | 0.065 | 6.0 |
| Zn(ClO$_4$)$_2$ | 2.045 | 0.130 | | 0.318 | 4.0 |
| ZnI$_2$ | 0.868 | 0.132 | | 0.116 | 6.0 |
| Zn(NO$_3$)$_2$ | 1.518 | | 0.214 | 0.176 | 6.0 |
| 2-2 Electrolytes | | | | | |
| BeSO$_4$ | 1.376 | | 4.077 | 0.233 | 4.0 |
| MgSO$_4$ | 1.380 | | 4.206 | 0.238 | 3.0 |
| MnSO$_4$ | 1.287 | | 4.460 | 0.271 | 4.0 |
| NiSO$_4$ | 1.398 | | 4.381 | 0.220 | 2.5 |
| CuSO$_4$ | 1.587 | | 4.114 | 0.154 | 1.4 |
| ZnSO$_4$ | 1.339 | | 4.417 | 0.242 | 3.5 |
| CdSO$_4$ | 1.295 | | 4.547 | 0.271 | 3.5 |
| UO$_2$SO$_4$ | 1.215 | | 4.528 | 0.309 | 6.0 |
| 3-1 Electrolytes | | | | | |
| AlCl$_3$ | 1.730 | | 0.579 | 0.087 | 1.8 |
| CeCl$_3$ | 1.562 | | 0.883 | 0.047 | 1.8 |
| CrCl$_3$ | 1.589 | | 0.641 | 0.022 | 1.2 |
| Cr(NO$_3$)$_3$ | 1.551 | | 0.761 | 0.036 | 1.4 |
| EuCl$_3$ | 1.586 | | 0.820 | 0.049 | 2.0 |
| LaCl$_3$ | 1.553 | | 0.877 | 0.042 | 2.0 |
| NdCl$_3$ | 1.575 | | 0.882 | 0.045 | 2.0 |
| PrCl$_3$ | 1.562 | | 0.892 | 0.042 | 2.0 |
| ScCl$_3$ | 1.636 | | 0.709 | 0.041 | 1.8 |
| SmCl$_3$ | 1.581 | | 0.843 | 0.046 | 2.0 |
| YCl$_3$ | 1.629 | | 0.807 | 0.057 | 2.0 |

TABLE 7-continued

Results of Fit for Molality Scale Mean Ionic Activity
Coefficient Data of Aqueous Electrolytes at 298.15
K. (Data from Robinson and Stokes, 1970)

|  | E | Y− | Y+ | $\sigma^1$ | max. molality |
|---|---|---|---|---|---|
| 3-2 Electrolytes | | | | | |
| $Al_2(SO_4)_3$ | 1.354 | | 4.886 | 0.222 | 1.0 |
| $Cr_2(SO_4)_3$ | 1.257 | | 4.549 | 0.218 | 1.2 |
| 4-1 Electrolytes | | | | | |
| $Th(NO_3)_4$ | 1.273 | | 1.251 | 0.056 | 5.0 |

1. $\sigma$ is defined to be $$\left[\sum_i^N \left(\frac{\gamma_{\pm i}^{*exp} - \gamma_{\pm i}^{*cal}}{\gamma_{\pm i}^{*exp}}\right)^2 / N\right]^{1/2}$$

where $\gamma_\pm^*$ is the mean ionic activity coefficient of electrolyte and N is the number of data used in correlations

TABLE 8 eNRTL-SAC Model Parameters for Solutes

| solute | no. of solvents | X | Y− | Y+ | Z | E | $\ln K_{sp}$ | $\sigma^4$ |
|---|---|---|---|---|---|---|---|---|
| benzoic acid[1] | 26 | 0.494 | | 0.336 | 0.468 | | −1.714 | 0.292 |
| salicylic acid[1] | 18 | 0.726 | 0.176 | | 0.749 | | −1.624 | 0.774 |
| p-aminobenzoic acid[1] | 19 | 0.552 | 0.423 | 0.594 | 0.881 | | −3.348 | 1.206 |
| Ibuprofen[1] | 19 | 1.038 | 0.051 | 0.028 | 0.318 | | −1.423 | 1.055 |
| Diclofenac[1] | 16 | 0.158 | | 1.678 | 0.451 | | −3.560 | 0.991 |
| sodium chloride[2] | 10 | | | 1.444 | | 0.994 | −6.252 | 0.783 |
| sodium acetate[2] | 5 | | | 1.417 | | 0.521 | −6.355 | 0.241 |
| sodium benzoate[2] | 10 | | 0.750 | 1.685 | 2.201 | 0.539 | −7.312 | 0.493 |
| sodium salicylate[2] | 13 | | | 0.845 | 2.417 | 0.090 | −4.889 | 0.771 |
| sodium p-aminobenzoate[2] | 12 | | | 2.299 | 2.387 | 0.192 | −8.293 | 1.258 |
| sodium ibuprofen[2] | 11 | 1.819 | 1.743 | | 2.362 | 0.150 | −17.844 | 0.886 |
| sodium diclofenac[2] | 10 | 0.409 | | 3.558 | 3.486 | 0.161 | −14.202 | 0.858 |
| sodium chloride[3] | 10 | | | 1.060 | 2.200 | | −3.540 | 0.923 |
| sodium acetate[3] | 5 | | | 0.249 | 0.679 | | −2.277 | 0.281 |
| sodium benzoate[3] | 10 | | | 0.179 | 1.825 | | −2.978 | 0.699 |
| sodium salicylate[3] | 13 | | | 0.373 | 1.572 | | −2.153 | 1.058 |
| sodium p-aminobenzoate[3] | 12 | | 0.125 | 0.649 | 1.895 | | −3.247 | 1.904 |
| sodium ibuprofen[3] | 11 | 0.270 | 0.394 | | 0.823 | | −2.364 | 1.685 |
| sodium diclofenac[3] | 10 | 0.454 | | 0.124 | 2.493 | | −4.405 | 1.473 |

[1] nonelectrolytes
[2] electrolytes
[3] treated as nonelectrolytes

4. $\sigma$ is defined to be $\left(\sum_i^N (\ln x_i^{exp} - \ln x_i^{cal})^2 / N\right)^{1/2}$ where x is the solubility of solute, i.e., mole fraction (note that mass fraction for sodium chloride and sodium acetate), and N is the number of data used in correlations.

EXAMPLE 14

Activity Coefficient Model in Chromatography

Chromatographers then can use activity coefficient models as described herein to determine activity coefficients of one or more chemical species in the mobile phase and the stationary phase and to select solvent types, solvent composition and elution gradients for the mobile phase and the column packing for the stationary phase as they optimize and control selectivity and productivity of a chromatography reaction.

The methods disclosed herein, among other features, compute activity coefficients from the combinatorial term and the residual term as described below $$\ln \gamma_I = \ln \gamma_I^C + \ln \gamma_I^R \quad (102)$$

where $\gamma_I$ is an activity coefficient for the one or more chemical species, the mobile phase component or the stationary phase component, $\gamma_I^C$ is a combinatorial contribution to the activity coefficient for the one or more chemical species, the mobile phase component or the stationary phase component, and $\gamma_I^R$ is a residual contribution to the activity coefficient of the one or more chemical species, the mobile phase component or the stationary component.

$$\ln \gamma_I^R = \ln \gamma_I^{lc} = \sum_m r_{m,I}[\ln \Gamma_m^{lc} - \ln \Gamma_{m,I}^{lc}] \quad (103)$$

$$\ln \Gamma_m^{lc} = \frac{\sum_j x_j G_{jm} \tau_{jm}}{\sum_k x_k G_{km}} + \sum_{m'} \frac{x_{m'} G_{mm'}}{\sum_k x_k G_{km'}} \left(\tau_{mm'} - \frac{\sum_j x_j G_{jm'} \tau_{jm'}}{\sum_k x_k G_{km'}}\right) \quad (104)$$

-continued $$\ln \Gamma_{m,I}^{lc} = \frac{\sum_j x_{j,I} G_{jm} \tau_{jm}}{\sum_k x_{k,I} G_{km}} + \sum_{m'} \frac{x_{m',I} G_{mm'}}{\sum_k x_{k,I} G_{km'}} \left(\tau_{mm'} - \frac{\sum_j x_{j,I} G_{jm'} \tau_{jm'}}{\sum_k x_{k,I} G_{km'}}\right) \quad (105)$$

where I is a component index for the one or more chemical species, the mobile phase component, or the stationary phase component, each j, k, m. and m' is a segment species index, $x_j$ is a segment-based mole fraction of segment species j, $x_{j,i}$ is a segment-based mole fraction of segment species j in the I, $r_{m,I}$ is a number of segment species m contained only in the I, $\Gamma_m^{lc}$ is an activity coefficient of segment species m, $\gamma_m^{lc,I}$ is an activity coefficient of segment species m contained in the I, and G and τ are binary quantities related to each other by a non-random factor parameter α as in G=exp(−ατ). α and τ are the nonrandomness factor parameter and the segment-segment binary interaction energy parameter, respectively.

EXAMPLE 15

Prediction of Activity Coefficient Using the NRTL SAC Method

To apply the NRTL SAC method described herein for the prediction of solute activity coefficients in chromatography operations, it is necessary to identify the equivalent numbers for the solutes, the solvents, and the various stationary phase types. The methodology to identify these equivalent segment numbers are described above. The equivalent numbers of the stationary phase component can be determined from the partition coefficient data or the retention factor data of at least four solutes of varied surface interaction characteristics with the specific column packing. Such partition coefficient data reflect the nature of the solute-stationary phase surface interactions that are the basis for the determination of the equivalent numbers for the column packing type.

Given the equivalent numbers for the solutes, solvents, and stationary phase component, the NRTL SAC method can then be used to determine solute activity coefficients in the mobile phase and the stationary phase and chromatography column selectivity and productivity as functions of solutes, solvent types, solvent composition, column packing types, and temperature. For given solutes, the NRTL SAC method is useful in selecting solvent types, solvent composition, and stationary phase component. Integrated with mathematical model for chromatography operations, the model becomes a core component of comprehensive and $1^{st}$ principles based chromatography unit operation model for design, optimization, and control of this ubiquitous active pharmaceutical ingredient purification equipment in the pharmaceutical industry.

EXAMPLE 16

Modeling Solute Partition Coefficients in Chromatography Operations

There are different types of chromatographic columns, e.g., reverse-phase chromatography, normal phase chromatography, hydrophobic interaction chromatography, hydrophilic interaction chromatography, ion-pair chromatography, ion-exchange chromatography, etc.

The magnitude of retention of a chemical specie (e.g., solute) in chromatography is measured under isocratic condition (e.g., constant mobile phase solvent composition) by the retention factor $k_I$:

$$k_I = \frac{C_s V_s}{C_m V_m} = \frac{t_{rI} - t_0}{t_0} \tag{91}$$

$k_I$ is a capacity ratio of the one or more chemical species, $C_s$ is the concentration in the stationary phase, $V_s$ is the volume of the stationary phase, $C_m$ is the concentration in the mobile phase, $V_m$ is the volume of the mobile phase, $t_{rI}$ is a retention time of the one or more chemical species, and $t_0$ is an elution time for an inert tracer. The retention time is related to the concentration of the one or more chemical species in the stationary phase. Once the retention time for the one or more chemical species on the stationary phase (e.g., packing) of the stationary phase are known, the concentration of the one or more chemical species can be calculated and the NRTL-SAC model parameters (e.g., the equivalent numbers, etc.) described herein can be determined by fitting the concentration data as the NRTL-SAL model parameters can be determined for a solute by fitting solubility values.

For the separation of two chemical species I and j, selectivity is defined by the ratio (α) of the capacity ratios of the solutes:

$$\alpha = \frac{k_J}{k_I} \tag{92}$$

The retention factor $k_I$ is related to the equilibrium constant, $K_I$, or the Gibbs free energy change associated with solute transfer from the mobile phase to the stationary phase as $$k_I = \frac{x_s V_s}{x_m V_m} = K_I \Phi \tag{93}$$

$$\Delta G_I = -RT \ln K_I \tag{94}$$

$K_I$ is a partition coefficient, Φ is a phase ratio, $V_s$ is a volume of the stationary phase component, $V_m$ is a volume of the mobile phase component, $x_s$ is a concentration of the one or more chemical species interacting with the stationary phase-component, and $x_m$ is a concentration of the one or more chemical species interacting with the mobile phase component.

$$\Phi = \frac{V_s}{V_m} \tag{95}$$

$$K_I = \frac{x_s}{x_m} \tag{96}$$

At thermodynamic equilibrium, the stationary phase solute activity should be equal to the mobile phase solute activity.

$$a_s = a_m \tag{97}$$

i.e., $$x_s \gamma_s = x_m \gamma_m \tag{98}$$

The mobile phase solute activity coefficient $\gamma_m$ is a function of mobile phase solute and solvent composition while the stationary phase solute activity coefficient $\gamma_s$ is a function of solute and the stationary phase composition. The partition coefficient $K_I$ can be derived from ratio of the activity coefficients.

$$K_I = \frac{\gamma_m}{\gamma_s} \tag{99}$$

In chromatographic operations, solute concentrations are very low. $\gamma_m^\infty$ and $\gamma_s^\infty$ are activity coefficients of the one or more chemical species at infinite dilution approximated from $\gamma_m$ and $\gamma_s$. $\gamma_m$ is a mobile phase activity coefficient of the one or more chemical species, and $\gamma_s$ is a stationary phase activity coefficient of the one or more chemical species.

$$K_I = \frac{\gamma_m^\infty}{\gamma_s^\infty} \qquad (100)$$

It is reported that at least for some chromatography systems, the solute activity coefficient in the stationary phase remain practically constant while the mobile phase composition is changed. If this observation holds true, then the partition coefficient $K_I$ is controlled by the solute infinite dilution activity coefficient in the mobile phase.

EXAMPLE 17

Separation of Two Bands in Chromatography

The separation of any two bands in the chromatogram can be varied systematically by changing experimental conditions. Resolution, R, can be expressed in terms of three parameters (k, α, and N) which are directly related to the experimental conditions:

$$R_s = \frac{1}{4}(\alpha - 1)N^{1/2}\frac{k}{1+k} \qquad (101)$$

Here k is the average retention factor for the two bands, N is the column plate number, and α is the separation factor defined in Eq. (92). As both k and α are functions of the solute activity coefficients in the mobile phase and the stationary phase, they are determined by those conditions that affect activity coefficients the solutes in the mobile phase and the stationary phase: 1) composition of the mobile phase, 2) composition of the stationary phase, and 3) temperature. Changes in the mobile phase in terms of solvent types and solvent composition, changes in the column packing, and changes in temperature affect the activity coefficients of the solutes in the mobile phase and the stationary phase which then determine the selectivity and productivity of the column. In other words, to optimize and control selectivity and productivity of chromatography requires quantitative knowledge on how the solute activity coefficients are affected by the changes in the mobile phase, the stationary phase and the temperature.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of modeling chromatography comprising modeling a retention time of one or more chemical species in a mixture of at least two chemical species by the computer implemented steps of:
   a) providing a modeler configured to be executable by a processor, the modeler during execution being formed of (i) a databank of molecular descriptors of known chemical species, and (ii) a calculator of molecular descriptors of unknown chemical species;
   b) determining at least one conceptual segment, instead of a molecular structural segment for: (a) each of the one or more chemical species, (b) a mobile phase component, and (c) a stationary phase component, the conceptual segment being determined from in-mixture behavior of the at least two chemical species, including for each conceptual segment, (i) identifying the conceptual segment as one of a hydrophobic segment, a hydrophilic segment, a polar segment, a solvation segment, or a combination thereof, and (ii) defining an equivalent number for the conceptual segment, the equivalent number being based on experimental phase equilibrium data and being one of carried in the databank of molecular descriptors of known chemical species or obtained using the calculator of molecular descriptors of unknown chemical species by regression of experimental phase equilibrium data for binary systems of unknown chemical species and known chemical species;
   c) providing the determined at least one conceptual segment to the modeler, and in response the modeler using the determined at least one conceptual segment to compute the retention time of the one or more chemical species in the mixture, the modeler computing the retention time by determining an activity coefficient of the one or more chemical species, the mobile phase component, and the stationary phase component;
   d) analyzing the computed retention time using the modeler, in a comparison to the computed retention times of other mixtures of at least two chemical species, and forming therefrom a model of the retention times of the one or more chemical species in the mixture useable in modeling chromatography; and
   e) outputting the formed model from the modeler to a computer display monitor in a manner enabling control of retention time during chromatographic operations on the one or more chemical species.

2. The method of claim 1, wherein the one or more chemical species is an active pharmaceutical ingredient.

3. The method of claim 1, wherein the mobile phase component includes one or more solvents.

4. The method of claim 1, wherein the stationary phase component includes one or more solvents and interacting surface areas.

5. The method of claim 1, wherein the at least one conceptual segment is a molecular descriptor to represent a molecular interaction characteristic of: a) the one or more chemical species, b) the mobile phase component, and c) the stationary phase component.

6. The method of claim 5 wherein the molecular interaction characteristic is a molecular surface interaction characteristic of a) the one or more chemical species, b) the mobile phase component, and c) the stationary phase component.

7. The method of claim 1, wherein determining the activity coefficient for the one or more chemical species, the mobile phase component and the stationary phase component includes providing data regarding partition characteristics of the known chemical species in a chromatography separation.

8. The method of claim 7 further including determining partition characteristics of the one or more chemical species with respect to the partition characteristics of the known chemical species.

9. The method of claim 8, wherein the data is partition coefficient data or retention factor data.

10. The method of claim 1 further including determining molecular interaction energy indices associated with each of the conceptual segments.

11. The method of claim 10, wherein the molecular interaction energy indices are segment-segment binary interaction energy parameters.

12. The method of claim 1, wherein the mobile phase component includes one or more solvents.

13. The method of claim 1, wherein determining the activity coefficient of the one or more chemical species, the mobile phase component or the stationary phase component uses the following formulae:

$$\ln \gamma_I = \ln \gamma_I^C + \ln \gamma_I^R,$$

wherein:
  $\gamma_I$, is an activity coefficient for the one or more chemical species, the mobile phase component or the stationary phase component;
  $\gamma_I^C$ is a combinatorial contribution to the activity coefficient for the one or more chemical species, the mobile phase component or the stationary phase component; and
  $\gamma_I^R$ is a residual contribution to the activity coefficient of the one or more chemical species, the mobile phase component or the stationary component.

14. The method of claim 13 wherein determining the activity coefficient of the one or more chemical species, the mobile phase component or the stationary phase component includes computing the following formulas:

$$\ln \gamma_I^R = \ln \gamma_I^{lc} = \sum_m r_{m,I}[\ln \Gamma_m^{lc} - \ln \Gamma_{m,I}^{lc}],$$

$$\ln \Gamma_m^{lc} = \frac{\sum_j x_j G_{jm} \tau_{jm}}{\sum_k x_k G_{km}} + \sum_{m'} \frac{x_{m'} G_{mm'}}{\sum_k x_k G_{km'}} \left( \tau_{mm'} - \frac{\sum_j x_j G_{jm'} \tau_{jm'}}{\sum_k x_k G_{km'}} \right), \text{ and}$$

$$\ln \Gamma_{m,I}^{lc} = \frac{\sum_j x_{j,I} G_{jm} \tau_{jm}}{\sum_k x_{k,I} G_{km}} + \sum_{m'} \frac{x_{m',I} G_{mm'}}{\sum_k x_{k,I} G_{km'}} \left( \tau_{mm'} - \frac{\sum_j x_{j,I} G_{jm'} \tau_{jm'}}{\sum_k x_{k,I} G_{km'}} \right),$$

wherein:
  I is a component index for the one or more chemical species, the mobile phase component, or the stationary phase component;
  each j, k, m, and m' is a segment species index;
  $x_j$ is a segment-based mole fraction of segment species j;
  $x_{j,I}$ is a segment-based mole fraction of segment species j in the I;
  $r_{m,I}$ is a number of segment species m contained in the I;
  $\Gamma_m^{lc}$ is an activity coefficient of segment species m;
  $\Gamma_m^{lc,I}$ is an activity coefficient of segment species m contained in the I; and
  G and $\tau$ are binary quantities related to each other by a non-random factor parameter $\alpha$ as in $G = \exp(-\alpha\tau)$.

15. The method of claim 1, wherein computing the retention time of the one or more chemical species includes computing a capacity ratio of the one or more chemical species.

16. The method of claim 15 wherein the capacity ratio is a function of the molecular interaction:
  a) between the one or more chemical species and the mobile phase component; and
  b) between the one or more chemical species and the stationary phase component.

17. The method of claim 15 wherein computing the capacity ratio includes using the following formulas:

$$k_I = \frac{t_{rI} - t_0}{t_0}, \text{ and}$$

$$k_I = \frac{x_s V_s}{x_m V_m} = K_I \Phi,$$

wherein:
  $k_I$, is a capacity ratio of the one or more chemical species;
  $t_{rI}$, is the retention time of the one or more chemical species;
  $t_0$ is an elution time for an inert tracer;
  $K_I$ is a partition coefficient;
  $\Phi$ is a phase ratio;
  $V_s$ is a volume of the stationary phase component;
  $V_m$, is a volume of the mobile phase component;
  $x_s$ is a concentration of the one or more chemical species interacting with the stationary phase component; and
  $x_m$ is a concentration of the one or more chemical species interacting with the mobile phase component.

18. The method of claim 17 further including computing the partition coefficient $K_I$ using the following formula:

$$K_I = \frac{\gamma_m^\infty}{\gamma_s^\infty},$$

wherein:
  $\gamma_m^\infty$ and $\gamma_s^\infty$ are the mobile phase and the stationary phase activity coefficients of the one or more chemical species at infinite dilution;
  $\gamma_m$ is a mobile phase activity coefficient of the one or more chemical species; and
  $\gamma_s$ is a stationary phase activity coefficient of the one or more chemical species.

19. The method of claim 1 further comprising selecting a composition of the mobile phase component, a composition of the stationary phase component and a temperature for separating the one or more chemical species in the mixture.

20. The method of claim 1, wherein the chromatography is reverse-phase chromatography, normal phase chromatography, hydrophobic interaction chromatography, hydrophilic interaction chromatography, ion-pair chromatography, or ion-exchange chromatography.

* * * * *